United States Patent
Spohn et al.

(10) Patent No.: US 8,147,464 B2
(45) Date of Patent: *Apr. 3, 2012

(54) DRIP CHAMBER AND FLUID LEVEL SENSING MECHANISM FOR A FLUID DELIVERY SYSTEM

(75) Inventors: Michael A. Spohn, Butler, PA (US); Thomas P. Joyce, Wilkins Township, PA (US); Michael J. Ehrenberg, Pittsburgh, PA (US); James A. Dedig, Pittsburgh, PA (US); John A. Haury, Sewickly, PA (US); Susan L. Felix, Pittsburgh, PA (US); Gerald W. Callan, Cranberry Township, PA (US); John D. Shearer, Jr., Herminie, PA (US); Herbert Grubic, Pittsburgh, PA (US); Ralph Kopacko, Irwin, PA (US); William D. Barlow, Pittsburgh, PA (US); Richard G. Critchlow, Oakmont, PA (US); Roderick H. Beaulieu, Cumberland, RI (US); Jennie Kwo, Cambridge, MA (US); Luis A. Pedraza, West Roxbury, MA (US)

(73) Assignee: MEDRAD, Inc., Indianola, PA (US)

( * ) Notice: Subject to any disclaimer, the term of this patent is extended or adjusted under 35 U.S.C. 154(b) by 347 days.

This patent is subject to a terminal disclaimer.

(21) Appl. No.: 12/476,513

(22) Filed: Jun. 2, 2009

(65) Prior Publication Data
US 2009/0247865 A1 Oct. 1, 2009

Related U.S. Application Data

(63) Continuation of application No. 10/825,866, filed on Apr. 16, 2004, now Pat. No. 7,556,619.

(51) Int. Cl.
*A61M 5/14* (2006.01)

(52) U.S. Cl. .................................................. 604/251
(58) Field of Classification Search .......... 604/251–256, 604/151; 600/500
See application file for complete search history.

(56) References Cited

U.S. PATENT DOCUMENTS
2,702,547 A 2/1955 Glass
(Continued)

FOREIGN PATENT DOCUMENTS
WO  WO9707841  3/1997
(Continued)

OTHER PUBLICATIONS
International Search Report for corresponding PCT Application PCT/US05/12562.

*Primary Examiner* — Kevin C Sirmons
*Assistant Examiner* — Andrew Gilbert
(74) *Attorney, Agent, or Firm* — David Schramm; Gregory L. Bradley

(57) ABSTRACT

The fluid injector system includes a source of injection fluid, a pump device, a fluid control device operably associated with the pump device, and a fluid path set in fluid connection with the source of injection fluid and the pump device. The fluid path set includes a drip chamber including an elongated body having a top end, a bottom end and a raised projection, the raised projection being substantially rectangular in shape and extending longitudinally from the top end along the drip chamber body and terminating adjacent to the bottom end. A fluid level sensing mechanism is operably associated with the fluid control device, and includes a drip chamber support for supporting the drip chamber body and a fluid level sensor associated with the drip chamber support. The drip chamber support is adapted to support the drip chamber body such that the raised projection is in operational contact with the fluid level sensor and the fluid level sensing mechanism is operable to transmit ultrasonic or light energy through the raised projection to be sensed by the fluid level sensor for sensing the injection fluid level in the drip chamber.

20 Claims, 37 Drawing Sheets

U.S. PATENT DOCUMENTS

| | | | |
|---|---|---|---|
| 4,094,318 A * | 6/1978 | Burke et al. | 604/65 |
| 4,181,130 A * | 1/1980 | Bailey | 604/253 |
| 4,243,031 A | 1/1981 | Genese | |
| 4,321,461 A * | 3/1982 | Walter et al. | 377/21 |
| 4,351,332 A | 9/1982 | Martin, III et al. | |
| 4,397,648 A * | 8/1983 | Knute | 604/253 |
| 4,464,172 A | 8/1984 | Lichtenstein | |
| 4,596,551 A | 6/1986 | Golinski et al. | |
| 4,623,331 A * | 11/1986 | Cewers et al. | 604/65 |
| 4,668,216 A * | 5/1987 | Martin et al. | 604/253 |
| 4,677,980 A | 7/1987 | Reilly et al. | |
| 4,838,856 A | 6/1989 | Mulreany et al. | |
| 4,858,127 A | 8/1989 | Kron et al. | |
| 4,909,797 A * | 3/1990 | Timothy | 604/253 |
| 5,002,528 A | 3/1991 | Palestrant | |
| 5,057,081 A * | 10/1991 | Sunderland et al. | 604/153 |
| 5,300,031 A | 4/1994 | Neer et al. | |
| 5,379,205 A | 1/1995 | Peng | |
| 5,383,858 A | 1/1995 | Reilly et al. | |
| 5,460,609 A | 10/1995 | O'Donnell | |
| 5,515,851 A | 5/1996 | Goldstein | |
| 5,531,734 A * | 7/1996 | Geckle et al. | 604/890.1 |
| 5,569,208 A | 10/1996 | Woelpper et al. | |
| 5,573,515 A | 11/1996 | Wilson et al. | |
| 5,584,671 A | 12/1996 | Schweitzer, Jr. et al. | |
| 5,681,294 A * | 10/1997 | Osborne et al. | 604/251 |
| 5,779,675 A | 7/1998 | Reilly et al. | |
| 5,800,397 A | 9/1998 | Wilson et al. | |
| 5,840,026 A | 11/1998 | Uber, III et al. | |
| 5,873,861 A | 2/1999 | Hitchins et al. | |
| 5,916,165 A | 6/1999 | Duchon et al. | |
| 5,947,935 A | 9/1999 | Rhinehart et al. | |
| 5,950,262 A | 9/1999 | Smoler et al. | |
| 6,096,011 A | 8/2000 | Trombley, III et al. | |
| 6,099,502 A * | 8/2000 | Duchon et al. | 604/131 |
| 6,221,045 B1 | 4/2001 | Duchon et al. | |
| 6,336,913 B1 | 1/2002 | Spohn et al. | |
| 6,471,674 B1 | 10/2002 | Emig et al. | |
| 6,866,654 B2 | 3/2005 | Callan et al. | |
| 7,065,812 B2 | 6/2006 | Newkirk et al. | |
| 7,094,216 B2 | 8/2006 | Trombley, III et al. | |
| 7,549,977 B2 | 6/2009 | Schriver et al. | |
| 7,556,619 B2 * | 7/2009 | Spohn et al. | 604/251 |
| 7,563,249 B2 | 7/2009 | Schriver et al. | |
| 7,837,651 B2 * | 11/2010 | Bishop et al. | 604/122 |
| 7,879,008 B2 | 2/2011 | Haury et al. | |
| 2004/0122369 A1 * | 6/2004 | Schriver et al. | 604/152 |
| 2004/0242996 A1 | 12/2004 | Trombley, III et al. | |
| 2004/0254533 A1 | 12/2004 | Schriver et al. | |
| 2008/0051732 A1 * | 2/2008 | Chen | 604/253 |

FOREIGN PATENT DOCUMENTS

| | | |
|---|---|---|
| WO | WO0010629 | 3/2000 |
| WO | WO0204049 | 1/2002 |

* cited by examiner

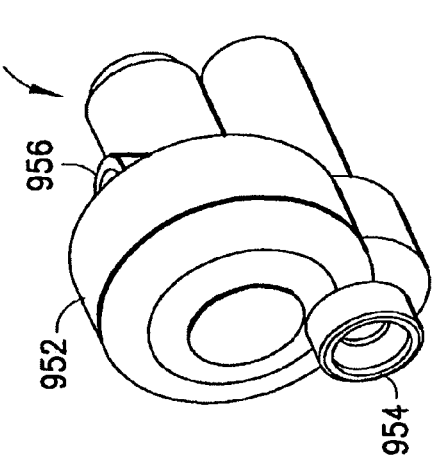
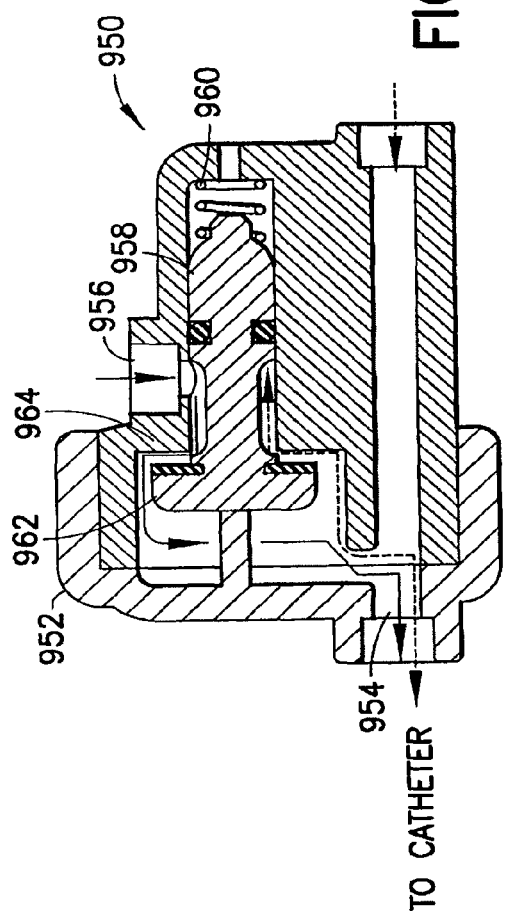
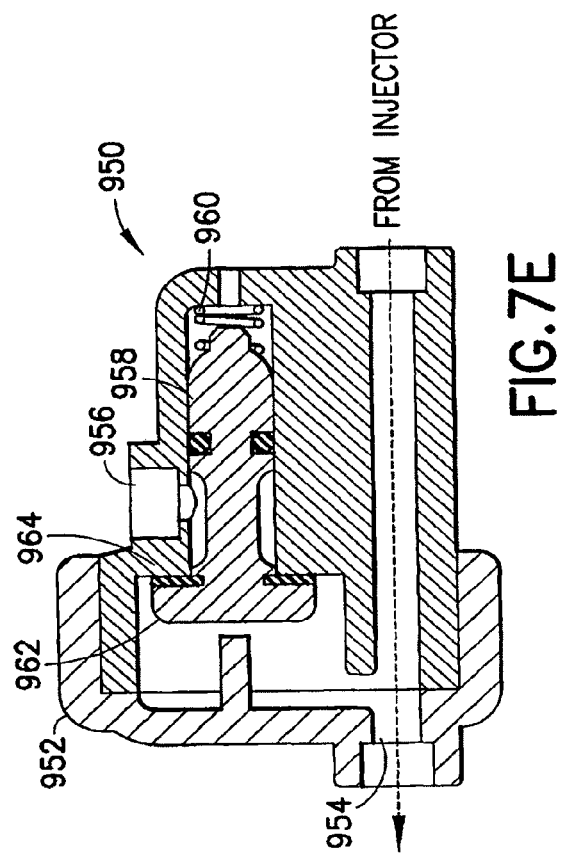

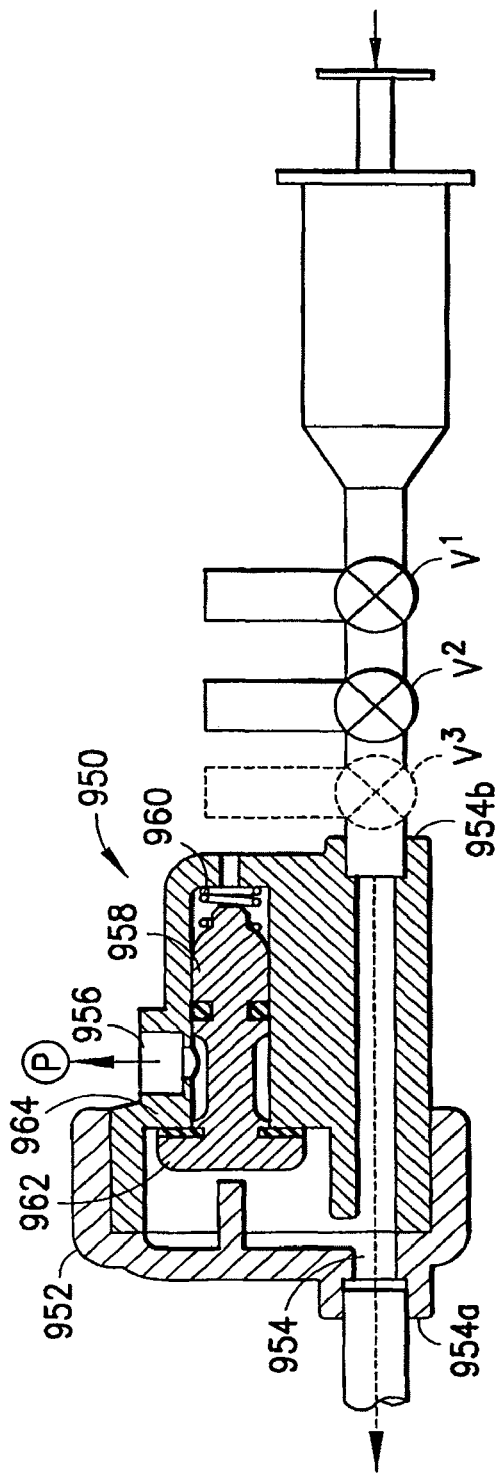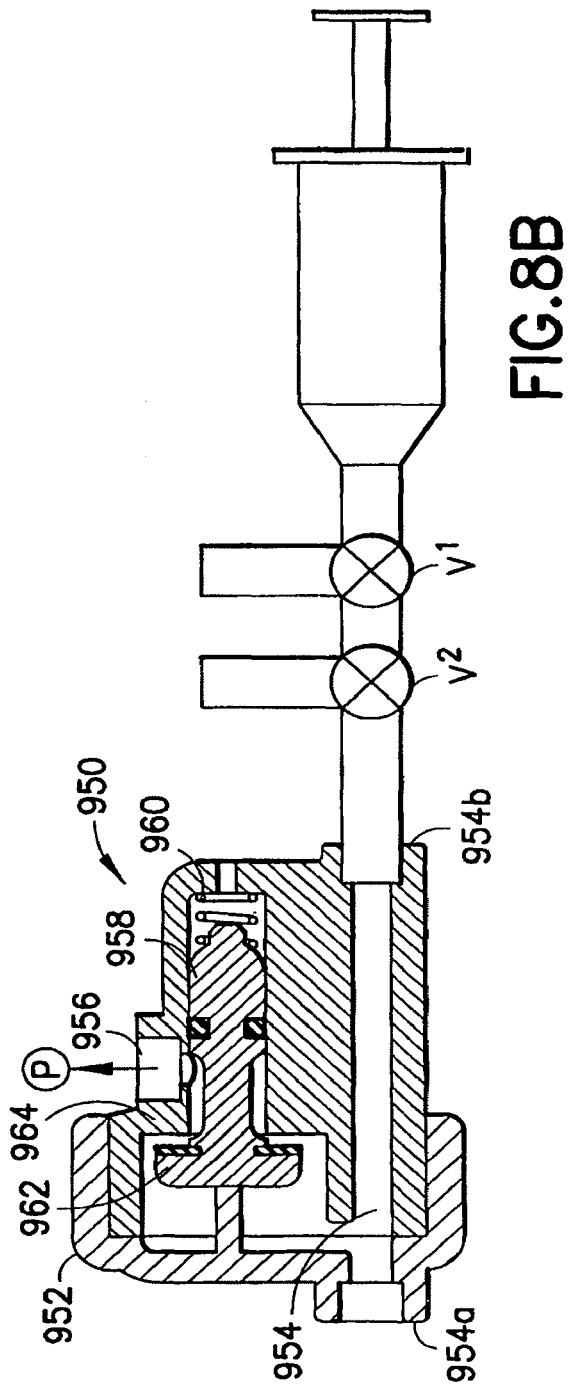

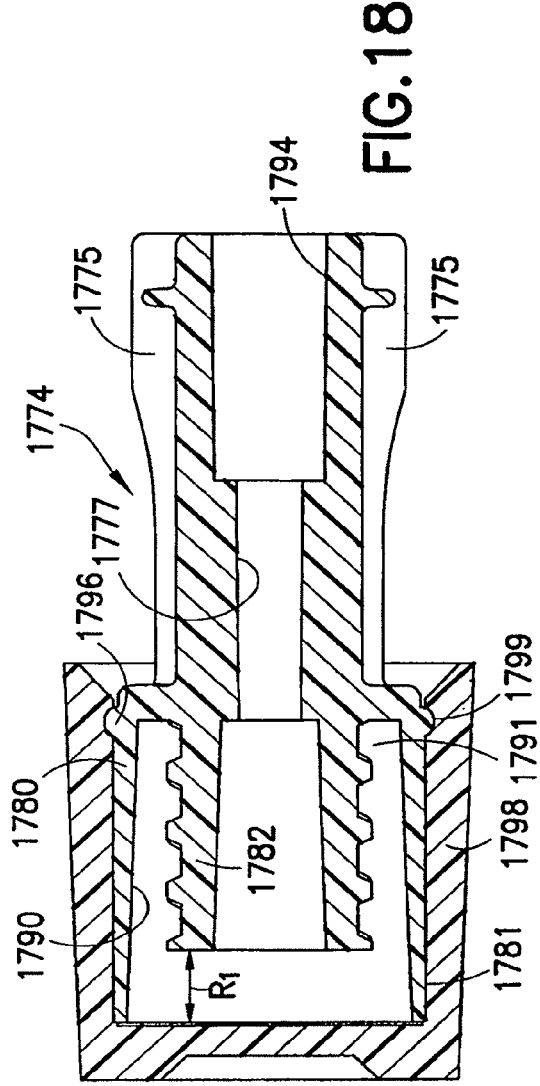
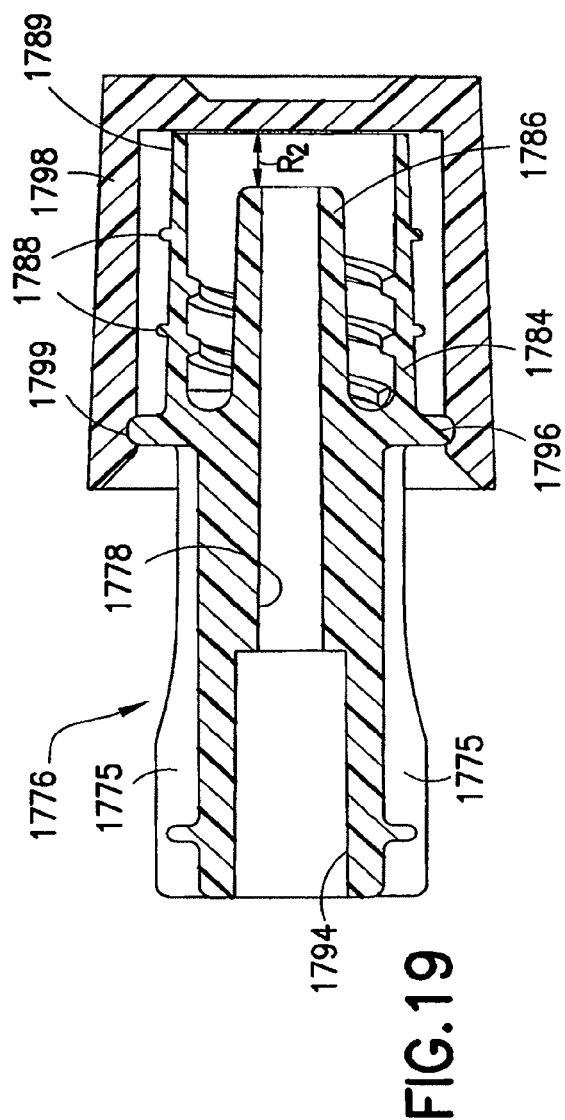

DRIP CHAMBER AND FLUID LEVEL SENSING MECHANISM FOR A FLUID DELIVERY SYSTEM

CROSS-REFERENCE TO RELATED APPLICATION

This application is a continuation of application Ser. No. 10/825,866, filed on Apr. 16, 2004, now U.S. Pat. No. 7,556,619, the disclosure of which is incorporated herein by reference.

RELATED APPLICATIONS

This application may contain subject matter that is related to that disclosed in the following applications: (1) application Ser. No. 10/818,748, filed on Apr. 6, 2004, now U.S. Pat. No. 7,326,186; (2) application Ser. No. 10/818,477, filed on Apr. 5, 2004, now U.S. Pat. No. 7,563,249; (3) application Ser. No. 10/326,582, filed on Dec. 20, 2002, now U.S. Pat. No. 7,549,977; (4) application Ser. No. 10/237,139, filed on Sep. 6, 2002, now U.S. Pat. No. 6,866,654; and (5) application Ser. No. 09/982,518, filed on Oct. 18, 2001, now U.S. Pat. No. 7,094,216, the disclosures of which are incorporated herein by reference.

BACKGROUND OF THE INVENTION

1. Field of the Invention

The present invention relates generally to fluid delivery systems for supplying fluids during medical diagnostic and therapeutic procedures, further, to fluid transfer sets and flow controlling and regulating devices associated therewith used with fluid delivery systems for conducting and regulating fluids flows.

2. Description of Related Art

In many medical diagnostic and therapeutic procedures, a physician or other person injects a patient with a fluid. In recent years, a number of injector-actuated syringes and powered injectors for pressurized injection of fluids, such as contrast media, have been developed for use in procedures such as angiography, computed tomography, ultrasound, and NMR/MRI. In general, these powered injectors are designed to deliver a preset amount of contrast media at a preset flow rate.

Angiography is used generally in the detection and treatment of abnormalities or restrictions in blood vessels. In an angiographic procedure, a radiographic image of vascular structure is obtained through the use of a radiographic contrast medium, sometimes referred to simply as contrast, injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a monitor and recorded.

In a typical angiographic procedure, a physician places a cardiac catheter into a vein or artery. The catheter is connected to either a manual or to an automatic contrast injection mechanism. A typical manual contrast injection mechanism, as illustrated, for example, in FIG. 1, includes a syringe in fluid connection with a catheter connection. The fluid path also includes, for example, a source of contrast fluid, a source of saline, and a pressure transducer P to measure patient blood pressure. In a typical system, the source of contrast is connected to the fluid path via a valve $V^1$, for example, a three-way stopcock. The source of saline and pressure transducer P may also be connected to the fluid path via additional valves $V^2$ and $V^3$, respectively. The operator of the manual system of FIG. 1, manually controls the syringe and each of the valves $V^1$ and $V^2$ to draw saline or contrast into the syringe and to inject the saline or contrast into the patient through the catheter connection. The pressure transducers used in such procedures are extremely sensitive to even moderately high pressures generated during activation of the syringe, so the operator must close valve $V^3$ to isolate pressure transducer P from the fluid path when the syringe is activated to prevent damage to pressure transducer P. While the syringe is not activated, valve $V^3$ is usually open to monitor patient blood pressure.

The operator of the syringe of FIG. 1 may adjust the flow rate and volume of injection by altering the force applied to the plunger of the syringe. Manual sources of fluid pressure and flow used in medical applications such as syringes and manifolds thus typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast material and a fixed rate of injection. In many systems, there is no interactive control between the operator and the powered injector, except to start or stop the injection. A change in flow rate in such systems occurs by stopping the machine and resetting the parameters. Automation of angiographic procedures using powered injectors is discussed, for example, in U.S. Pat. Nos. 5,460,609, 5,573,515 and 5,800,397.

U.S. Pat. No. 5,800,397 discloses an angiographic injector system having high pressure and low pressure systems. The high pressure system includes a motor-driven injector pump to deliver radiographic contrast material under high pressure to a catheter. The low pressure system includes, among other things, a pressure transducer to measure blood pressure and a pump to deliver a saline solution to the patient as well as to aspirate waste fluid. A manifold is connected to the syringe pump, the low pressure system, and the patient catheter. A flow valve associated with the manifold is normally maintained in a first state connecting the low pressure system to the catheter through the manifold, and disconnecting the high pressure system from the catheter and the low pressure system. When pressure from the syringe pump reaches a predetermined and set level, the valve switches to a second state connecting the high pressure system/syringe pump to the catheter, while disconnecting the low pressure system from the catheter and from the high pressure system. In this manner, the pressure transducer is protected from high pressures, (see column 3, lines 20-37 of U.S. Pat. No. 5,800,397). However, compliance in the system components, for example, expansion of the syringe, tubing, and other components under pressure, using such a manifold system can lead to a less than optimal injection bolus. Moreover, the arrangement of the system components of U.S. Pat. No. 5,800,397 results in relatively large amounts of wasted contrast and/or undesirable injection of an excessive amount of contrast when the low pressure, typical saline system, is used. The injector system of U.S. Pat. No. 5,800,397 also includes a handheld remote control connected to a console. The control includes saline push button switches and a flow rate control lever or trigger. By progressive squeezing of the control trigger, the user provides a command signal to the console to provide a continuously variable injection rate corresponding to the degree of depression of the control trigger.

U.S. Pat. No. 5,916,165 discloses a handheld pneumatic controller for producing a variable control signal to control a rate of fluid dispersement to the patient in an angiographic system. U.S. Pat. No. 5,515,851 discloses an angiographic system with a finger activated control pad to regulate the injection of fluids.

Unlike manual injection systems, however, there is little if any feedback to the operator of system pressure in the systems disclosed in the U.S. Patents identified previously. There are potential advantages to such feedback. In the use of a manual syringe, for example, excessive back pressure on the syringe plunger can provide evidence of occlusion of the fluid path.

U.S. Pat. No. 5,840,026 discloses, an injection system in which an electronic control system is connected to the contrast delivery system and a tactile feedback control unit. In one embodiment, the tactile feedback control unit includes a disposable syringe that is located within a durable/reusable cradle and is in fluid connection with the fluid being delivered to the patient. The cradle is electrically connected to the electronic control system and is physically connected to a sliding potentiometer that is driven by the plunger of a disposable syringe. During use of the injection system of U.S. Pat. No. 5,840,026, the operator holds the cradle and syringe and, as the operator depresses the sliding potentiometer/syringe piston assembly, the plunger is moved forward, displacing fluid toward the patient and creating a pressure in the syringe. A sliding potentiometer tracks the position of the syringe plunger. The electronic control system controls the contrast delivery system to inject an amount of fluid into the patient based on the change in position of the plunger. As the fluid is injected, the pressure the operator feels in his or her hand is proportional to the actual pressure produced by the contrast delivery system. The force required to move the piston provides the operator with tactile feedback on the pressure in the system. The operator is able to use this feedback to ensure the safety of the injection procedure. Unlike the case of a manual injection system, the injection system of U.S. Pat. No. 5,840,026 does not require the operator to develop the system pressure and flow rate. The operator develops a smaller, manually applied pressure that corresponds to or is proportional to the system pressure. The required manual power output (that is, pressure×flow rate) is decreased as compared to manual systems, whereas the tactile feedback associated therewith is retained.

While manual and automated injectors are know in the medical field, a need generally exists for improved fluid delivery systems adapted for use in medical diagnostic and therapeutic procedures where fluids are supplied to a patient during the procedure. A specific need generally exists for an improved fluid delivery system for use in fluid injection procedures, such as angiography. Additionally, a need generally exists for fluid transfer sets and flow controlling and regulating devices associated therewith that may be used with fluid delivery systems for conducting and regulating fluids flows. Moreover, a continuing need exists in the medical field to generally improve upon known medical devices and systems used to supply fluids to patients during medical procedures such as angiography, computed tomography, ultrasound, and NMR/MRI.

SUMMARY OF THE INVENTION

The present invention provides an injector system including a powered injector, a pressurizing chamber in operative connection with the powered injector, a fluid path in fluid connection with the pressurizing chamber, and a manual control in fluid connection with the fluid path. The manual control includes at least one actuator for controlling the injector through application of force by an operator. The actuator provides tactile feedback of pressure in the fluid path to the operator via direct or indirect operative or fluid connection with the fluid path (i.e., pressure in the fluid path transfers a corresponding or a proportional force to the operator). In one embodiment, the actuator is adapted to stop an injection procedure if no force is applied to the actuator. The manual control may, for example, include a chamber in fluid connection with the fluid path. The actuator may be a button or a plunger in operative connection with a piston disposed within the chamber. The actuator may be biased in an off position.

In another aspect, the manual control includes a first actuator for controlling the injector in a low pressure mode through application of force by an operator. The first actuator provides tactile feedback of pressure in the fluid path to the operator via fluid connection with the fluid path as described previously. The first actuator also provides control of flow rate by changing the force thereon. The manual control also may include a second actuator having an on state and an off state. The second actuator causes the injector to enter into a preprogrammed high-pressure injection mode when placed in the on state. The manual control may also include a third actuator for controlling flow of saline in the fluid path.

In another aspect of the present invention, the actuator provides tactile feedback of fluid pressure and is also in operative connection with an audible feedback unit that provides audible feedback of fluid pressure and/or fluid flow to the operator. The manual controls of the present invention may be purged of air before injection via, for example, a purge valve.

The present invention also provides a system for injection of fluid into a patient including a multi-patient reusable section and a per-patient disposable section. The multi-patient reusable section and the per-patient disposable section are removably connectable via a connector or connectors, for example, via a high-pressure connector. The multi-patient reusable section includes a powered injector in fluid connection with a source of a first injection fluid and a first fluid path connecting the injector and a high-pressure connector. The per-patient disposable section includes a second fluid path adapted to connect the high-pressure connector and the patient in fluid connection. The per-patient disposable section further includes a manual control as described above including a connector to place the manual control in fluid connection with the second fluid path. The multi-patient reusable section may further include a valve mechanism connecting the injector, first fluid source, and the first fluid path.

In one embodiment, the multi-patient reusable section further includes a source of a second injection fluid and a pumping mechanism in fluid connection with the second fluid source for pressurizing the second fluid. The pumping mechanism is preferably in fluid connection with the valve mechanism.

In one aspect, the manual control includes a first actuator providing control of flow rate of the first fluid by changing the force on the first actuator and a second actuator, the second actuator causing the injector to enter into a preprogrammed high pressure injection mode when placed in an on state. The system may further include a pressure sensor in fluid communication with the second fluid path via a pressure-activated isolator that isolates the pressure sensor from pressures in the second fluid path above a set pressure. In one embodiment, the per-patient disposable section may include a check valve in the second fluid path separating components of the per-patient disposable section from the multi-patient reusable section to reduce or eliminate flow of contaminated fluid into the multi-patient reusable section.

The present invention further provides a method of injecting a fluid into a patient including the steps of: removably connecting a multi-patient reusable section to a per-patient disposable section via a high-pressure connector, the multi-patient reusable section including a powered injector in fluid connection with a source of a first injection fluid and a first fluid path connecting the injector and the high-pressure connector, the per-patient disposable section including a second fluid path adapted to connect the high-pressure connector and the patient in fluid connection; connecting a manual control including a connector to the second fluid path to place the manual control in fluid connection with the second fluid path, the manual control including at least one actuator for controlling the powered injector through application of force by an operator, the actuator being adapted to provide tactile feedback of pressure in the second fluid path to the operator via fluid connection with the second fluid path; and injecting a fluid into a patient.

The method may further include the step of connecting a pressure sensor in fluid communication with the second fluid path via a pressure activated isolator that isolates the pressure sensor from pressures in the second fluid path above a set pressure.

Still further, the present invention provides a per-patient disposable set for use in an injection procedure including a fluid path adapted to form a fluid connection between a high-pressure connector and the patient, and a manual control in fluid connection with the fluid path. The manual control includes at least one actuator for controlling the powered injector through application of force by an operator. The actuator is adapted to provide tactile feedback of pressure in the fluid path to the operator via fluid connection with the fluid path. The per-patient disposable set further includes a pressure sensor in fluid connection with the fluid path via a pressure activated isolator adapted to isolate the pressure sensor from pressures in the fluid path above a set pressure.

The manual, for example, handheld controllers of the present invention provide a number of advantages including, but not limited to the following: tactile feedback of actual fluid path pressure via fluid communication with the fluid path, compact size and small priming volume; dead man switch capability; ergonomic design for control of both contrast and saline; injection pressure feedback linked to variable flow and audible feedback; rigid material construction; actuator control providing a progressively increasing flow rate as the actuator is pushed or depressed through its range of motion; and high-pressure injections that are greater in pressure than could be generated or tolerated by an operator's hand.

In another aspect, the present invention provides an injection system for use in angiography including a powered injector in fluid connection with a source of injection fluid and a pressure sensor in fluid connection with the powered injector via a pressure activated isolator adapted to isolate the pressure sensor from pressures in the fluid path above a set pressure. The pressure sensor elevation is independent of or independently variable of the position of the remainder of the injection system, including the position or elevation of the powered injector.

In a further aspect, the present invention provides an angiographic injection system for injecting an injection fluid into a patient including a pressurizing device for supplying injection fluid under pressure; a low pressure fluid delivery system; and a pressure isolation mechanism having a first port for connection to the pressurizing device, a second port for connection to the patient, and a third port for connection to the low pressure fluid delivery system. The pressure isolation mechanism includes a valve having a first state and a second state different from the first state. Preferably, the first state and the second state are mutually exclusive of each other. The first state occurs when the second and third ports are connected and the first and third ports are connected. The second state occurs when the first and second ports are connected and the first and third ports are disconnected. The valve is normally biased to the first state via, for example, a spring, and is switchable to the second state when fluid pressure from the syringe pump reaches a predetermined pressure level. The first and second ports remain connected in the first state and in the second state.

The system preferably further includes a valve in line between the pressurizing device and the first port of the pressure isolation mechanism to control flow of the injection fluid. Preferably, the valve is an automated valve. The valve is preferably operable to minimize or eliminate the effects of compliance of the pressurizing device and related tubing.

The low pressure delivery system may include a source of saline or other suitable flushing medium, a drip chamber in fluid connection with the source of saline, and a detector to sense the amount of saline in the source of saline. The system may further include a saline control valve and an air detector in line between the saline drip chamber and the pressure isolation mechanism.

The pressurizing device may be in fluid connection with a source of injection fluid via an injection fluid drip chamber. The system may further include a detector to sense the amount of injection fluid in the source of injection fluid. Likewise, the system may also include an injection fluid control valve and an air detector in line between the injection fluid drip chamber and the pressure isolation mechanism.

In one embodiment, the system further includes a handheld controller to control injection of injection fluid and injection of saline. The handheld controller may include a first control having a first mode to control injection of injection fluid in a low pressure mode, the flow rate of the injection corresponding to, for example, being proportional to, the distance the first control is depressed. Preferably, the low pressure injection is ceased if the first control is released while in the first mode. The first control may, for example, have a second mode to control injection of injection fluid in a high pressure mode. The high pressure mode injection is preferably ceased if the first control is released while in the second mode. The hand controller may further include at least a second control to control injection of saline. Preferably, the injection of saline is ceased if the second control is released during injection of saline.

The system preferably further includes a pressure transducer in fluid connection with the third port of the pressure isolation mechanism.

In still a further aspect, the present invention provides an injection system for use in angiography including a source of saline, a pump in fluid connection with the source of saline to pressurize the saline, a saline valve in fluid connection via a first port thereof with an outlet of the pump, a first connector in fluid connection with a second port of the saline valve, a source of contrast, a contrast valve in fluid connection with the source of contrast via a first port of the contrast valve, a powered injector in fluid connection with a second port of the contrast valve, a second connector in fluid connection with a third port of the contrast valve, and a pressure isolation mechanism.

The pressure isolation mechanism has a lumen having a first port in fluid connection with the second connector and a second port in fluid connection with a patient catheter. The isolation mechanism further has a third port in fluid connection with the first connector and with the lumen. The pressure isolation mechanism further includes a valve having a first state and a preferably mutually exclusive second state—the first state occurring when the lumen and the third port are connected, and the second state occurring when the lumen and the third port are disconnected. The valve is preferably normally biased to the first state and is switchable to the second state when fluid pressure from the powered injector reaches a predetermined pressure level. The first and second ports of the lumen preferably remain connected whether in the first state or in the second state. The system further includes a pressure transducer in fluid connection with the third port of the pressure isolation mechanism.

The system may also include a first air or air column detector in fluid connection between the saline valve and the first connector and a second air detector in fluid connection between the contrast valve and the second connector.

The system may also include a first drip chamber in fluid connection between the source of saline and the pump and a detector in operative connection with the first drip chamber to sense the amount of saline in the source of saline. Likewise, the system may include a second drip chamber in fluid connection between the source of contrast and the contrast valve and a detector in operative connection with the second drip chamber to sense the amount of injection fluid in the source of injection fluid. One advantage of a drip chamber is to reduce likelihood of introduction of air into the system once the system has been initially purged of air or primed.

In another aspect, the present invention provides a pressure isolation mechanism for use in a medical procedure. The pressure isolation mechanism or pressure isolator includes a lumen, an isolation port in fluid connection with lumen, and a valve having a first state and a second state. The first state occurs when the lumen and the isolation port are connected. The second state occurs when the lumen and the isolation port are disconnected. The lumen remains open for flow of fluid therethrough in the first state and in the second state. The valve is normally in the first state and is switchable to the second state when fluid pressure in the lumen reaches a predetermined pressure level. The valve may, for example, be biased to the first state, for example, via a spring or other mechanism suitable to apply a biasing force as known in the art. A pressure sensor or transducer can be in fluid connection with the isolation port of the pressure isolation mechanism as described previously.

The valve may be switched between the first state and the second state by the force of the fluid pressure. Alternatively, an electromechanical actuator in operative connection with a pressure sensor may control the state of the valve as a function of the fluid pressure. The pressure sensor may, for example, be a pressure transducer in fluid connection with the isolation port as described previously.

In general, the pressure isolation mechanism is useful in any medical procedure in which is it desirable to isolate a fluid pathway or fluid path component from fluid flow above a certain fluid pressure. The fluid pathway or fluid path component is placed in fluid connection with the isolation port of the pressure isolation mechanism. For example, a pressure transducer may be placed in connection with the isolation port to protect the pressure transducer form damage as a result of exposure to excess fluid pressure.

In a further aspect, the present invention provides a fluid delivery system including a manually operated syringe and a pressure isolation mechanism as described above.

The present invention provides in another aspect a method of adding a patient pressure transducer to a fluid path used in a medical procedure to deliver fluid to a patient. The method includes the step of placing a lumen of a pressure isolation mechanism as described above in the fluid path via, for example, a first port and a second port of the lumen. The method also includes the steps of connecting a pressure transducer to the third or isolation port of the pressure isolation mechanism. The method is useful, for example, in adding a patient pressure transducer to an angiographic fluid delivery system including a manual syringe.

The present invention is further directed to a fluid path set for use generally in a fluid delivery system. The fluid path set generally includes a first section generally adapted for association with a pressurizing device such as a syringe, and a second section adapted for removable fluid communication with the first section. The first section may be a multi-patient section of the fluid path set, and the second section may be a single or per-patient section of the fluid path set and be disposable after use with a single patient. The multi-patient section may be disposable after a preset number of uses with the fluid delivery system. Additionally, the multi-patient section may be provided as a single patent set or section, disposed of after use with a single patient or injection procedure. Further, it is within the scope of the present invention to provide the first and second sections of the fluid path set as multi-use components that may be re-sterilized after each use or injection procedure. The first section may be adapted for connection to a source of fluid to be loaded into a pressurizing device. The first section may comprise a multi-position valve adapted to selectively isolate the fluid source and the second section.

Another aspect of the present invention is directed to a connector for use in a fluid delivery or transfer system or arrangement, and generally adapted to reduce the likelihood of contamination at connection points in the fluid path set when changing components in the fluid path set. The connector may be used with the fluid path set for providing removable fluid communication between the first section and the second section. The connector is configured to reduce contamination when connecting one or more typically disposable second sections with a typically multiple-patient first section in the fluid path set. The connector generally includes a first connector member and a second connector member, which are generally adapted to removably connect with one another. The first and second connector members may be associated with either the first section or the second section. Thus, if the first connector member is associated with the first section, the second connector member is associated with the second section, and vice versa. The first connector member includes an outer housing and a first threaded member disposed in the outer housing. The second connector member includes a second threaded member. The first threaded member and second threaded member cooperate to securely and releasably connect the first member to the second member, when the first connector member is connected to the second connector member. The connection of the first connector member with the second connector member generally establishes the removable fluid communication between the first section and the second section, when the connector is used therewith. The second threaded member is preferably received in the outer housing of the first connector member when the first connector member is connected to the second connector member.

The first threaded member may be recessed within the outer housing. The first threaded member may be formed as an externally-threaded luer, which may be recessed within the outer housing. The second member may include a luer disposed in the second threaded member and adapted to cooperate with the first threaded member. The luer may be recessed within the second threaded member.

The first threaded member may be formed as an externally-threaded female luer, and the second member may include a male luer disposed in the second threaded member, such that the male luer cooperates with the female luer when the first connector member is connected to the second connector member. One or both of the female luer and the male luer may be recessed within the outer housing and the second threaded member, respectively.

The first threaded member may be externally-threaded and the second threaded member may be internally-threaded. The second threaded member may include at least one circumferentially-extending raised structure on an external surface thereof. The raised structure may define a tortuous path with an inner wall of the outer housing for inhibiting liquid flow between the outer housing and the second threaded member when the first connector member is connected to the second connector member. The raised structure may define a chamber with the inner wall of the outer housing and the first threaded member when the first connector member is connected to the second connector member.

Protective caps may be associated with the first connector member and the second connector member, respectively, prior to connecting the first connector member and the second connector member. The first and second connector members may each include a raised tab adapted to cooperate with a corresponding groove defined internally in the protective caps, for securing removable engagement between the first and second connector members and the respective protective caps. The protective caps may be disposable or reusable items.

An additional aspect of the present invention is directed to a pressure isolation mechanism that may be used, for example, with the fluid path set. For example, the second section of the fluid path set may include the pressure isolation mechanism. The pressure isolation mechanism generally comprises a lumen, a pressure isolation port, and a valve member. The valve member includes a biasing portion biasing the valve member to a normally open position permitting fluid communication between the lumen and the pressure isolation port. The valve member is movable to a closed position when fluid pressure in the lumen reaches a predetermined pressure level sufficient to overcome the biasing force of the biasing portion of the valve member.

The pressure isolation mechanism may have a housing that defines the lumen and the pressure isolation port. A pressure transducer may be associated with the pressure isolation port. The valve member may comprise a seat member and a base portion engaged with the seat member. The biasing portion of the valve member may be a generally cone-shaped portion of the seat member. The generally cone-shaped portion preferably has a predetermined spring force. The piston may include a seat member and a base portion engaged with the seat member. The base portion may be adapted to engage a housing of the pressure isolation mechanism in the closed position of the valve member. The seat member may define an aperture and the base portion may be formed with a projection engaged with the aperture for connecting the base portion to the seat member. The base portion may be joined to the seat member by mechanical connection therewith or bonded to the seat member, for example with an adhesive.

The pressure isolation mechanism may have a multi-piece housing, such as a two-piece housing including a first portion cooperating with a second portion. The first portion may be in an interference fit engagement with the second portion. The first portion and second portion may be formed to define a tortuous or shear interface therebetween to enhance strength.

A still further aspect of the present invention is directed to an improved drip chamber that may be used as part of the fluid path set. For example, one or more drip chambers may be used with the first section, or the second section. In one embodiment, the first section includes an intervening drip chamber between the primary fluid source and the syringe. The drip chamber generally comprises a projection useful for determining a level of fluid in the drip chamber. The projection is preferably raised from the body of the drip chamber, and may extend longitudinally or laterally along the body of the drip chamber.

Additionally, the first section may be adapted for connection to a secondary source of fluid to be delivered to a patient, such as saline. An intervening drip chamber may also be associated with the secondary fluid source and the first section. The drip chamber associated with the secondary fluid source preferably also has a projection for determining a level of fluid in the drip chamber, which is also preferably raised from the body of the drip chamber. The second section may be further adapted for removable fluid communication with the first section, such that the secondary fluid source is in fluid communication with the pressure isolation port. The intervening drip chamber associated with the secondary fluid source may be located between the secondary fluid source and the pressure isolation port.

The present invention is further directed as a method of preparing a fluid delivery system for association with a patient. The method generally includes providing the fluid delivery system including an injector, associating a syringe with the injector, and providing the fluid path set comprising the first section and the second section. The first section may be connected with the syringe, and the second section connected to the first section to provide removable fluid communication therebetween.

The first section may be removably connected to the second section with the connector described previously. The second section is generally placed in removable fluid communication with the first section by connecting the first connector member and the second connector member of the connector. The second threaded member of the second connector is received in the outer housing of the first connector member when the first connector member and second connector member are connected.

Additionally, the present invention is a method of delivering fluid to a patient, generally providing a fluid delivery system including an injector, associating a syringe with the injector, and providing the fluid path set comprising the first section and the second section. The first section may be connected with the syringe, and the second section connected to the first section to provide removable fluid communication therebetween. The second section may then be connected to the patient and the injector actuated to deliver fluid to the patient. When the fluid delivery procedure is complete, the injector may be deactuated to terminate delivery of fluid to the patient, and the second section of the fluid path set may be disconnected from the patient.

The first section may be removably connected to the second section with the connector described previously. The second section is generally placed in removable fluid communication with the first section by connecting the first connector member and the second connector member of the connector. The second threaded member of the second connector is received in the outer housing of the first connector member when the first connector member and second connector member are connected.

The method of delivering fluid to the patient may further include disconnecting the second section from the first section and providing a new second section. The new second section may be connected to the existing first section to provide removable fluid communication therebetween. The new second section may be connected to the same patient or a new patient, and the injector may be actuated to deliver fluid to the patient. The present invention is additionally directed to an injection system including a source of injection fluid, a pump device, and a fluid path set, summarized previously, disposed between the source of injection fluid and the pump device. The first and second sections of the fluid path set may be connected using one or more of the connectors discussed previously.

The present invention is also an injector system that generally includes a source of injection fluid, a pump device, a fluid path set disposed between the source of injection fluid and the pump device, and a fluid control device. The fluid path set includes a multi-position valve. The fluid control device is operatively associated with the fluid path set and includes a valve actuator adapted to operate the multi-position valve. The valve actuator is adapted to close the multi-position valve to isolate the pump device from a patient and stop flow of the injection fluid to the patient at substantially any pressure or flow rate generated by the pump device for delivering a sharp bolus of the injection fluid to the patient. The valve actuator may be further adapted to selectively place the pump device in fluid communication with the source of injection fluid for supplying the injection fluid to the pump device.

The valve actuator may include a position indicator indicating a position of the multi-position valve. The valve actuator may include a sensor indicating presence of the multi-position valve in the valve actuator. The valve actuator may include a retainer for removably supporting the multi-position valve.

The fluid path set may include a drip chamber and the fluid control device may include a fluid level sensing mechanism operatively associated with the drip chamber for sensing the injection fluid level in the drip chamber. An air column detector may be operatively associated with the fluid path set. The pump device of the injector system may be a powered injector.

A source of medical fluid may be associated with the fluid path set, and a pump operatively associated with the source of medical fluid for supplying the medical fluid to the patient via the fluid path set. The fluid path set may include a drip chamber and the fluid control device may include a fluid level sensing mechanism operatively associated with the drip chamber for sensing the medical fluid level in the drip chamber. A shut-off valve may be associated with the pump for stopping flow of the medical fluid to the patient. The shut-off may be an automated pinch valve. The pump may be a peristaltic pump. The fluid control device may further include guides for securing the fluid path set in association with the pump. A hand held control device may be associated with the pump device or the fluid control device for controlling the flow rate of the injection fluid from the pump device.

The injector system may further include a drip chamber having a body with a projection, and a fluid level sensing mechanism. The fluid level sensing mechanism may include a drip chamber support for supporting the drip chamber body, and a fluid level sensor associated with the drip chamber support. The drip chamber support is generally adapted to support the drip chamber body such that the projection is operatively associated with at least one fluid level sensor. The fluid level sensor may be an ultrasonic or optical fluid level sensor. The drip chamber support may be adapted to support the drip chamber body such that the projection is in contact with the fluid level sensor. The injector system may further include an indicator light associated with the fluid level sensor for illuminating the drip chamber. The fluid level sensing mechanism is adapted to cause the indicator light to intermittently operate if a fluid level in the drip chamber is at an unsafe level The present invention further encompasses an air detector assembly for the fluid control device comprising. The air detector assembly includes an air column detector adapted to detect the presence of air in medical tubing, and a retaining device for securing the medical tubing in operative association with the air column detector. The retaining device generally includes a base adapted for association with the air column detector, and a closure member connected to the base and adapted to secure the medical tubing in operative association with the air column detector.

The closure member is generally movable from a closed position wherein the closure member secures the medical tubing in operative association with the air column detector, to an open position allowing the medical tubing to be disassociated from the air column detector. The closure member is preferably biased to the open position and secured in the closed position by a releasable locking mechanism. The closure member may be secured in the closed position by a releasable locking mechanism. The closure member may be formed of substantially clear plastic material to permit viewing of the medical tubing.

The present invention is also a fluid control device for connecting a pump device to a source of injection fluid. The fluid control device includes a fluid path set comprising a multi-position valve adapted to associate a patient and the source of injection fluid with the pump device, and a valve actuator adapted to operate the multi-position valve to selectively isolate the pump device from the patient, and place the pump device in fluid communication with the source of injection fluid for supplying the injection fluid to the pump device.

The present invention is a method of preparing the fluid delivery system to deliver an injection fluid to a patient, generally including providing a pump device for supplying the injection fluid to the patient under pressure, providing a fluid control device, associating a fluid path set with the fluid control device, and connecting the pump device with the source of the injection fluid via the fluid path set. The pump device may be a syringe actuated by a powered injector.

The step of associating the fluid path set with the fluid control device may include associating a multi-patient set or section with the fluid control device and removably connecting a per-patient set or section with the multi-patient set or section. The multi-patient set and per-patient set may be removably connected by at least one connector. The step of associating the multi-patient set with the fluid control device may include associating a multi-position valve associated with the multi-patient set with a valve actuator associated with the fluid control device. The pump device may be connected with the source of the injection fluid via the multi-patient set.

The method may further include connecting the fluid path set to a source of medical fluid, associating the fluid path set with a pump adapted to deliver the medical fluid to the patient, and actuating the pump to purge air from the portion of the fluid path set associated with the source of medical fluid. The method may further include connecting the fluid path set to a patient catheter.

A hand held control device may be associated with the pump device for controlling the pump device as part of the method.

Additionally, the method may include actuating the fluid control device to permit fluid communication between the pump device and the source of injection fluid, actuating the pump device to draw injection fluid from the source of injection fluid into the pump device, and actuating the pump device to purge air from the fluid path set into the source of injection fluid. The fluid control device and pump device may be controlled according to instructions programmed in a control unit operatively connected to the fluid control device and the pump device. The control device may be a graphical interface display. The first step or act of actuating the pump device includes moving a syringe plunger in a proximal direction within the syringe to draw injection fluid into the syringe from the source of injection fluid. The second step or act of actuating the pump device may include reversing the direction of the syringe plunger in the syringe to purge air from the fluid path set.

The fluid control device may be in the form of a valve actuator adapted to actuate a multi-position valve associated with the fluid path set. The method may include deactuating the pump device and actuating the fluid control device to isolate the pump device from the source of injection fluid.

In another embodiment, the present invention is a method of delivering an injection fluid to a patient, generally including providing a fluid delivery system comprising a source of injection fluid, a pump device, and a fluid path set comprising a fluid control device disposed between the source of injection fluid and the pump device; actuating the fluid control device to prevent fluid communication between the pump device and the source of injection fluid, and to permit fluid communication between the pump device and the patient; actuating the pump device to deliver pressurized injection fluid to the patient; and monitoring a level of injection fluid in a container associated with the fluid path set and in fluid communication with the source of injection fluid. The method may additionally include continuously monitoring the fluid path set for presence of air during the delivery of the pressurized injection fluid.

The method may further include actuating the fluid control device to stop fluid communication between the pump device and the patient at substantially any pressure or flow rate generated by the pump device. The pump device may be a syringe or a peristaltic pump. The step or act of actuating the pump device may include moving a syringe plunger in a distal direction within the syringe to force fluid out of the syringe and into the patient via the fluid path set. The fluid control device may be an automated multi-position valve. The pump device may be actuated by a hand held control device operatively connected to the pump device.

The fluid control device and pump device may be controlled according to instructions programmed in a control unit operatively connected to the fluid control device and the pump device.

The method may further include connecting the fluid path set to a source of medical fluid, and delivering the medical fluid to the patient associating with a pump associated with the fluid control device.

The pump device may be a syringe and the method may further include actuating the fluid control device to permit fluid communication between the syringe and the source of injection fluid, and refilling the syringe with injection fluid from the source of injection fluid. The method may further include actuating the fluid control device to close fluid communication between the pump device and the source of injection fluid and to permit fluid communication between the pump device and the patient, and actuating the pump device to again deliver pressurized injection fluid to the patient. The method may include monitoring a level of injection fluid in a container associated with the fluid path set and in fluid communication with the source of injection fluid.

Furthermore, the pump device may be a syringe, and the method may include actuating the fluid control device to isolate the syringe from the source of injection fluid and the patient, and retracting a syringe plunger in the syringe to reduce fluid pressure in the syringe.

Other details and advantages of the present invention will become clear when reading the following detailed description in conjunction with the accompanying drawings.

BRIEF DESCRIPTION OF THE DRAWINGS

FIG. 7D illustrates a side cross-sectional view of an embodiment of a pressure isolation valve of the present invention in which the valve is in a first, "open" state;

FIG. 7E illustrates a side cross-sectional view of the pressure isolation valve of FIG. 7D in which the valve is in a second, "closed" state;

FIG. 7F illustrates a perspective view of the pressure isolation valve of FIGS. 7D and 7E;

FIG. 8A illustrates an angiographic injection system of the present invention including a manual syringe and a pressure isolation mechanism or valve of the present invention, in which the pressure isolation mechanism is closed to isolate a pressure transducer from the fluid path;

FIG. 8B illustrates the angiographic injection system of FIG. 8A in which the pressure isolation mechanism is open to place the pressure transducer in operative communication with the fluid path;

FIG. 18 is a longitudinal cross sectional view of the first connector member of the connector of FIGS. 16 and 17; and FIG. 19 is a longitudinal cross sectional view of the second connector member of the connector of FIGS. 16 and 17

DETAILED DESCRIPTION OF THE INVENTION

In one aspect, the present invention provides an energy/signal source to generate fluid pressure/flow while also providing to the user tactile and/or audible feedback of the fluid pressure generated, allowing the user to modulate the fluid pressure/flow. The powered injection system of the present invention is capable of providing, for example, both precise low-flow/low-pressure fluid delivery for powered coronary injections and high-flow/high-pressure fluid delivery for ventricle injections.

Figure 2:
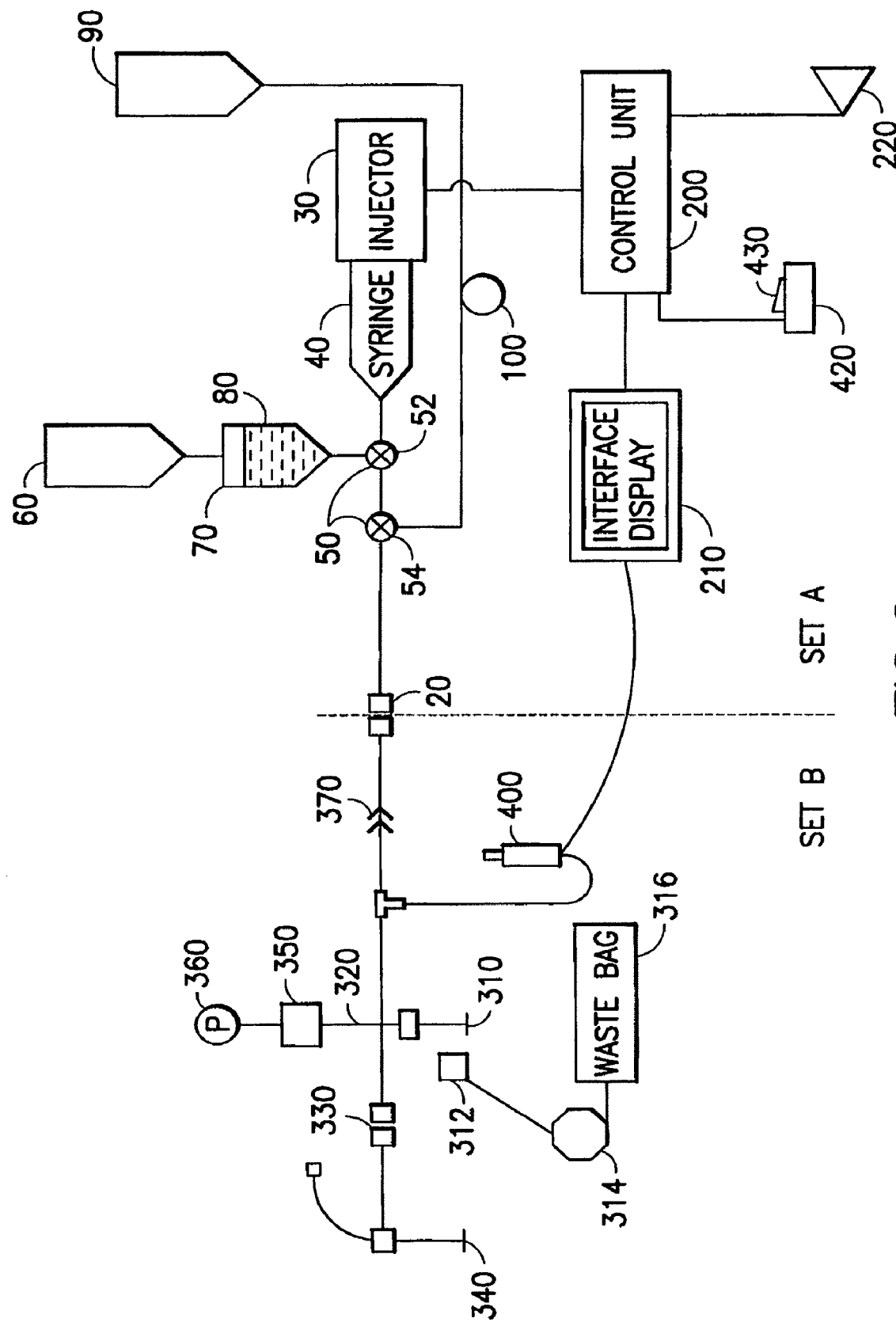
FIG. 2 illustrates one embodiment of an injection system of the present invention.

FIG. 2 illustrates one embodiment of the present invention in which injector system 10 is preferably divided into two sections: a multi-patient section or set A and a per-patient disposable section or set B. Section or set A and section or set B are preferably separated and removably coupled into fluid connection by a high-pressure connector or by a high-pressure, "aseptic" connector 20 such as the septum connector disclosed in U.S. Pat. No. 6,096,011, assigned to the assignee of the present invention, the disclosure of which is incorporated herein by reference. The aseptic coupler or connector of U.S. Pat. No. 6,096,011 is suitable for repeated use (coupling and uncoupling) at relatively high pressures. Aseptic connector 20 preferably maintains a leakproof seal at high pressures after many such uses and can, for example, include a surface that can be disinfected (for example, between patients) by wiping with a suitable disinfectant. Another high-pressure aseptic connector suitable for use in the present invention is disclosed in U.S. patent application Ser. No. 09/553,822, filed on Apr. 21, 2000, assigned to the assignee of the present invention, the disclosure of which is incorporated herein by reference.

Multi-patient set A preferably includes a powered injector 30 which is typically an electromechanical drive system for generating fluid pressure/flow via, for example, a pressurizing chamber such as a syringe 40 as known in the art. Suitable powered injectors and syringes for use in the present invention are disclosed, for example, in PCT Publication No. WO 97/07841 and U.S. Pat. No. 4,677,980, assigned to the assignee of the present invention, the disclosures of which are incorporated herein by reference.

In general, the injector drive is an electromechanical device that creates linear motion acting on a syringe plunger (not shown in FIG. 2) to provide the generation of fluid pressure/flow. A source of injection media 60, for example, a contrast bottle, is in fluid connection with the syringe via, for example, an electromechanical valve actuator assembly 50 for controlling and directing fluid flow by acting upon preferably disposable valves 52 and 54. Valves 52 and 54 are preferably multi-position valves that are fluid wetted. Valves 52 and 54 can alternatively or additionally be manually operated. Contrast bottle or container 60 can be prepackaged contrast media, often distributed in a glass or plastic container with a rubber septum for allowing connections via IV spikes. An interim container or reservoir 70 is preferably placed between contrast bottle 60 and electromechanical valve assembly 50 to provide an air gap in the fluid path to enable purging of air from the system and to allow level detection of contrast source 60 which helps to prevent reintroduction of air once purged. Interim reservoir 70 can operate in conjunction with a contrast level detection system as described in further detail below. A contrast level detector 80 can, for example, include one or more electrical, optical, ultrasound, or mechanical sensors that detect the presence of fluid at a certain level in interim reservoir 70.

Further protection against injection of air into a patient can be provided by variety of mechanisms for detection of air in the fluid path or stream. For example, ultrasonic bubble detection can be used to detect the presence of air in the fluid path. Likewise, backlighting can facilitate air bubble detection by the operator. In the backlighting method of bubble detection, the injector side of the fluid path is illuminated to increase visualization of the fluid path, fluid presence and air presence.

At least one source 90 of another fluid, typically saline or other suitable medium, can also be provided. Additional fluid sources, such as therapeutic fluids, can also be provided. Additional fluid sources such as saline supply 90 are preferably in operative or fluid connection with a pressurizing mechanism such as a powered injector or a peristaltic pump 100. In FIG. 2, peristaltic pump 100 in operative connection with the saline source 90 is in fluid connection with the fluid path of injector 30 via electromechanical valve actuator assembly 50.

A controller unit 200 provides power to injector 30 and to peristaltic pump 100 in a controlled manner. Controller unit 200 provides communication between the various system components. A graphical user interface display 210 is preferably provided in connection with controller unit 200 to display information to the user and to enable the user to set and adjust device parameters. An audible feedback source 220 can be provided, for example, to provide feedback to the user of the rate of flow provided by injector 30. For example, a sound can increase in pitch, volume and/or frequency as flow rate is increased.

Per-patient disposable set B includes fluid wetted components of the fluid delivery path. Per-patient disposable set B preferably includes a waste port 310, for example through which patient blood can be drawn, a pressure measurement port 320, and an interface 330 to a catheter 340, for example, a connector such as a standard luer connector. Waste port 310 can, for example, include a manually activated or automated valve to allow discharge of unwanted fluid and connection of, for example, manually operated syringes. Moreover, a powered aspiration mechanism, for example a peristaltic pump 314 connected via tubing to a waste bag 316, can be connected to waste port 310 via, for example, a standard connector 312, to aspirate fluid from the system as well as to draw blood from the patient. Drawing fluid from the system and blood from the patient into a waste bag 316 assists in eliminating air from the fluid delivery system.

Figure 3:
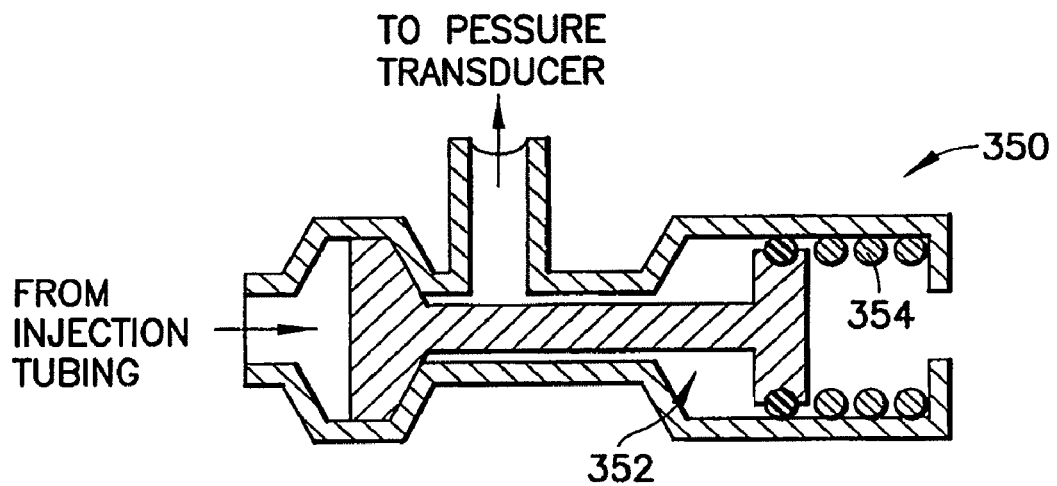
FIG. 3 illustrates an embodiment of a pressure activated isolator assembly of the present invention.

Pressure port 320 preferably includes a pressure-activated isolator 350 for pressure transducer isolation as, for example, illustrated in FIG. 3. Pressure-activated isolator 350 is a fluid activated assembly that is located in line with the injection flow. In the embodiment of FIG. 3, a valve 352 within the assembly isolates pressure transducer 360 by shutting off during high-pressure injections. A biasing member or mechanism such as a spring 354 returns valve 352 to its original open position when the injector system is not injecting at high pressure, thus opening the fluid path to pressure transducer 360. In the embodiment of FIGS. 2 and 3, pressure-activated isolator 350 transitions to a closed position to isolate only pressure transducer 360, which is not in fluid connection with contrast source 60 or saline source 90 other than through pressure-activated isolator 350. Pressure transducer 360 can, for example, be located near the patient to substantially reduce or remove pressure signal dampening resulting from intervening tubing, fluid and system components and thereby improve accuracy as compared to other pressure measurement systems currently used in angiographic procedures. Preferably, pressure transducer 360 is separated by a minimum, for example by no more than approximately three feet, of tubing from the patient/catheter connector. Because of the multi-patient nature of set A, the pressure transducer assembly and the remainder of per-patient disposable set B are preferably located downstream of a double check valve 370 to provide continuous measurements. As such, a pressure isolation mechanism such as described above is required to isolate pressure transducer 360 from high pressure during power injection.

Figure 4:
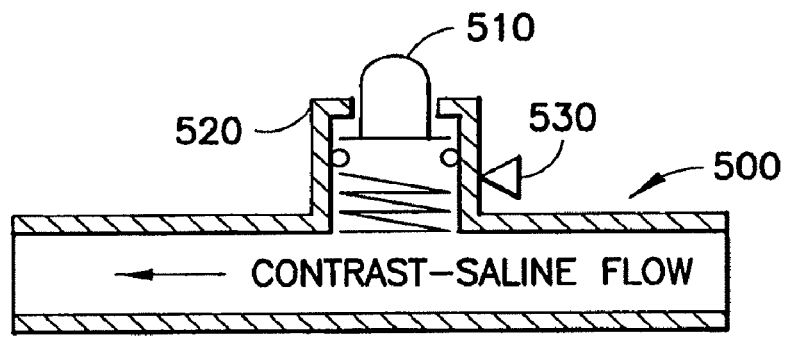
FIG. 4 illustrates an embodiment of a handheld controller or hand piece of the present invention.
Figure 5:
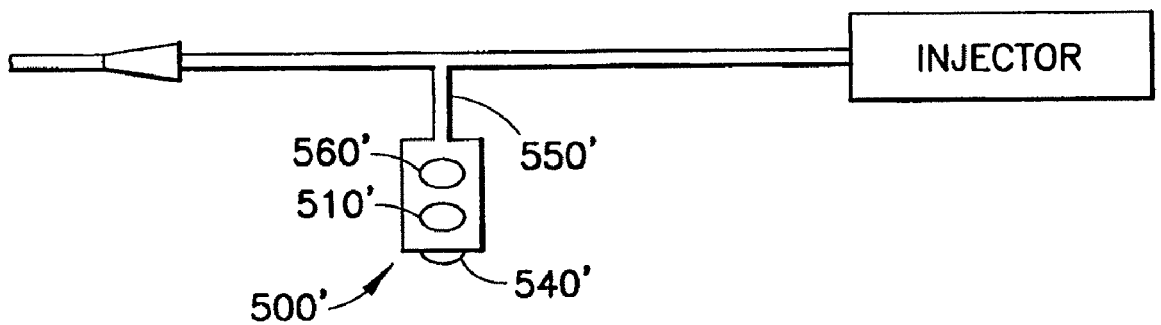
FIG. 5 illustrates another embodiment of a handheld controller of the present invention in which the handheld controller is connected to the fluid path via a "T" connection.

The system also includes a manually operated, for example, a handheld or hand operated, control 400 that can, for example, generate or process a control signal that is electrical, mechanical, pneumatic, optical, radio frequency, audible or any combination thereof to effect control of injector 30 and preferably to also effect control of peristaltic pump 100. Handheld control 400 also preferably provides feedback, for example, tactile, visual, audible, etc., of the injected fluid pressure and flow to the operator. Handheld control 400 preferably provides at least one type of feedback, for example, tactile feedback. In the embodiments of FIGS. 2, 4 and 5, the handheld control or hand piece is in operative communication with the fluid flow and allows the user to feel the pressure in the fluid path line. Preferably, an electrical switch allows the user to turn on/off and modulate the fluid/flow pressure of the system for low-pressure/low-flow coronary injections only. High-pressure injection is activated, for example, using either display 210 or a separate, second control on the handheld control. The handheld control thus provides pressure feedback to the user while controlling the low-pressure/low-flow coronary injections.

The handheld controls of the present invention can, for example, include a fluid path containment chamber in which a movable element is able to travel a pre-determined distance. The moveable element is preferably in direct contact with the fluid path and is affected by fluid flow and pressure. The movable element incorporates a mechanism to process a signal, which can be used to control the fluid pressure/flow source remotely. The handheld device is capable of being used with a signal processor related to the movement of the moveable element as known in the art.

In one embodiment of the present invention, a handheld control device 500 incorporates a moveable piston 510 slideably disposed within a chamber 520 in a direction generally perpendicular to the direction of fluid flow as illustrated in FIG. 4. Chamber 520 and piston 510 can be directly in the fluid path or can be spaced from the fluid path by a length of tubing (see, for example, FIG. 5). Handheld device 500 allows moveable piston 510 to be positioned under one finger while device 500 is held in the hand. Piston 510 preferably incorporates a switch 530, that when compressed, controls the fluid flow generated by an external fluid pressure/flow source, for example, injector 30. Upon generation of the pressure, piston 510 is displaced by increased pressure, which is detectable by the operator. Further compression of piston 510 by the operator preferably increases the signal to the fluid flow/pressure generator, resulting in an increase in the pressure/flow and an increased pressure on piston 510, which is felt by the operator. Backpressure or tubing occlusion causes increased pressure in the system, upward movement of piston 510 and tactile feedback to the operator, thereby alerting the operator to potential problems in the injection procedure. The system can also provide audible and/or visual feedback of the flow rate via, for example, user display 210 that is preferably controlled by the position of piston 510.

As illustrated in FIG. 5, a handheld control 500' can be connected in a "T" 550' off of the main line for more flexibility. A purge valve 540' can be located at the end of handheld control 500' for air elimination during system purge. Air can also be purged from the handheld control 500' before it is connected to the fluid path. FIG. 5 also illustrates a second switch 560' for initiation of a high pressure injection. An additional switch or switches can also be provided to, for example, control delivery of saline.

Figure 6A:
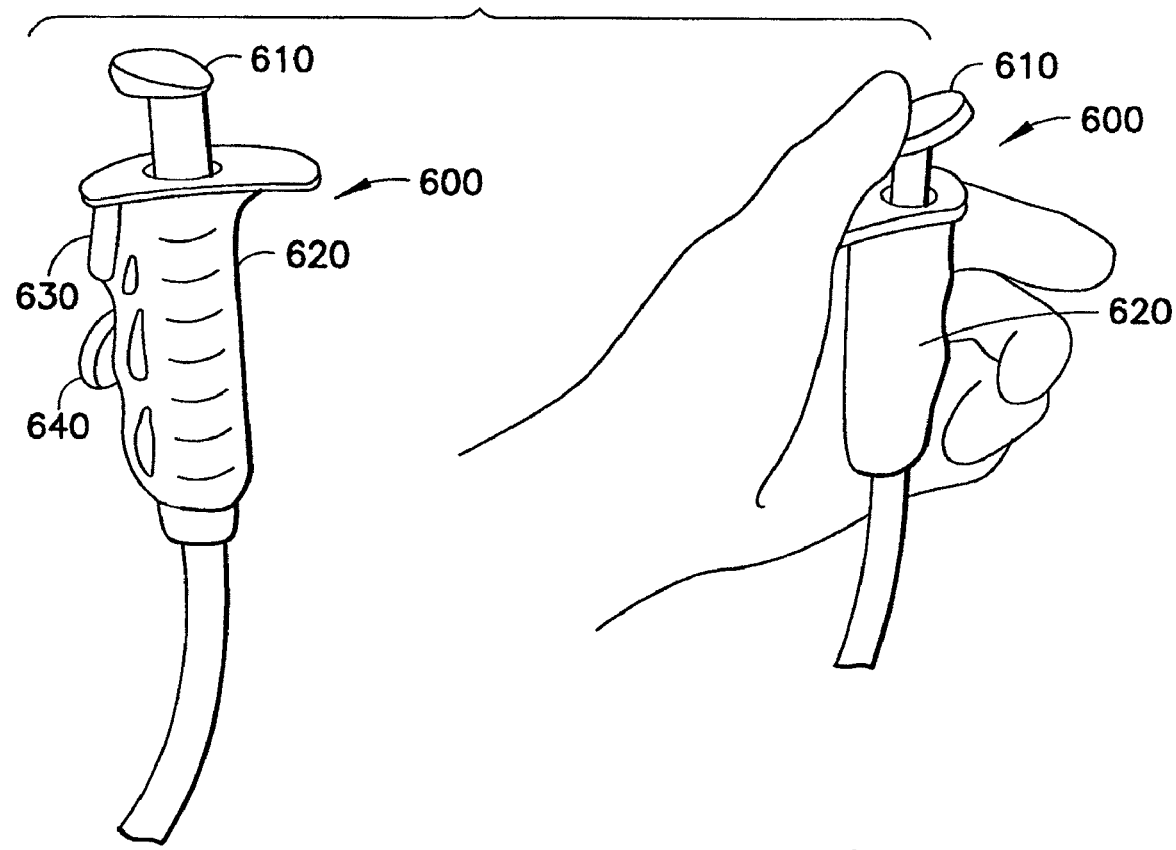
FIG. 6A illustrates another embodiment of a handheld controller of the present invention including a control switch for pressure feedback in low pressure injection, a switch for high pressure injection, and a switch for saline injection.
Figure 6B:
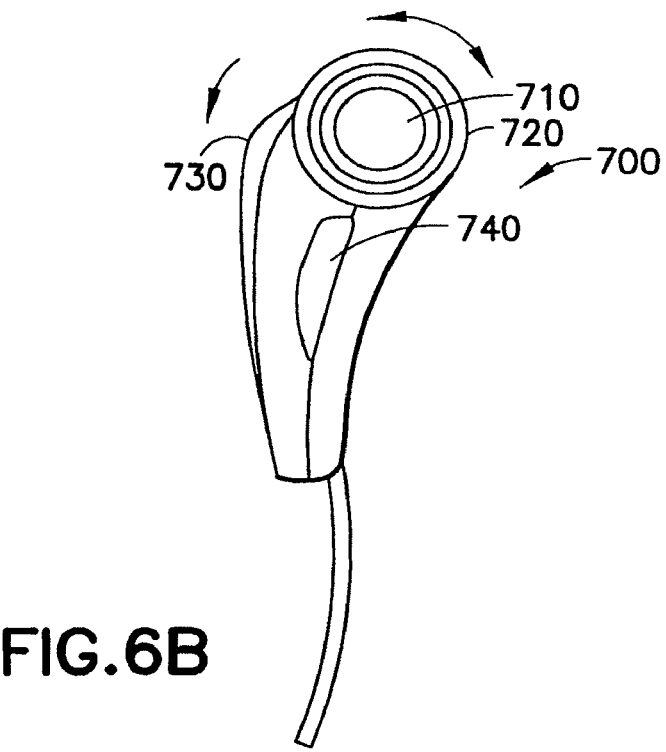
FIG. 6B illustrates another embodiment of a handheld controller of the present invention, which is wearable on a finger of the user.

FIGS. 6A and 6B illustrate other, ergonomic handheld controls. Handheld control 600 of FIG. 6A includes a chamber 620 that can be in fluid connection with the injection system fluid path as described above. A low pressure control switch 610 similar in operation to piston 510 is slideably disposed within chamber 620 to control low-pressure injections of contrast. Chamber 620 can, for example, be formed to conform to the hand of the user. A switch 630 to begin a high pressure injection via injector 30 is provided on handheld control 600. Also, a switch 640 to control delivery of saline is provided on handheld control 600.

FIG. 6B illustrates an embodiment of a finger-wearable handheld control 700. In that regard, a finger of the user's hand passes through passage 710 in control 700 while control 700 is held in the user's hand. A rotating switch 720 controls low-pressure injection. A high pressure injection switch 730 and a saline switch 740 are also provided.

System 10 (FIG. 2) can also include a manually operated foot controller 420 including one or more actuators 430 in communication with controller 200. Foot controller 420 can, for example, be used to control flow through system 10 in conjunction with or independently of handheld controller 400.

Another embodiment of an injector system 800 is illustrated in FIGS. 7A through 7H. In this embodiment, referring primarily to FIGS. 7A and 7G, a fluid control module 810 is in operative connection with a powered injector 830 to which a syringe 840 is connected as described above. Syringe 840 is in fluid connection with an automated valve 852 of fluid control module 810, which is also in fluid connection with a source of contrast 860 via an intermediate drip chamber 870 (see FIG. 7A). Drip chamber 870 preferably includes a fluid level sensing mechanism 880. A preferably automated valve/stopcock 852 such as known in the art is also in fluid connection with a first, inlet port of a lumen 954 of a pressure isolation valve 950 (see, for example, FIGS. 7D through 7F). Valve 852 prevents saline and/or contaminated fluids from entering syringe 840 and enables the operator to stop flow of injection fluid (for example, contrast) from syringe 840 quickly at any pressure or flow rate. This ability to substantially immediately stop flow of injection fluid at any pressure and flow rate substantially removes the effects of system compliance and enables delivery of a "sharp" bolus. An air column detector 856 can be placed in line between stopcock 852 and pressure isolation valve 950.

Fluid control module 810 further includes a source of saline 890 in fluid connection with a peristaltic pump 900 via an intervening drip chamber 910. Drip chamber 910 preferably includes a fluid level sensing mechanism 920. Peristaltic pump 900 is in fluid connection with a preferably automated valve/stopcock 854, which is in fluid connection with pressure isolation valve 950. In addition to controlling flow of saline, valve 854 prevents contaminated fluids from reaching peristaltic pump 900 and saline source 890. An air column detector 858 can be placed in line between stopcock 854 and pressure isolation valve 950.

A controller 970 and a display 974 (see FIG. 7A) are also in operative connection with injector 830 as described above. Furthermore, handheld controller 1000 is in operative connection with injector 830 and thereby with fluid control module 810. In the embodiment of FIGS. 7A through 7C and FIG. 7G, handheld controller 1000 does not provide tactile feedback of system pressure to the operator. However, a handheld controller providing such tactile feedback (for example, handheld controller 600) can readily be used in connection with system 800. Moreover, a foot controller as described above can also be provided.

Figure 7A:
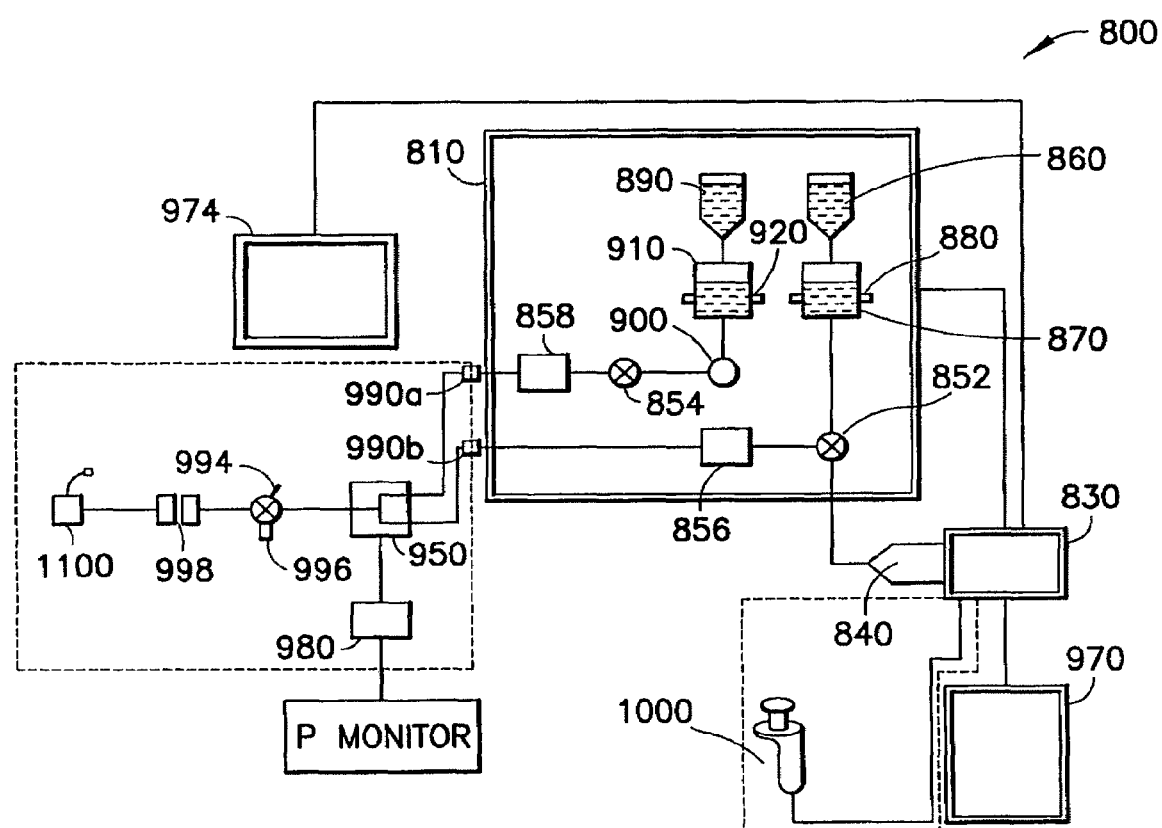
FIG. 7A illustrates a schematic representation of another embodiment of an injection system of the present invention.
Figure 7B:
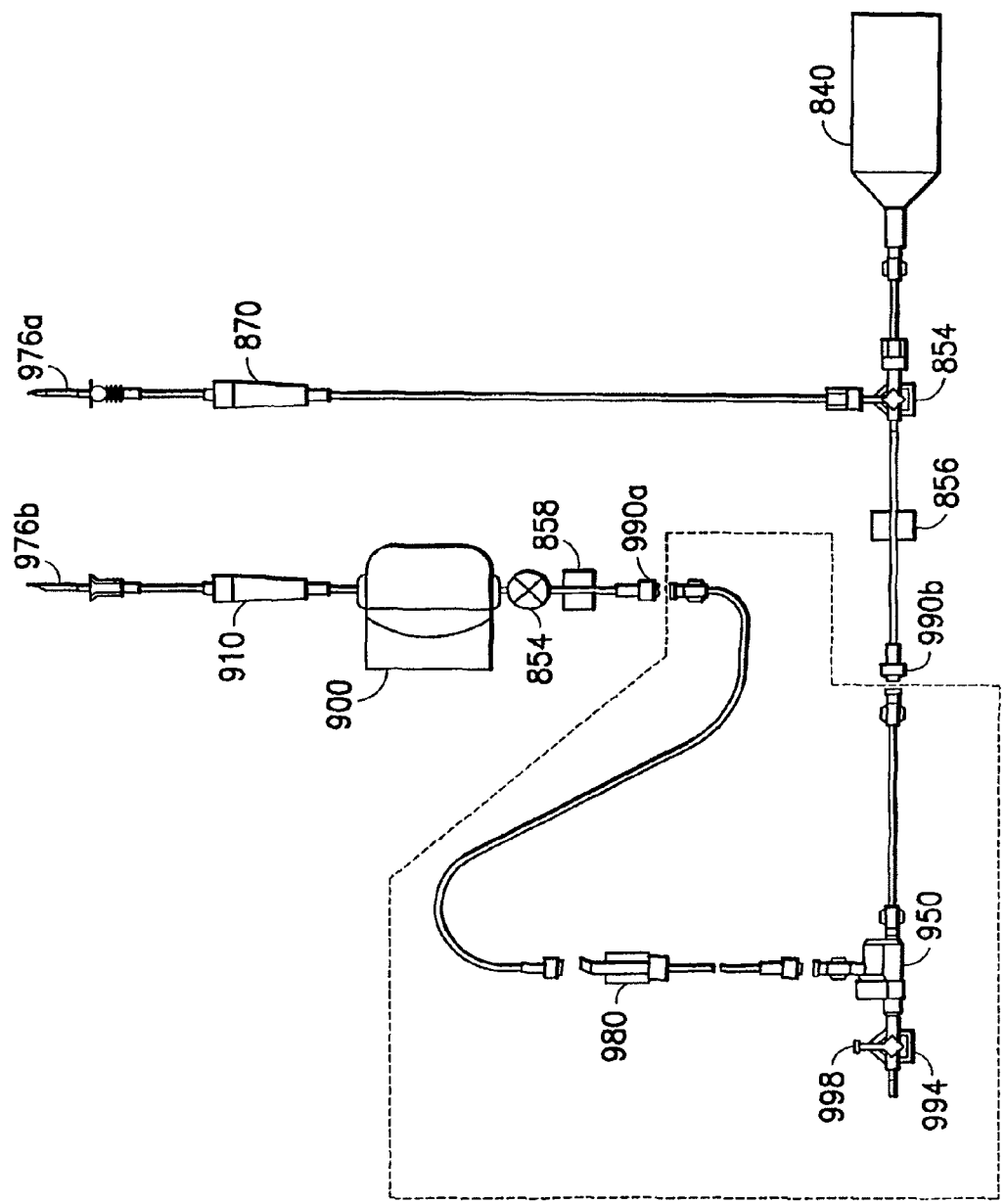
FIG. 7B illustrates a side view of an embodiment of a portion of the injection system of FIG. 7A in which a pressure transducer is in the fluid path.
Figure 7C:
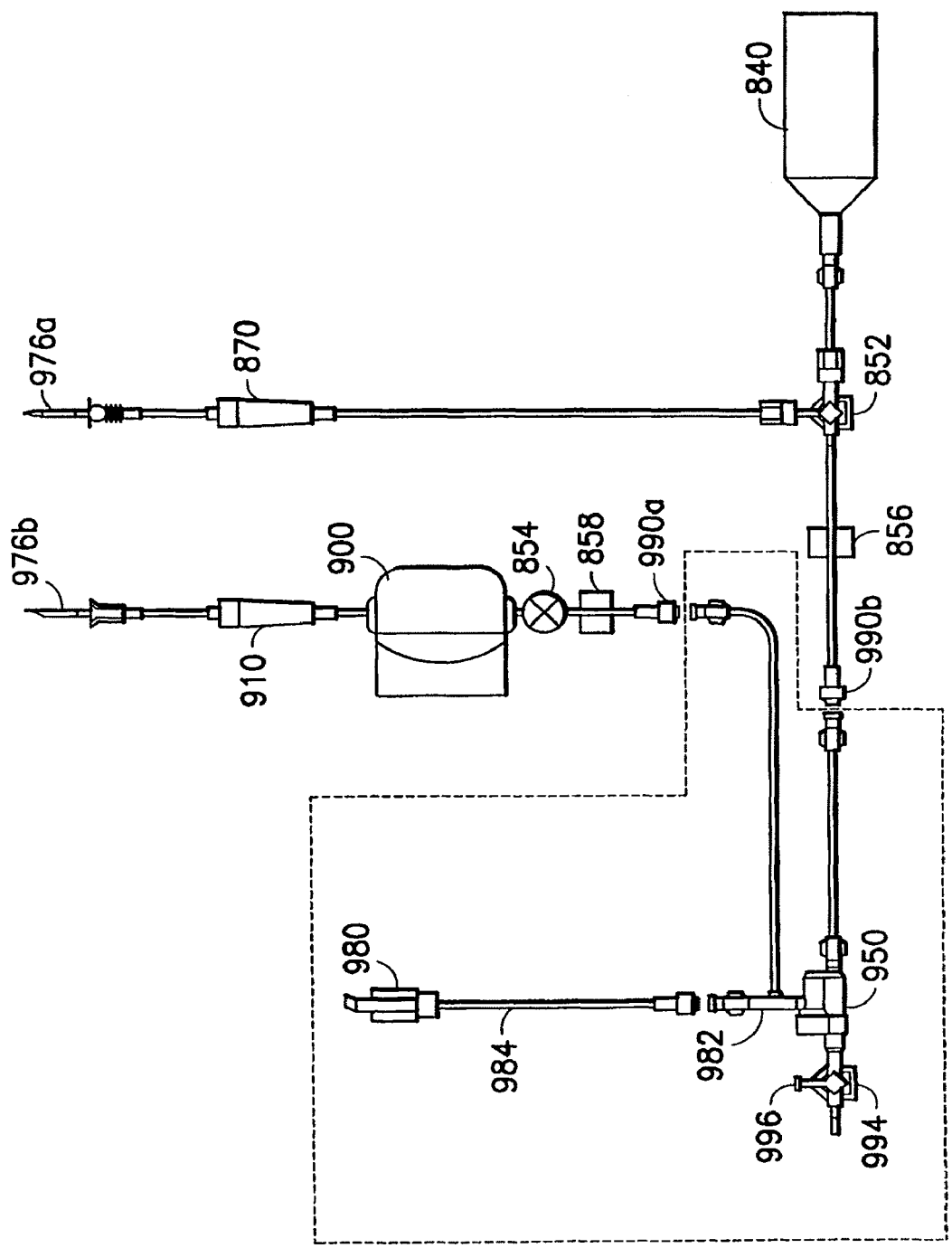
FIG. 7C illustrates a side view of an embodiment of a portion of the injection system of FIG. 7A in which a pressure transducer is separated from the fluid path by a T-connector and a length of tubing.

In general, the preferably per-patient disposable portion or set of system 800 is illustrated within dashed lines in FIGS. 7A, 7B, and 7C. Two connectors 990a and 990b (which are preferably aseptic connectors as described above) are used to connect the multi-patient fluid path set with the per-patient fluid path set. Use of two separate/parallel fluid lines and two separate connectors to connect the multi-patient set with the per-patient disposable set affords a number of benefits over current angiographic injection systems including decreased contrast waste and avoidance of injecting potentially hazardous amounts of contrast into the patient during saline purges. Moreover, system 800 facilitates close placement of pressure transducer 980 to the patient, improving measurement accuracy as compared to currently available systems. Although handheld controller 1000 in the embodiments of FIGS. 7A through 7H is not in direct connection with the fluid path, it is preferably disposable because of contamination with bodily fluids that typically occurs from operator handling thereof.

Lumen 954, via a second, outlet port thereof, of pressure isolation valve 950 is preferably in fluid connection with an automated or manual valve/stopcock 994, which preferably includes a waste port 996 as described above. Catheter 1100 is preferably connected via a rotating luer connection 998.

FIG. 7B illustrates a portion of a fluid path set for use in system 800 of FIG. 7A in which a pressure transducer 980 is directly in the saline fluid path. FIG. 7C illustrates a fluid path set for use in system 800 of FIG. 7A in which pressure transducer 980 is separated from the saline fluid path by a "T" connector 982 and a length of tubing 984. In the embodiments of FIGS. 7B and 7C, spikes 976a and 976b are used to connect to contrast source 860 and saline source 890, respectively. In general, standard luer connections are used to connect most of the components of system 800. In FIGS. 7B and 7C several of these luer connections are illustrated in a disconnected state. Alternatively, one or more of the illustrated connections can, for example, be non-luer or bonded connections.

One embodiment of a pressure isolation valve 950 is illustrated in FIGS. 7D through 7F. Pressure isolation valve 950 includes a housing 952 with a high pressure lumen 954, through which fluid passes under pressure. Pressure isolation valve 950 also includes a port 956 to which pressure transducer 980 and saline source 890 are connected. A piston 958 acts to isolate pressure transducer 980 once a given pressure is reached in lumen 954 of pressure isolation valve 950. In an "open" or rest state, as shown in FIG. 7D, there is hydraulic or fluid communication between lumen 954, including catheter 1100 and injector 840 connected thereto, and isolation port 956, including pressure transducer 980 and the saline fluid path connected thereto.

Preferably, the clearances and apertures within pressure isolation valve 950 are sufficiently generous to transmit changes in pressure that normally occur during normal heart function quickly, as to not damp or attenuate the signal. The pressure effect on piston 958 of the flow of injection fluid from syringe 840 through lumen 954 is illustrated with dashed arrows in FIG. 7D while the flow of saline through pressure isolation mechanism 950 is illustrated with solid arrows. When the pressure within lumen 954 increases during an injection, piston 958 responds by moving to the right in the orientation of FIGS. 7D and 7E, compressing a spring 960 until a seal portion 962 at the left end of piston 958 contacts a sealing seat 964 as illustrated in FIG. 7E. At this point, lumen or port 956 is isolated from lumen 954 and any additional increase in pressure acts to increase or improve the effectiveness of the seal 962. When the pressure within lumen 954 subsides, spring 960 reopens pressure isolation valve 950 by pushing piston 958 to the left. In one embodiment, fluid does not flow through port 956. In this embodiment, pressure isolation valve 950 only isolates the tubing and devices distal to port 956 from high pressure and does not control flow.

Pressure isolation valve 950 of the present invention is suited for use in any medical fluid path in which it is desirable to automatically isolate a pressure sensitive fluid path component, for example, a pressure transducer or other fluid path component or fluid pathway from pressures above a certain predetermined pressure. The pressure at which pressure isolation valve 950 isolates port 956 from lumen 954 can be readily and easily adjusted through variation of a number of variables as known to those skilled in the art, including, for example, various valve dimensions and the properties of spring 960, for example, the force constant thereof. Connection of pressure isolation valve 950 into any fluid path is quite simple. In that regard, lumen 954 is simply placed in the fluid path via connection of ports 954*a* and 954*b* to disconnected or open ends of the fluid path without any other change to the fluid path or to pressure isolation valve 950. Standard connections such as luer connections as known in the medical arts can be used to connect lumen 954 to the fluid path. Valve 950 can also be incorporated into or embedded within other devices such as a manifold, a pressure transducer or a connector.

In an alternative to mechanical operation of valve piston 958 as described above, valve piston 958 can also be controlled via an electromechanical mechanism. For example, a pressure sensor such as pressure sensor or transducer 980 (see, for example, FIG. 7B) can send a signal to an actuator, for example, in the operative position of and functioning in a similar manner to spring 960 as known in the control art to control the position of valve piston 958 and thereby control fluid flow through port 956.

Figure 1:
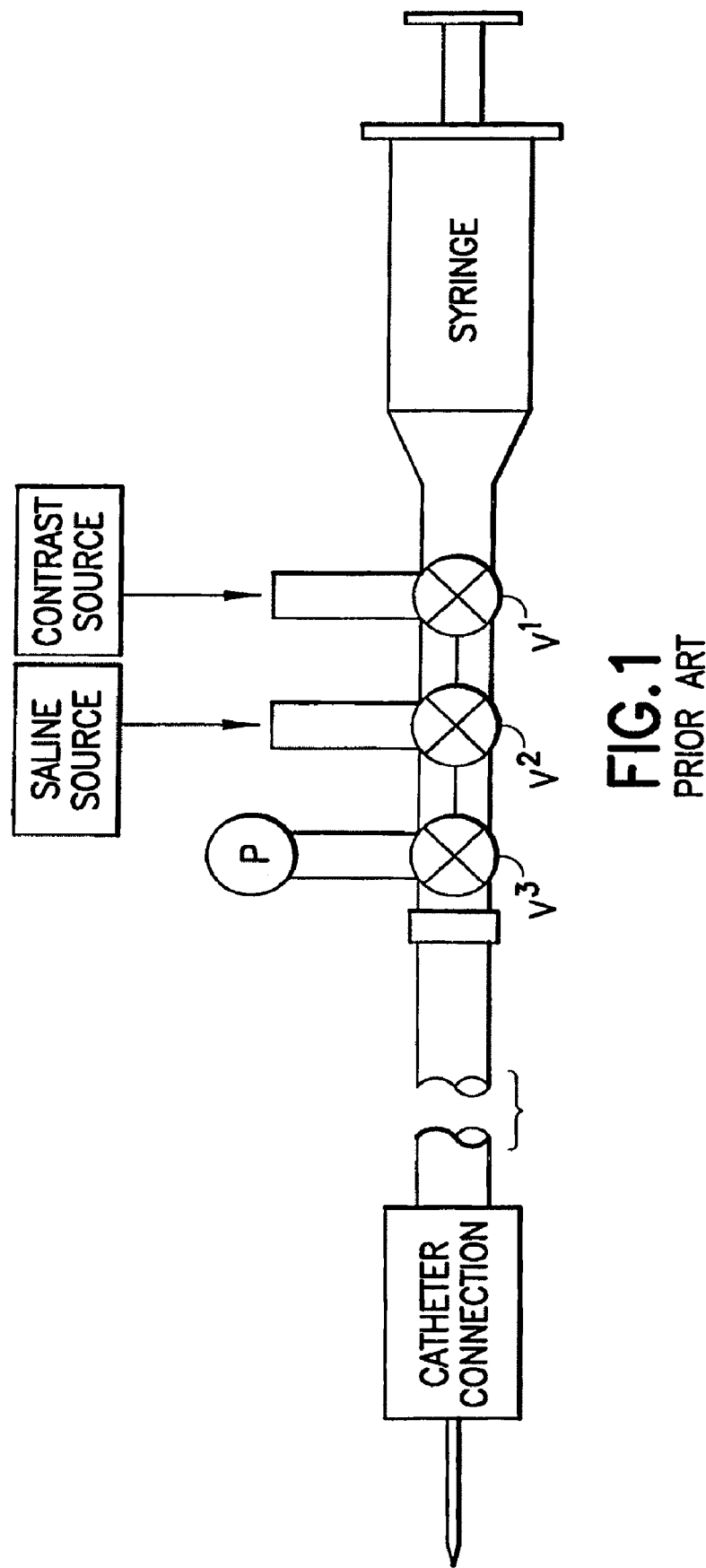
FIG. 1 illustrates an embodiment of a known manual injector system.

FIGS. 8A and 8B illustrate use of pressure isolation valve 950 to automatically isolate a pressure transducer P from increased pressures in a manual injection system such as set forth in FIG. 1. Valve $V^3$, used for manual isolation of a pressure transducer as described previously, can be removed from the fluid path or retained therein. As illustrated in FIG. 8A, application of a force F to the syringe plunger extension causes pressurized fluid to flow from the syringe into the fluid path. The elevated pressure causes pressure within lumen 954 to increase. As discussed previously in connection with FIGS. 7D and 7E, piston 958 responds by moving to the right in the orientation of FIGS. 8A and 8B, compressing spring 960 until seal portion 962 contacts sealing seat 964 as illustrated in FIG. 8A. At this point, port 956 and pressure transducer P are isolated from lumen 954 and the remainder of the fluid path. As illustrated in FIG. 8B, when the syringe in inactivated, the pressure within lumen 954 subsides, and spring 960 reopens pressure isolation valve 950 by pushing piston 958 to the left.

Incorporation of pressure isolation valve 950 into the fluid path of FIGS. 8A and 8B provides a substantial improvement compared to the injection system of FIG. 1. For example, it is taxing and difficult for a physician or other operator using the system of FIG. 1 to operate each of valves $V^1$, $V^2$ and $V^3$. Operators often either forget to close valve $V^3$ during injections, thereby resulting in damaged pressure transducers or fail to reopen the valves post-injection preventing proper or timely patient monitoring. Injection procedures are greatly facilitated in the system of FIGS. 8A and 8B by automation of the isolation of pressure transducer P at elevated pressures.

As discussed above, saline is used occasionally during routine catheterization procedures. For example, controls 1020*a* or 1020*b* on handheld control 1000 can send a signal to control the flow of saline. For patient safety, it is desirable to introduce the saline close to the proximal end of catheter 1000 so the amount of contrast purged ahead of the saline is minimized during a saline injection. Once again, the parallel line configuration of the contrast delivery and saline deliver fluid paths of present invention assist in preventing such undesirable injections.

Since the required saline flow rates are low and the viscosity of saline is much lower than the viscosity of contrast, the pressures required to force saline through catheter 1100 are much less than that of contrast. By protecting the saline line from the high pressures required for contrast injection, additional system compliance is avoided and the saline line does not need to be made of the same high-pressure line as the contrast. Protection of the saline line from high pressure is accomplished by connecting the saline line to port 956 of pressure isolation valve 950 to introduce the saline flow as illustrated with solid arrows in FIG. 7D. In this embodiment, port 956 is normally open, permitting the flow of saline therethrough, when required, as well as the monitoring of the patient blood pressure. During a high-pressure injection, pressure isolation valve 950 functions as described above and protects pressure transducer 980 and the low-pressure saline line from the high contrast injection pressures.

The elevation of catheter 1100 often changes during the course of an injection procedure, for example, as the patient is raised or lowered. Such changes in elevation of catheter 1100 can result in erroneous blood pressure readings by pressure transducer 980. Therefore, pressure transducer 980 is preferably positioned such that it changes elevation with catheter 1100 and is not dependent upon the position of the injection system, including the position of injector 830.

Figure 7G:
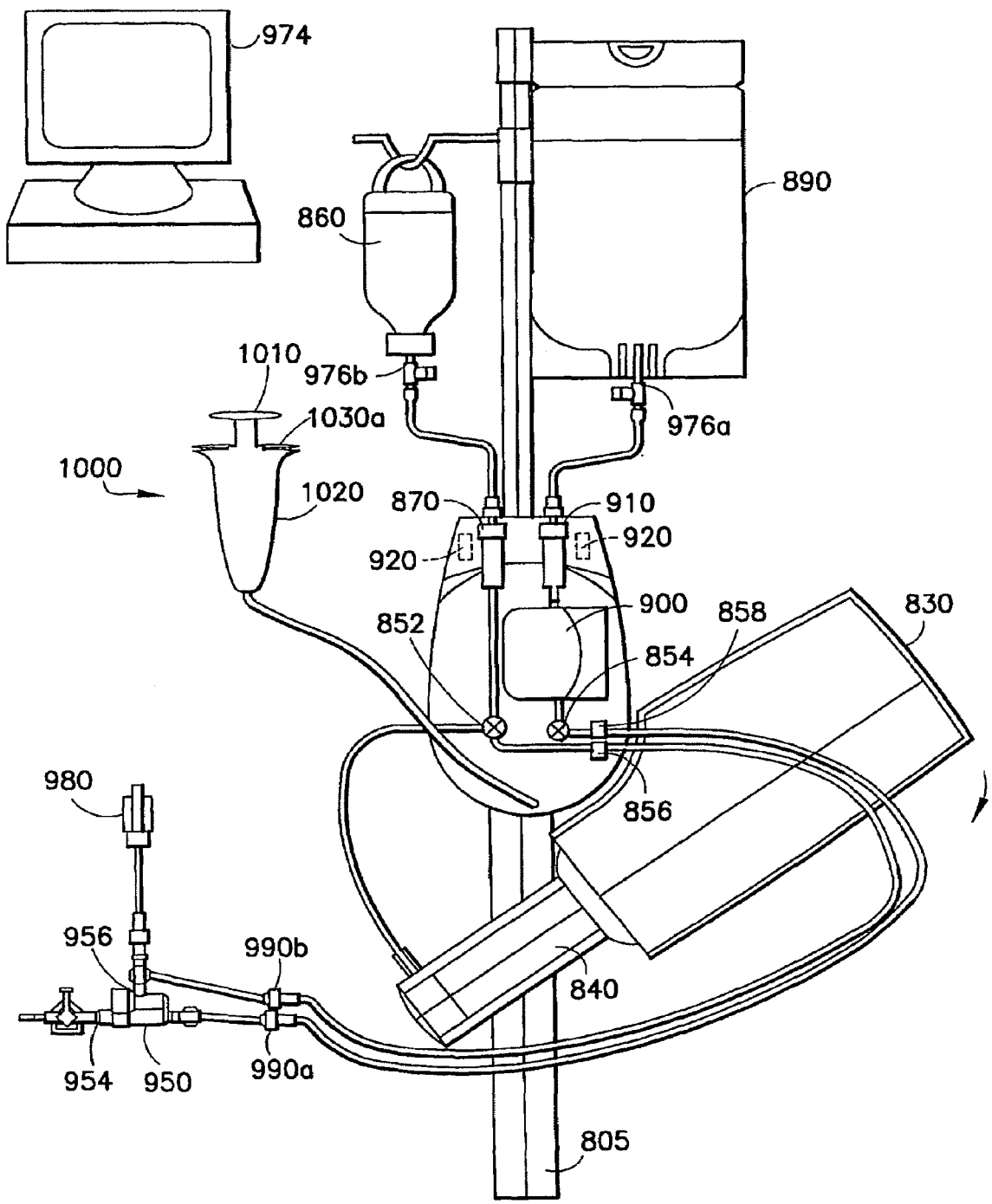
FIG. 7G illustrates a front view of the injection system of FIG. 7A.
Figure 7H:
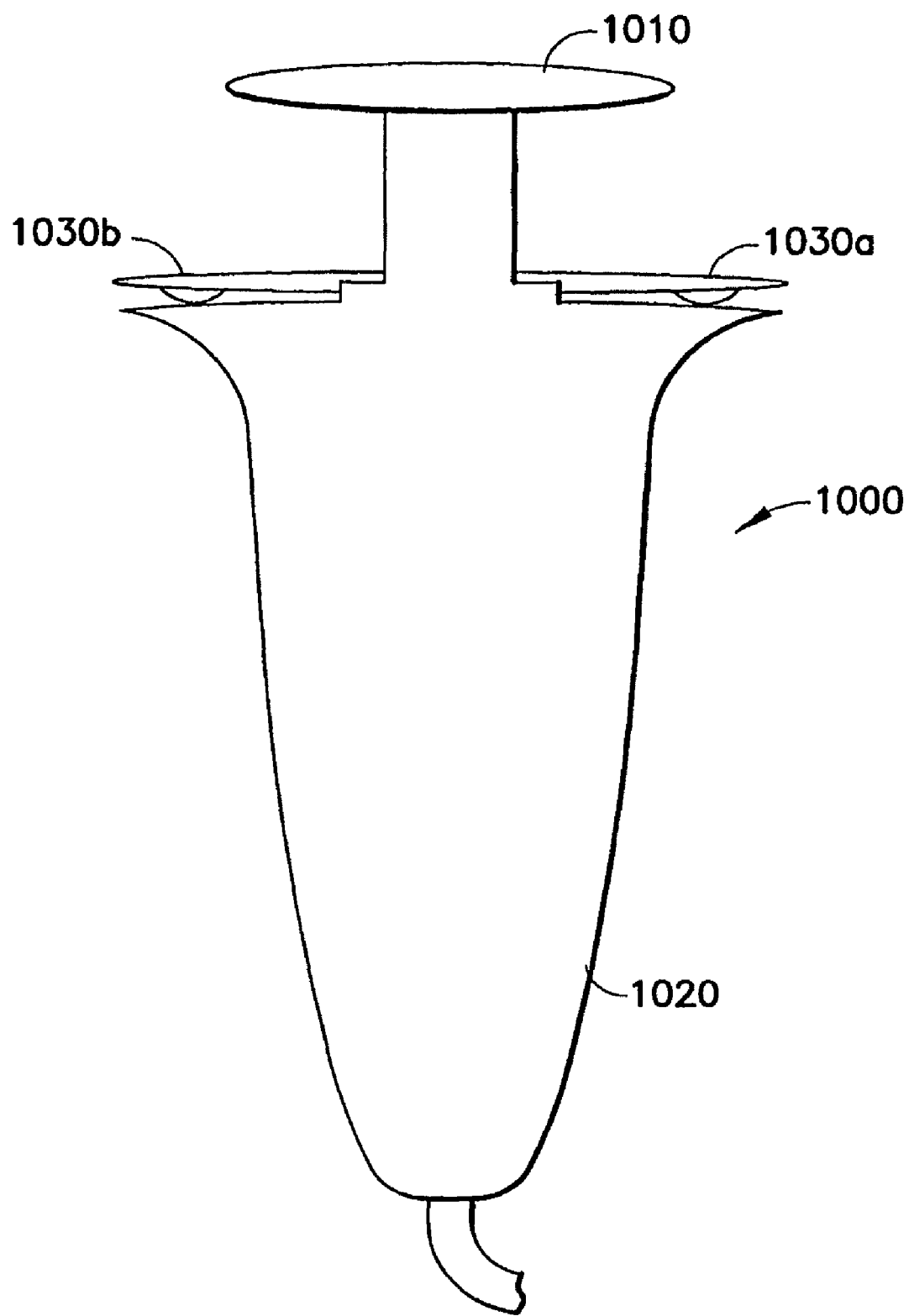
FIG. 7H illustrates a front view of the handheld controller of the injection system of FIG. 7A.

In one embodiment illustrated in FIGS. 7G and 7H, handheld controller 1000 included a plunger or stem control 1010 that, when in a first/low pressure mode, is depressed by the operator to control the flow of contrast from syringe 840. The farther plunger 1010 is depressed, the greater the flow rate via, for example, a potentiometer such as a linear potentiometer within housing 1020 of controller 1000. In this embodiment, the operator can use graphical user interface display 974 to change the mode of plunger 1010 to a second mode in which it causes injector 830 to initiate a high pressure injection as preprogrammed by the operator. In this second/high pressure mode, the operator maintains plunger 1010 in a depressed state to continue the injection. Preferably, if plunger 1010 is released, the high-pressure injection is terminated substantially immediately, for example, by control of valve 852. Handheld controller 1000 also includes at least one switch to control saline flow in system 800. In the embodiment of FIG. 7H, handheld controller 1000 includes two saline switches 1030*a* and 1030*b* on either side of plunger 1010 for ease of access by the operator. In this embodiment, switches 1030*a* and 1030*b* include resilient cantilevered members 1032*a* and 1032*b*, respectively, which are depressed by the operator to deliver saline through system 800. Preferably, one of switches 1030*a* or 1030*b* must be maintained in a depressed state by the operator to continue delivery of saline. If the depressed switch is released, saline flow is preferably stopped substantially immediately, for example, via control of valve 854.

As illustrated in FIG. 7G, many of the components of system 800 can be supported on a mobile stand 805. Injector 830 is preferably rotatable about stand 805 as indicated by the arrow of FIG. 7G. In one embodiment of system 800 of FIGS. 7G and 7H: stopcocks were obtained from Medical Associates Network, Inc., a distributor for Elcam Plastic, under product number 565302; spikes were obtained from Qosina under product numbers 23202 and 23207, tubing was obtained from Merit Medical under product numbers DCT-100 and DCT-148; connectors were obtained from Merit Medical under product number 102101003, a rotating hub was obtained from Medical Associates Network, Inc., a distributor for Elcam Plastic, under product number 565310; a peristaltic pump from Watson-Marlow was obtained having a product number of 133.4451.THF; and fluid level sensor from Omron were obtained under product number EESPX613.

The following describes a typical use scenario of injection systems of the present invention and assumes that all fluid path components are assembled/connected and located in their proper position, including contrast and saline containers.

Typically, the first step in an injection procedure is replacing air in the fluid path with fluid. By operator initiation and machine control, the powered injector causes the syringe plunger to move rearward toward the powered injector, thereby creating a negative pressure at the connection point to a control valve in proximity to the contrast interim container. The control valve is positioned to allow fluid flow from the contrast bottle, into the interim container and into the syringe. Upon drawing a predetermined amount of contrast into the syringe, the injector drive preferably reverses direction creating a positive pressure and fluid movement in the direction of the contrast container or the catheter, which is not connected to a patient, to drive any entrapped air out of the fluid path into an "air gap" established in the interim container or through the catheter. Air is further preferably initially purged from the system during start-up by, for example, distributing a fluid such as saline through the fluid path, sometimes referred to as "priming". The system is preferably maintained air-free during an injection procedure. Priming is preferably done once per patient or once per multi-patient, depending on disposable fluid path configuration.

The system can include, for example, "contrast low" level (need for refill) and "stop filling" limit sensors on the interim reservoir as described above to help ensure that air is not aspirated into the contrast syringe during a fill cycle. An ultrasonic air column sensor or sensors and/or other types of sensors can also be included downstream of the injector to detect air gaps within the line as a secondary safety sensor.

By operator initiation and machine control, a second fluid pump connected to a bulk source of saline, typically a pre-filled bag, provides fluid flow in the direction of patient catheter. Enough saline is preferably pumped throughout disposable set to achieve elimination of all visible air during priming. Using the saline priming feature, a handheld controller that is in fluid connection with the fluid path to provide tactile feedback as described previously can, for example, be purged of air by opening an integral bleed valve. After priming is complete the bleed valve is closed.

Once the system is properly set up and primed, it can be connected to the patient via the catheter. The system preferably has a range of parameters for flow, pressure, variable flow, alarms and performance limits as known in the art.

To deliver contrast at low flow and low pressure, for example, to the coronary arteries, depressing a first button, piston or other controller on the handheld controller initiates flow of contrast and in some embodiments provides feedback, for example, tactile and/or audible feedback. Further depressing the button on the hand controller preferably increases the flow rate of contrast. If at any time the button is released, the fluid flow preferably stops and any feedback ends. This "dead-man" operability can be provided, for example, by biasing, for example spring loading, the first control or actuator toward the off position. The minimum and maximum flow are preferably established by the parameters set using a graphical user interface on the display.

To deliver contrast at high flow and high pressure, for example, to the left ventricle, a separate switch or second actuator/controller on the hand control is preferably depressed. Alternatively, a second mode of the first actuator/controller can be entered to control high pressure flow. In embodiments in which the handheld control provides tactile feedback during low-pressure injection, preferably no such tactile feedback is provided during high pressure flow. However, other feedback such as an audible tone feedback different than any audible tone provided during the low-pressure mode can be provided. The high-pressure/high-flow function is preferably first input/selected from the parameters input/set using the graphical user interface on the display. The high-flow and high-pressure injection is preferably preprogrammed and the flow cannot be varied. As discussed above, any direct, tactile feedback is preferably eliminated, as the pressure is often over 1000 psi. If at any time the second button is released, the injection preferably stops.

To deliver saline, a second or third switch, controller or actuator on the hand controller is preferably selected, causing saline flow at a pre-selected flow rate. Alternatively, a single controller or actuator having three different control modes can be used. As with the other actuators or actuator modes on the handheld controller, if at any time the third button is released, the saline flow preferably stops.

A pressure sensor is preferably connected to a pressure isolation valve as described above. Patient pressure monitoring can be determined at any time except when an injection of fluid exceeds the pressure set by the pressure isolation valve.

A multi-patient set can be designed so that at least some portions thereof can safely be reused for multiple patients. In such a design, for example, the syringe and interface to contrast/saline components, disposable valves and related tubing, and a multi-use high-pressure, aseptic connector can preferably be reused for multiple patients.

Handheld controllers, whether or not in fluid connection with the fluid path, and related tubing and check valves are preferably replaced for each patient. Likewise, any waste port, pressure port, and the interface to catheter are preferably replaced for each patient. Aseptic connectors of a multi-patient set can, for example, be wiped clean before connecting a disposable set for each new patient. Reusable or multi-patient sets preferably have a limited numbers of reuses and preferably are not used for longer than a set period of time, for example, an 8-hour period.

Figure 9:
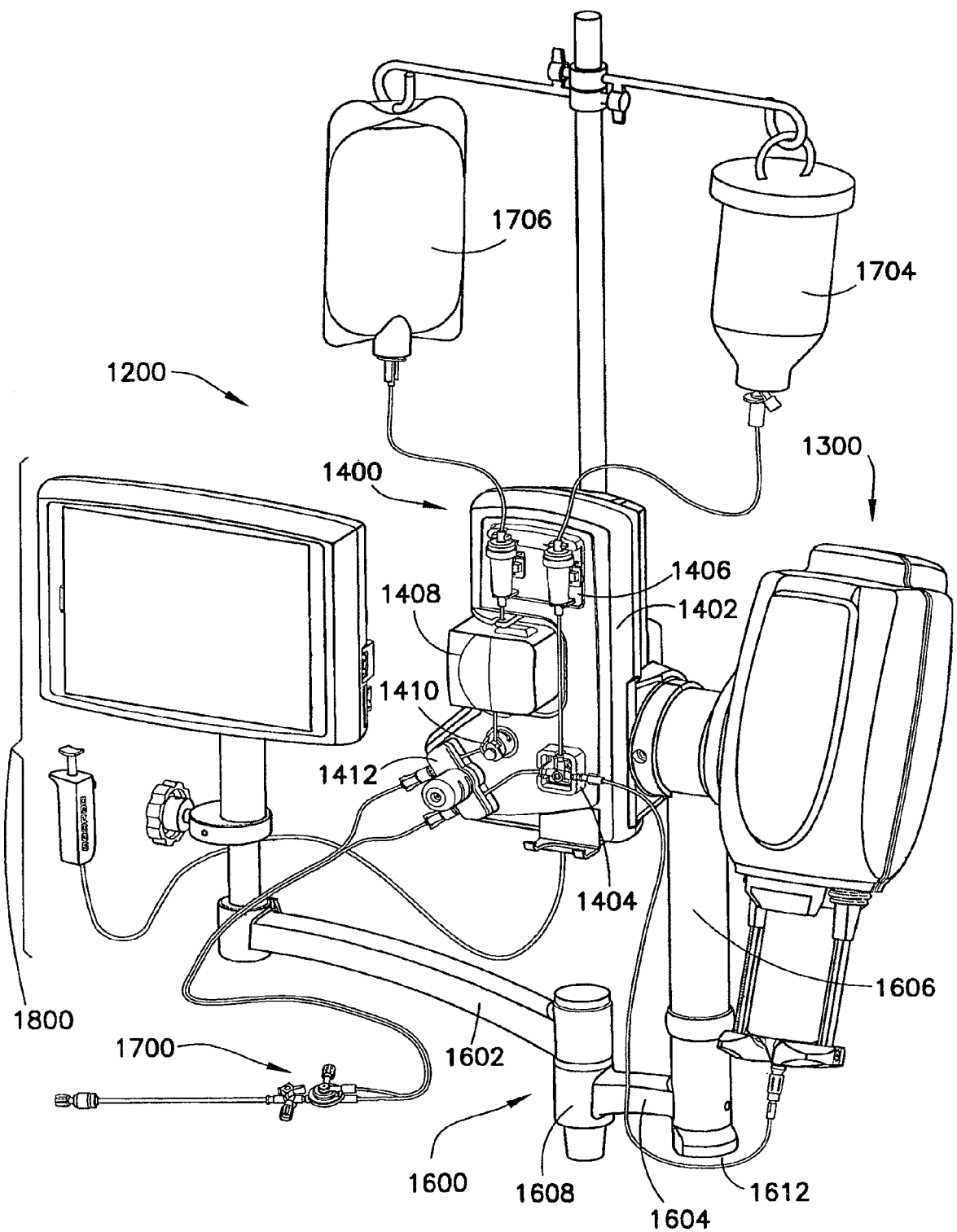
FIG. 9 is a perspective view of a fluid delivery or injection system in accordance with another embodiment of the present invention and including generally analogous components to the injection system of FIG. 7G.

Another embodiment of a fluid injector or delivery system 1200 is illustrated generally in FIG. 9. In this embodiment, an injector 1300 is operatively associated with a fluid control module 1400. The details of the injector 1300 are set forth in co-pending U.S. application Ser. No. 10/326,582, filed on Dec. 20, 2002, entitled FRONT LOAD PRESSURE JACKET SYSTEM WITH SYRINGE HOLDER AND LIGHT ILLUMINATION, and co-pending U.S. patent application Ser. No. 10/818,477, filed Apr. 5, 2004 entitled FLUID INJECTION APPARATUS WITH FRONT LOAD PRESSURE JACKET, LIGHT ILLUMINATION, AND SYRINGE SENSING, which are each incorporated herein by reference in their entirety. The injector 1300 is adapted to support and actuate a syringe, as described in the foregoing applications. The fluid control module 1400 is associated with the injector 1300 for controlling fluid flows delivered by the injector 1300. The fluid control module 1400 is generally adapted to support and control a fluid path set 1700 used to connect a syringe associated with the injector 1300 to a catheter (not shown) to be associated with a patient.

The fluid delivery system 1200 further includes a support assembly 1600 adapted to support the injector 1300 and the fluid control module 1400, as discussed further herein. The support assembly 1600 may be configured as a movable platform or base so that the fluid delivery system 1200 is generally transportable, or for connection to a standard hospital bed or examination table on which a patient will be located during an injection procedure. Additionally, the fluid delivery system 1200 preferably further includes a user-input control section or device 1800 for interfacing with computer hardware/software (i.e., electronic memory) of the fluid control module 1400 and/or the injector 1300. While the details of the fluid control module 1400 are set forth in detail hereinafter, the fluid control module 1400 generally includes a housing 1402, a valve actuator 1404 for controlling a fluid control valve, a fluid level sensing mechanism 1406, a peristaltic pump 1408, an automatic shut-off or pinch valve 1410, and an air detector assembly 1412. The details of the control section 1800 are also set forth hereinafter in this disclosure.

Figure 10:
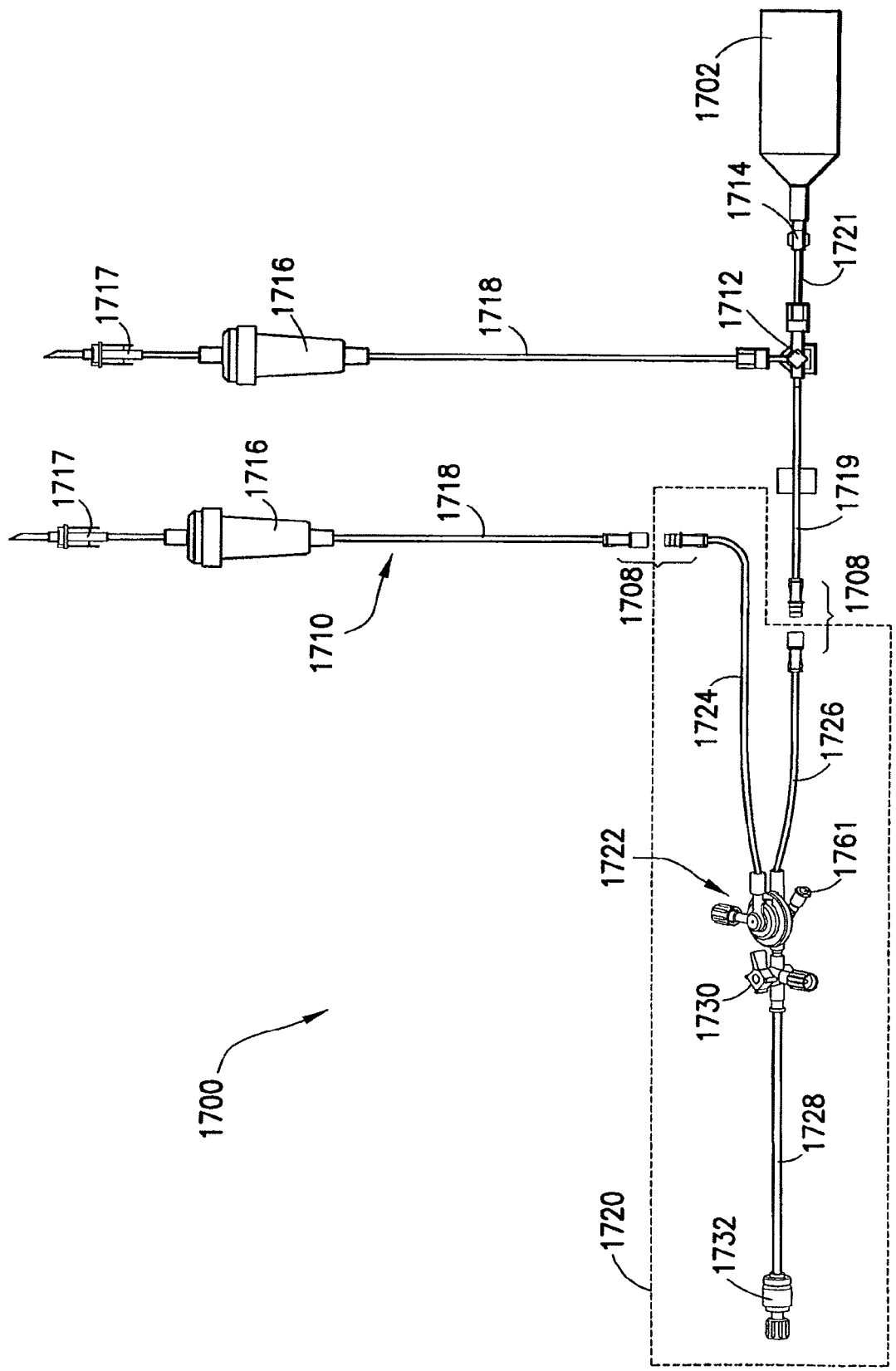
FIG. 10 is a side and partially perspective view of a fluid path set used with the fluid delivery system of FIG. 9.

As indicated, the fluid control module 1400 is generally adapted to support and control the fluid path set 1700 used to connect a syringe associated with the injector 1300 to a catheter (not shown). Referring now to FIGS. 9 and 10, the fluid path set 1700 is shown in greater detail in FIG. 10. The fluid path set 1700 may be considered to include a syringe 1702 that is to be associated with the injector 1300. The fluid path set 1700 is generally used to associate the syringe 1702 with a first or primary source of injection fluid 1704, also referred to herein as a primary fluid container, which will be loaded into the syringe 1702 for an injection procedure. The primary fluid container 1704 may be contrast media in the case of an angiographic procedure, as an example. The fluid path set 1700 is further adapted to associate the fluid control module 1400 with a secondary or additional source of fluid 1706, also referred to herein as a secondary fluid container, to be supplied or delivered to the patient via the catheter. In a typical angiographic procedure, saline is used as a secondary flushing fluid which is supplied to the patient between injections of contrast media.

In a general injection procedure involving the fluid delivery system 1200, the injector 1300 is filled with fluid from the primary fluid container 1704 and delivers the fluid via the fluid path set 1700 to the catheter and, ultimately, the patient. The fluid control module 1400 generally controls or manages the delivery of the injection through a valve associated with the fluid path set 1700, which is controlled or actuated by the valve actuator 1404 on the fluid control module 1400. The fluid control module 1400 is further adapted to deliver the fluid from the secondary fluid container 1706 under pressure via the peristaltic pump 1408 on the fluid control module 1400.

The fluid path set 1700, as illustrated in FIG. 10, generally comprises a first section or set 1710 and a second section or set 1720. The first section 1710 is generally adapted to connect the syringe 1702 to the primary fluid container 1704, and to connect the second section 1720 to the secondary fluid container 1706. The first section 1710 is preferably multi-patient section or set disposed after a preset number of injection procedures are accomplished with the fluid delivery system 1200. Thus, the first section 1710 may be used for a preset number of injection procedures involving one or more with patients and may then be discarded. Optionally, the first section 1710 may be adapted to be re-sterilized for reuse. The first section 1710 is preferably provided as a sterile set, preferably in a sterile package. The second section 1720 is a per-patient section or set, which is preferably disposed of after each injection procedure involving the fluid delivery system 1200. The fluid path set 1700 is generally similar to the fluid path set illustrated in FIG. 7B, discussed previously, but includes the structures discussed hereinafter. The first section 1710 and second section 1720 are placed in fluid communication by one or more connectors 1708, the details of which are also set forth hereinafter.

The first section 1710 includes a multi-position valve 1712, for example a 3-position stopcock valve, which is adapted to be automatically controlled or actuated by the valve actuator 1404 on the fluid control module 1400. The multi-position valve 1712 is adapted to selectively isolate the syringe 1702, the primary fluid container 1704, and the second section 1720 to selectively allow the injector 1300 to fill the syringe 1702 with fluid from the primary fluid container 1704, deliver the fluid loaded into the syringe 1702 to the second section 1720, or isolate the syringe 1702 from the primary fluid container 1704 and the second section 1720. The multi-position valve 1712 is connected to the syringe 1702 by a luer connection 1714, which may be a standard luer connection known in the art.

The first section 1710 further includes intervening drip chambers 1716 associated with the primary fluid container 1704 and the secondary fluid container 1706. The drip chambers 1716 are adapted to be associated with primary and secondary fluid containers 1704, 1706 with conventional spike members 1717. The fluid level sensing mechanism 1406 on the fluid control module 1400 is used to sense fluid levels in the drip chambers 1716 when the fluid path set 1700 is associated with the injector 1300 and the fluid control module 1400. Generally, operation of the fluid delivery system 1200 includes filling, loading, or "priming" the syringe 1402 with fluid from the primary fluid container 1704, which passes to the syringe 1402 via the drip chamber 1716 associated with the primary fluid container 1704. Similarly, during operation of the fluid delivery system 1200, fluid such as saline, from the secondary fluid container 1706 is supplied to the second section 1720 via the drip chamber 1716 associated with the secondary fluid container 1706. The drip chambers 1716 are generally adapted to permit fluid level sensors associated with the fluid level sensing mechanism 1406 to detect the level of fluid in the drip chambers 1716, for example by using optical or ultrasonic methods. Respective output lines 1718 made, for example, of conventional low pressure medical tubing, are associated with the drip chambers 1716 for connecting the drip chambers 1716 to the multi-position valve 1712 and the second section 1720. The outlet of the multi-position valve 1712 is connected to an output line 1719, which is used to connect the multi-position valve 1712 and syringe 1702 to the second section 1720. Due to the high injection pressures typically generated by the injector 1300 during an injection procedure such as angiography, the output line 1719 is preferably constructed of high pressure medical tubing. An inlet to the multi-position valve 1712 is connected via an inlet line 1721 to the syringe 1702, and is preferably also constructed of high pressure medical tubing.

The second section 1720 generally includes a pressure isolation mechanism or valve 1722. The pressure isolation mechanism 1722 is connected by respective input lines 1724, 1726 and the connectors 1708 to the first section 1710. The first input line 1724 is preferably formed of conventional medical tubing and connects the pressure isolation mechanism 1722 with the drip chamber 1716 associated with the secondary fluid container 1706. The second input line 1726 is preferably formed of high pressure medical tubing and connects the pressure isolation mechanism 1722 with the output line 1719 connected to the multi-position valve 1712 and, ultimately, the syringe 1702 and primary fluid container 1704. The tubing used for the second input line 1726 is preferably high pressure medical tubing.

An output line 1728 is associated with the pressure isolation mechanism 1722 for connecting the pressure isolation mechanism 1722 with the catheter. A second multi-position valve 1730, for example in the form of a stopcock valve, may be provided in the output line 1728, as a shut-off feature. As shown in FIG. 10, the multi-position valve 1730 may be provided as a simple shut-off valve to isolate the catheter from the first section 1710 of the fluid path set 1700. The output line 1728 may further include a catheter connection 1732 for associating the fluid path set 1700 with a catheter to be used in a fluid injection procedure involving the fluid delivery system 1200.

Figure 11:
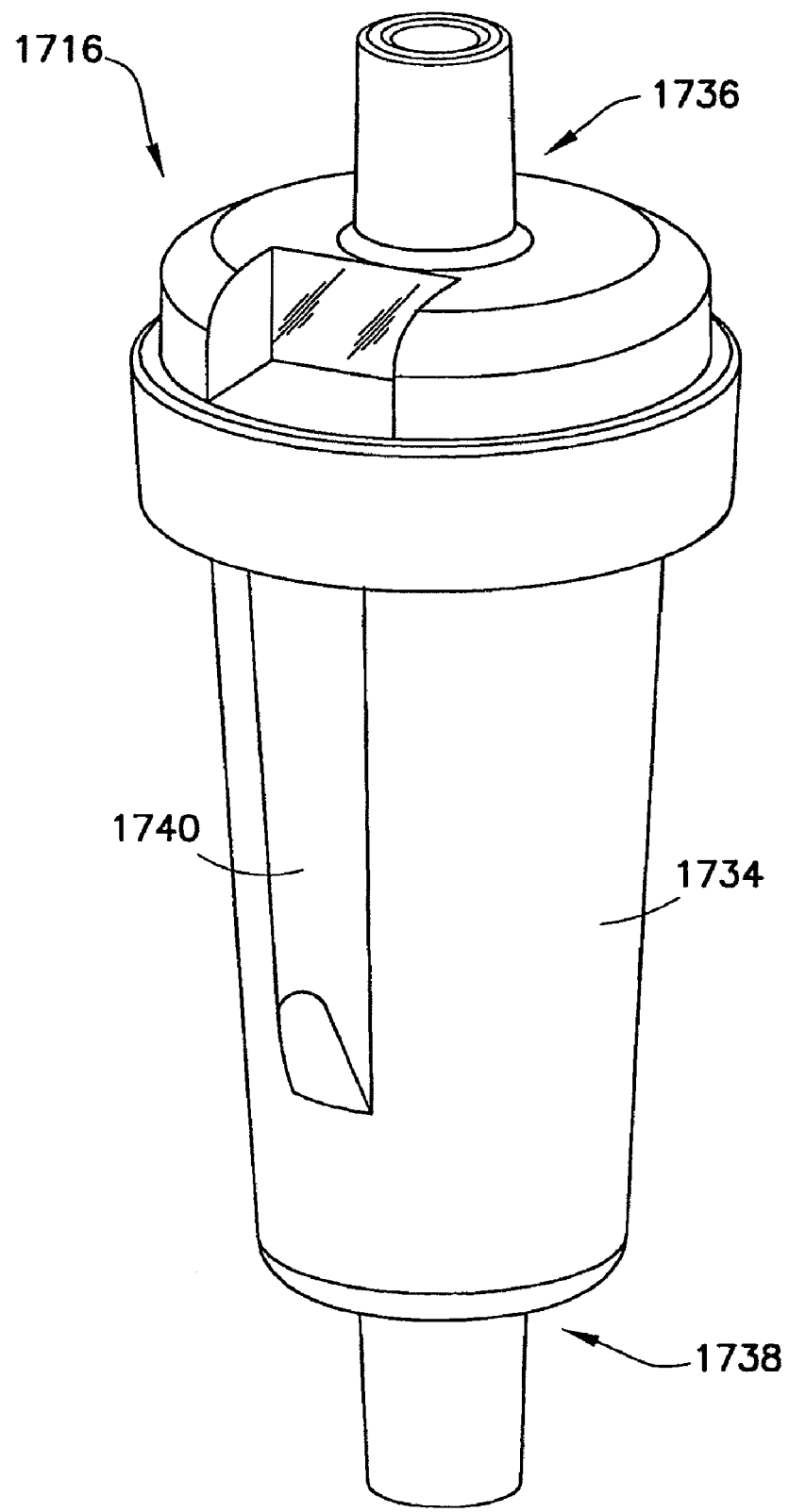
FIG. 11 is a perspective view of a drip chamber in accordance with the present invention and adapted for use in the fluid path of FIG. 10.
Figure 12:
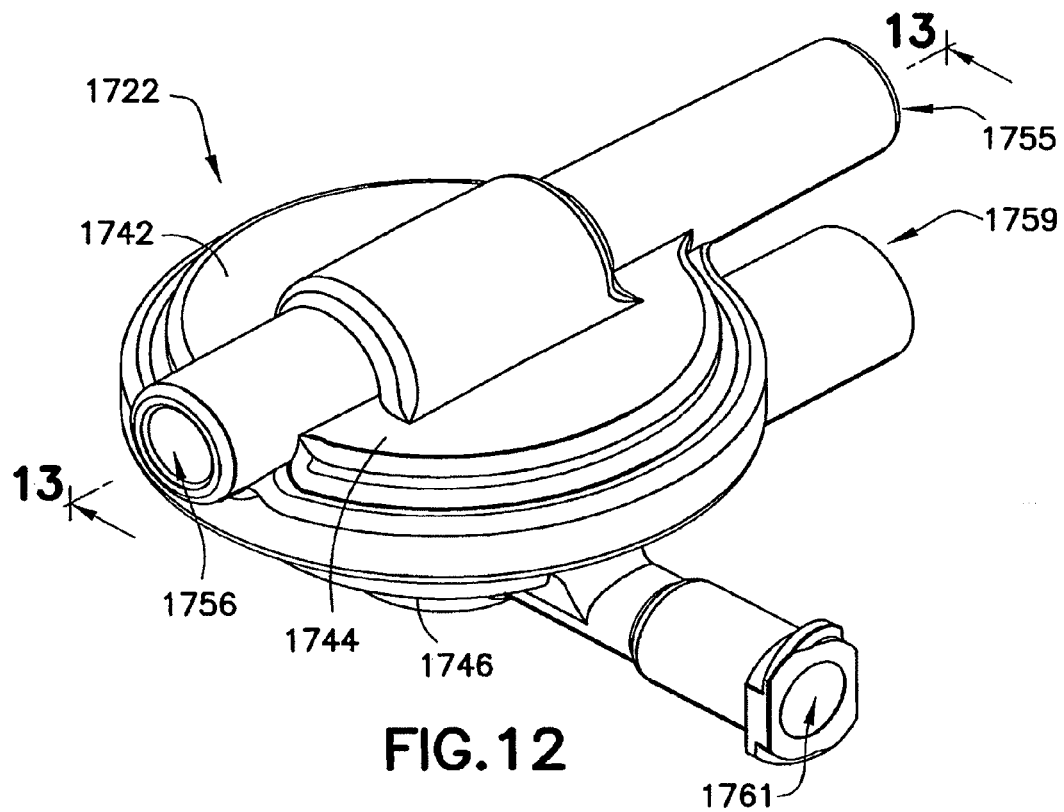
FIG. 12 is a perspective view of another embodiment of the pressure isolation mechanism or valve of the present invention and provided in the fluid path set of FIG. 10.

Referring briefly to FIG. 11, one of the drip chambers 1716 used in the fluid path set 1700 is shown in enlarged detail. The drip chamber 1716 shown in FIG. 11 generally has an elongated body 1734 with a top end 1736 and a bottom end 1738. The body 1734 is formed with a projection 1740, which generally extends longitudinally, laterally along the body 1740, or in any configuration on the body 1734 of the drip chamber 1716, and may even be in the form of a handle with an opening such as those found on plastic bottles. The projection 1740 is generally provided to interact with the fluid level sensing mechanism 1406 on the fluid control module 1400, and may be referred to as a "back" window because the projection 1740 will generally face the fluid level sensors in the fluid level sensing mechanism 1406 when the drip chamber 1716 is associated with the fluid level sensing mechanism 1406.

The body 1734 is preferably formed of a plastic material and, more particularly, a resiliently deformable medical-grade plastic material to allow in-place "priming" of the drip chamber 1716, when the drip chamber 1716 is associated with the fluid level sensing mechanism 1406. The fluid level sensing mechanism 1406 is generally adapted to support and secure the drip chambers 1716, as shown in FIG. 9. The projection 1740 further permits the drip chamber 1716 to be primed in place in the fluid level sensing mechanism 1406. The plastic material comprising the body 1734 may be substantially clear or slightly opaque, but the projection 1740 is preferably clear to allow an optical fluid level sensor in the fluid level sensing mechanism 1406 to detect the fluid level in the drip chamber 1716. The projection 1740 is preferably raised from the body 1734 of the drip chamber 1716 to allow priming of the drip chamber 1716. Generally, the body 1734 of the drip chamber 1716 is sufficiently clear to allow light transmission from lighting associated with the fluid level sensing mechanism 1406. The body 1734 of the drip chamber 1716 will generally act as a light conduit or "light pipe" that will illuminate the fluid flow path in the medical tubing forming the output lines 1718 associated with the drip chambers 1716 connected to the primary and second fluid containers 1704, 1706.

Figure 13:
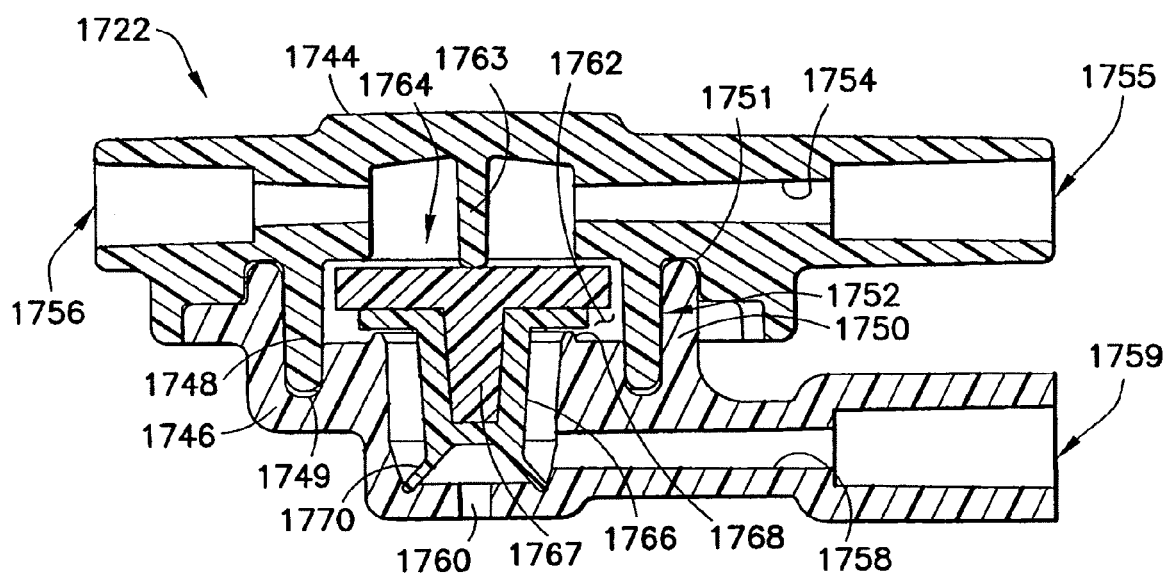
FIG. 13 is a cross section view taken along lines 13-13 in FIG. 12.

Referring to FIGS. 12-15, the pressure isolation mechanism 1722 is shown in greater detail. The pressure isolation mechanism 1722 includes a housing 1742. The housing 1742 may be a unitary housing or, preferably, a multi-piece housing as shown in FIG. 13. Preferably, the housing 1742 is a two-piece housing including a first portion 1744 and a second portion 1746, which are adapted to connect together to form the housing 1742. The first and second portions 1744, 1746 are preferably formed for interference engagement with each other.

The interference engagement is formed by engagement of a depending annular flange 1748 formed on the first portion 1744 of the housing 1742 with a corresponding recess or groove 1749, for example, a circular recess or groove, formed or defined in the second portion 1746 of the housing 1742. The recess 1749 is purposely made slightly smaller in width than the thickness of the annular flange 1748, so that when the first and second portions 1744, 1746 of the housing 1742 are joined together there is interference engagement between the annular flange 1748 and the recess 1749. The second portion 1746 of the housing 1742 may include a raised annular flange 1750 that engages or cooperates with a corresponding recess or groove 1751 defined in the first portion 1744. The raised annular flange 1750 may engage with the recess 1751 in a similar friction fit manner as the annular flange 1748 and recess 1749 discussed previously. The combination of the annular flanges 1748, 1750 and recesses 1749, 1751 generally define a shear interface 1752 between the first and second portions 1744, 1746 of the housing 1742, which increases their assembly strength. An adhesive or ultrasonic weld may be used along the shear interface 1752 to secure the first and second portions 1744, 1746 together. The connection between the flanges 1748, 1750 and the recesses 1749, 1751 generally define a tortuous path along this connection line.

The first portion 1744 of the housing 1742 defines a primary or high pressure lumen 1754, which forms a high pressure side of the pressure isolation mechanism 1722. An inlet 1755 to the high pressure or primary lumen 1754 is in fluid communication with the second input line 1726, which is the high pressure line connecting the pressure isolation mechanism 1722 with the output line 1719 associated with the multi-position valve 1712 and, ultimately, the syringe 1702 and the primary fluid container 1704. An outlet 1756 of the primary lumen 1754 is connected to the second multi-position valve 1730, which may be provided in the output line 1728 as discussed previously.

The second portion 1746 of the housing 1740 defines a secondary or low pressure lumen 1758, which generally forms a low pressure side of the pressure isolation mechanism 1722. The secondary lumen 1758 has an inlet 1759 that is in fluid communication with the first input line 1724, which is the low pressure line that connects the pressure isolation mechanism 1722 to the secondary fluid container 1706 via the peristaltic pump 1408 on the fluid control module 1400 and drip chamber 1716. The second portion 1746 of the housing 1742 includes a vent hole 1760 provided for proper operation of the pressure isolation mechanism 1722. The second portion 1746 of the housing 1742 further includes a pressure isolation port 1761 to which a pressure transducer (See FIGS. 7B through 7F) may be connected. The structure forming the pressure isolation port 1761 may terminate in a luer connector for connecting a pressure transducer to the pressure isolation port 1761.

The first and second portions 1744, 1746 of the housing 1742 may define an internal chamber 1762, generally in fluid communication with the primary lumen 1754 and the secondary lumen 1758. The first portion 1744 of the housing 1742 may include a depending retaining member 1763 extending into the internal chamber 1762. An internal valve member 1764 is located in the internal chamber 1762 and is used to isolate the pressure isolation port 1761 when the pressure isolation mechanism 1722 is associated with the syringe 1702, (i.e., in fluid communication with an operating syringe 1702). The valve member 1764 is generally engaged by the retaining member 1763 depending or extending from the first portion 1744 of the housing 1742 to maintain a preload of the valve member 1764. The valve member 1764 is generally adapted to bias the pressure isolation mechanism 1722 to a normally open position, wherein the primary lumen 1754 is in fluid communication with the secondary lumen 1758 and the pressure isolation port 1761 through the internal chamber 1762. The valve member 1764 is generally further adapted to isolate the pressure isolation port 1761 once fluid pressure in the primary lumen 1754 reaches a preset pressure, as described further herein.

The valve member 1764 is preferably a two-piece structure comprising a seat member 1766 and a base portion 1767. The seat member 1766 is generally adapted to seat against a seal ring 1768 formed on the second portion 1746 of the housing 1742 in the closed position of the valve member 1764, thereby isolating the primary lumen 1754 from the secondary lumen 1758 and the pressure isolation port 1761. The seat member 1766 includes an integral biasing portion 1770. The biasing portion 1770 is a generally conical shaped portion of the seat member 1766 that is hollow and preferably has a pre-established or preset spring force tension. The base portion 1767 is generally engaged by the retaining member 1763 depending or extending from the first portion 1744 of the housing 1742 to maintain a preload of the conical shaped biasing portion 1770 and form a seal with the body of the second portion 1746 of the housing 1742, thereby preventing fluid from leaking or exiting via the vent hole 1760. The vent hole 1760 allows for proper operation of the valve member 1764 by allowing air to vent from the conical shaped biasing portion 1770 during operation of the valve member 1764. When the pressure within primary lumen 1754 increases during an injection procedure, the biasing portion 1770 of the seat member 1764 responds by deforming within the internal chamber 1762 until the seat member 1766 of the valve member 1764 seats against the seal ring 1768 formed on the second portion 1746 of the housing 1742. Once the seat member 1766 seats against the seal ring 1768, the valve member 1764 is in a closed position. The pre-established or preset spring force tension is preferably selected to prevent damage to the pressure transducer, saline line, or other pressure sensitive devices typically connected to the pressure isolation port 1761 and may be pre-selected such that the valve member 1764 is in the closed position when the fluid pressure in the primary lumen 1754 is less than 70 psi. In the closed position of the valve member 1764, the primary lumen 1754 is isolated from the secondary lumen 1758 and the pressure isolation port 1761.

Figure 14:
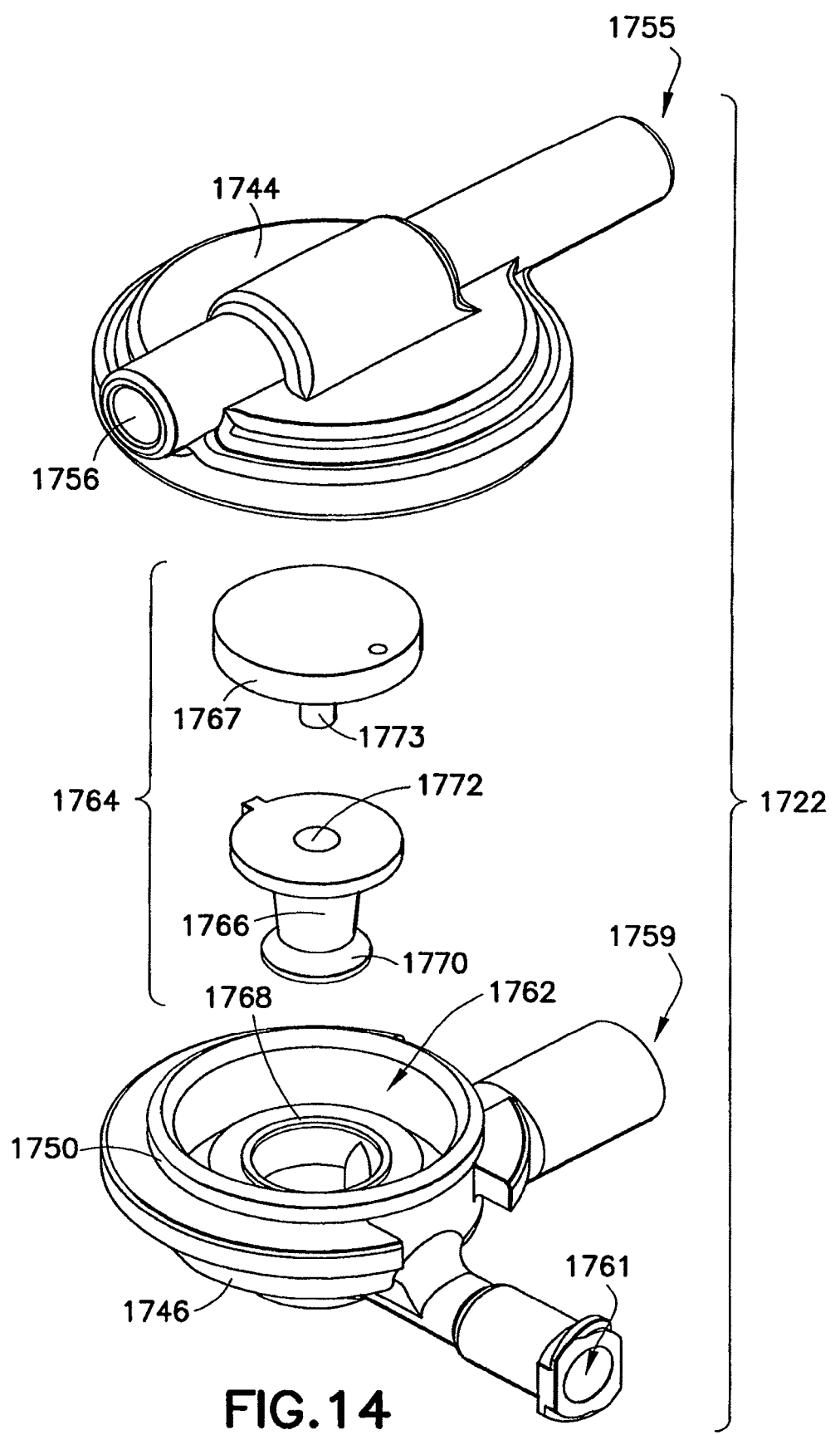
FIG. 14 is an exploded perspective view of the pressure isolation mechanism of FIG. 12.
Figure 15:
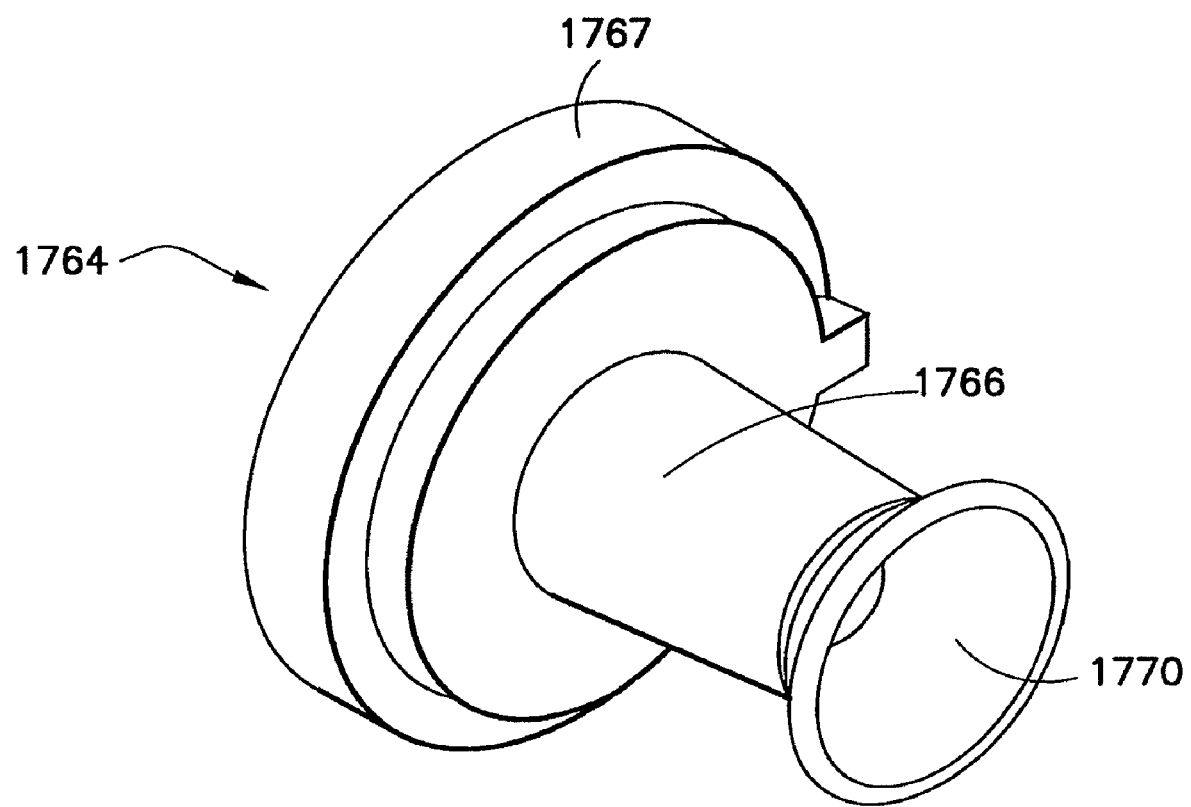
FIG. 15 is a perspective view of a biasing valve member used in the pressure isolation mechanism of FIG. 12.
Figure 16:
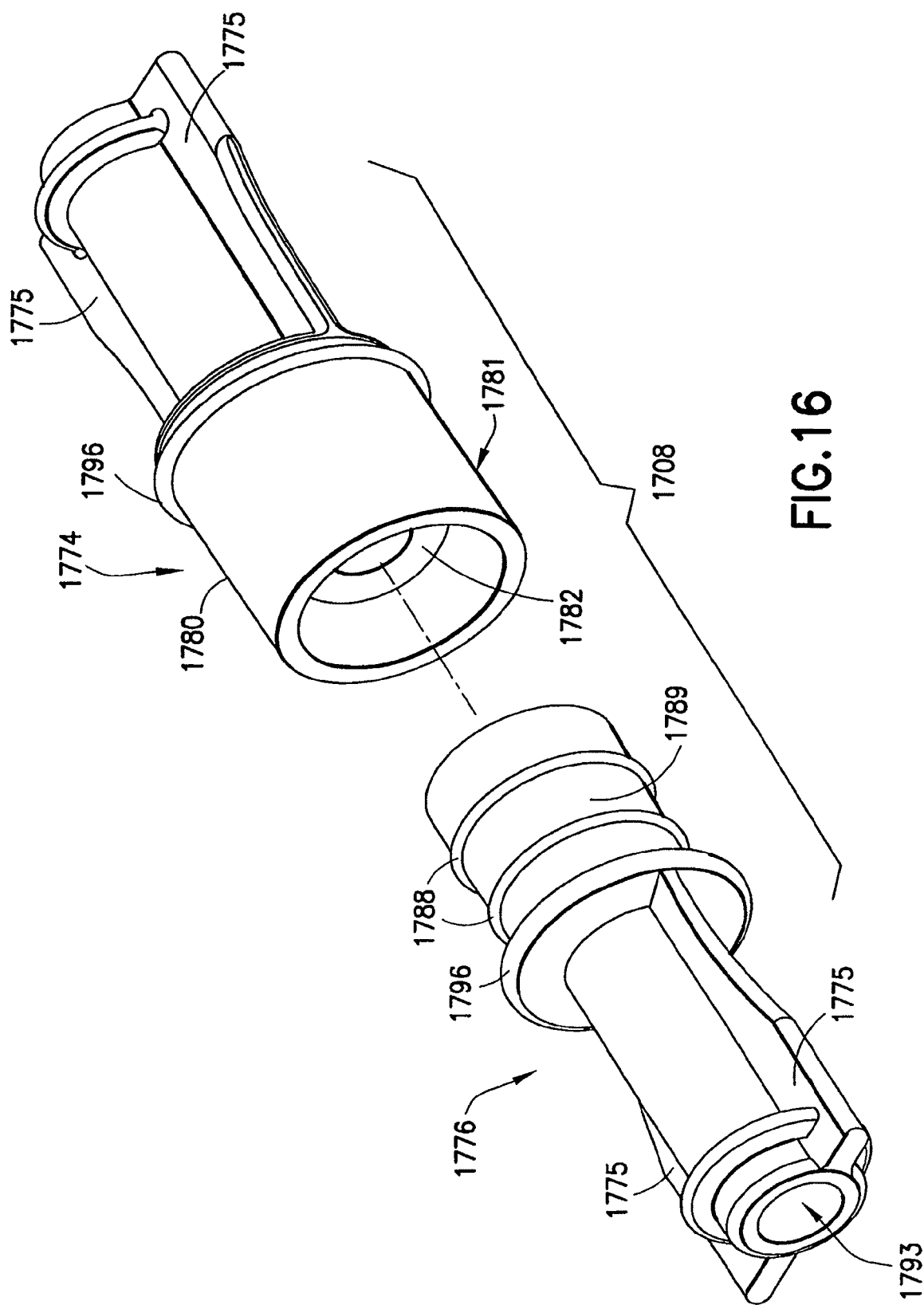
FIG. 16 is a perspective view of a connector in accordance with the present invention and adapted for use in the fluid path set of FIG. 10, and showing first and second connector members of the connector disconnected from one another.

As FIG. 14 shows, the seat member 1766 may define an opening 1772 for receiving a tab or projection 1773 on the base portion 1767 for connecting the base portion 1767 to the seat member 1766. The seat member 1766 and base portion 1767 may be secured together by mechanical devices (i.e., fasteners), adhesively secured together, or bonded together when the valve member 1764 is formed. For example, the seat member 1766 and the base portion 1767 may be formed of different polymeric materials that will adhere to one another, for example, when elevated heat or pressure are applied. For example, the seat member 1766 may be made of a thermoplastic elastomer and the base portion 1767 formed of a polypropylene that will adhere to the thermoplastic elastomer when the seat member 1766 and the base portion 1767 are molded together.

FIGS. 16-19 illustrate the reduced or anti-contamination connector 1708 used to connect the first section 1710 and second section 1720 in the fluid path set 1700 shown in FIG. 10 in greater detail. As shown in FIG. 10 discussed previously, one connector 1708 connects the high pressure, second input line 1726 associated with the pressure isolation mechanism 1722 with the high pressure output line 1719 from the multi-position valve 1712 associated with controlling fluid flow from the syringe 1702. A second connector 1708 connects the low pressure, first input line 1724 associated with the pressure isolation mechanism 1722 to the output line 1718 associated with the drip chamber 1716 connected to the secondary fluid container 1706.

The connector 1708 generally includes a first connector member 1774 that is adapted for removable connection to a second connector member 1776. The first and second connector members 1774, 1776 are designed or structured to reduce the possibility of contaminating the internal elements of the first and second connector members 1774, 1776 when they are handled by a user of the connector 1708. The first and second connector members 1774, 1776 are preferably unitary structures that are integrally formed from plastic material, such as a medical-grade plastic material capable of resisting pressures generated during injection procedures such as angiography. The first and second connector members 1774, 1776 are preferably formed with external wings 1775 for grasping by a user of the connector 1708 while manipulating the first and second connector members 1774, 1776, particularly when connecting the first and second connector members 1774, 1776 together. As discussed herein, the first and second connector members 1774, 1776 preferably include structures that provide a removable threaded engagement between the first and second threaded members 1774, 1776. The wings 1775 generally provide the mechanical advantage necessary to tighten the preferred threaded engagement between the first and second connector members 1774, 1776. The first connector member 1774 defines a central lumen 1777 that extends entirely through the first connector member 1774. Likewise, the second connector member 1776 defines a central lumen 1778 extending entirely through the second connector member 1776, so that when the first and second connector members 1774, 1776 are connected, fluid communication is established therebetween via lumens 1777, 1778.

Figure 17:
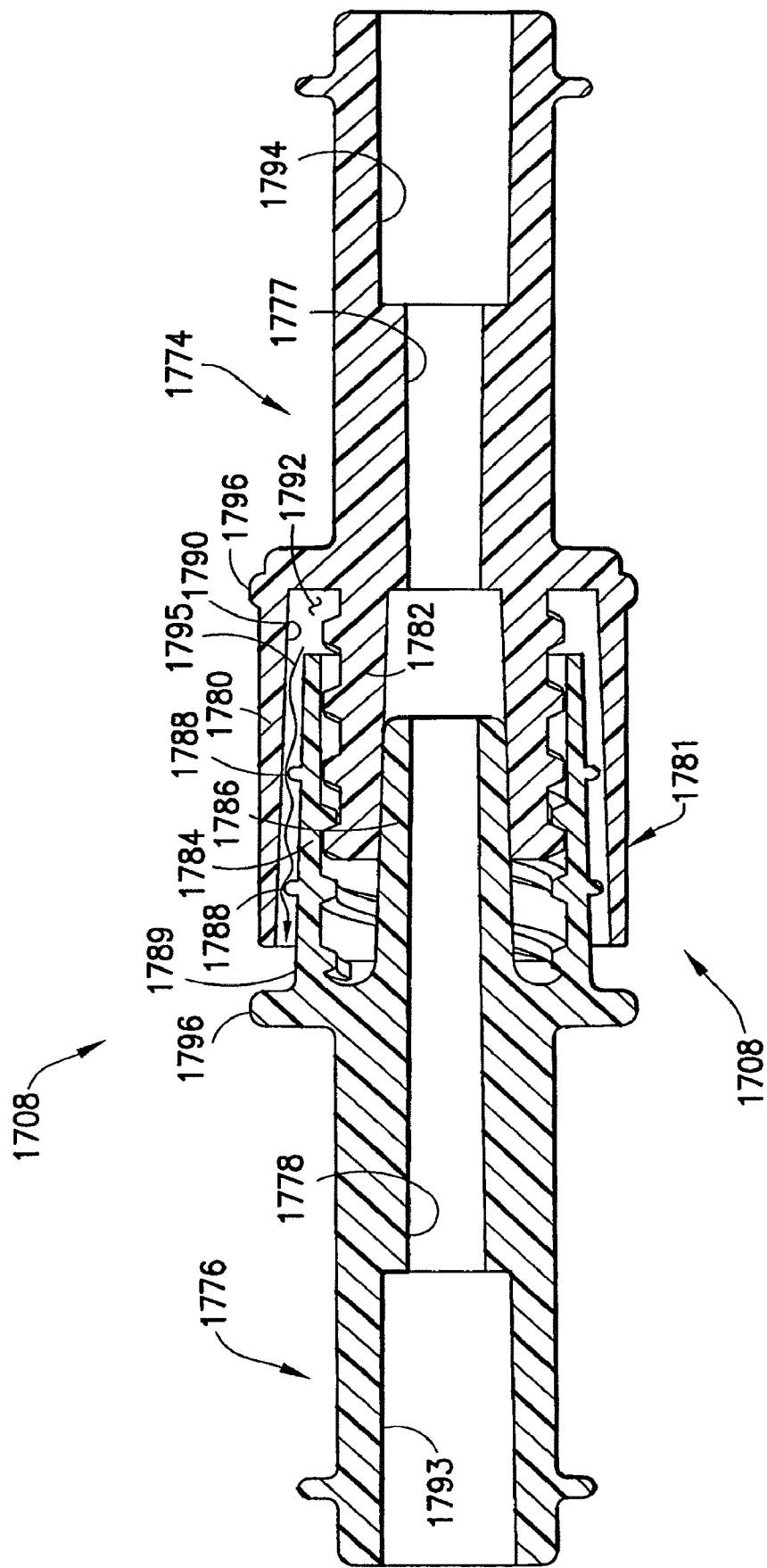
FIG. 17 is a longitudinal cross sectional view of the connector of FIG. 16, showing the first and second connector members connected together.

The first connector member 1774 includes an outer housing 1780. The outer housing 1780 is generally a cylindrical shaped hollow structure and may have a smooth or textured outer surface 1781. The first connector member 1774 further includes a first threaded member 1782 located within the outer housing 1780. The first threaded member 1782 may be coaxially located within the outer housing 1780. As shown in FIG. 17, the lumen 1777 in the first connector member 1774 extends through the first threaded member 1782. The first threaded member 1782 is preferably externally threaded and may be in the form of an externally threaded female luer fitting. The first threaded member 1782 is recessed within the outer housing 1780 by a recessed distance $R_1$, as shown in FIG. 18. The recessed distance $R_1$ is preferably sufficient to prevent contact with the end or tip of the first threaded member 1782 when a person touches the end or tip of the first connector member 1774. The recessed distance $R_1$ thereby reduces the possibility of contaminating the first threaded member 1774, when the first connector member 1774 is manipulated by a user of the connector 1708. In particular, the recessed distance $R_1$ is of sufficient distance that human skin on a person's finger or thumb will not penetrate to the depth of the first threaded member 1782 and come into contact with the end or tip of the first threaded member 1782.

The second connector member 1776 includes a second threaded member 1784, which generally forms the connecting portion or structure of the second connector member 1776. The second threaded member 1784 is preferably internally threaded to receive the externally threaded first threaded member 1782 for connecting the first and second connector members 1774, 1776 together in removable engagement. The first threaded member 1782 may be in the form of an externally-threaded female luer. The second connector member 1776 further includes a luer fitting 1786 located in the second threaded member 1784. The luer fitting 1786 is preferably in the form of a male luer adapted to cooperate with the first threaded member 1782 when the first connector member 1774 is connected to the second connector member 1776. The luer fitting 1786 is preferably coaxially disposed in the second threaded member 1784. The lumen 1778 in the second connector member 1776 extends entirely through the luer fitting 1786. The luer fitting 1786 is recessed within the second threaded member 1784 by a recessed distance $R_2$, in a similar manner to how the first threaded member 1782 is recessed within the outer housing 1780. The second threaded member 1784 further includes one or more circumferentially-extended raised structures 1788, such as rings, on an outer surface 1789 thereof.

FIG. 17 shows the connection between the first and second connector members 1774, 1776 forming the connector 1708. In the connected arrangement of the first and second connector members 1774, 1776, the first threaded member 1774 is secured to the second connector member 1776 by removable threaded engagement between the externally threaded first threaded member 1782 and the internally threaded second threaded member 1784. The luer fitting 1786 recessed within the second threaded member 1784 cooperates with the first threaded member 1782 to provide fluid communication between the first and second connector members 1774, 1776. The present invention is not intended to be limited to the specific connection arrangement shown in FIG. 17, and the locations of the first threaded member 1782 and the second threaded member 1784 may be reversed in accordance with the present invention. Thus, the first threaded member 1782 may be provided on the second connector member 1776 and the second threaded member 1784 may be provided on the first connector member 1774.

In the connected arrangement between the first and second connector members 1774, 1776, the first threaded member 1782 and the second threaded member 1784 are threadably engaged and coaxially overlap one another. The outer housing 1780 of the first connector member 1774 generally encompasses the connection between the first and second threaded members 1782, 1784. In particular, the outer housing 1780 generally coaxially encompasses the overall connection between the first and second threaded members 1782, 1784. The outer housing 1780 has an internal wall or surface 1790 located opposite from the outer surface 1789 of the second threaded member 1784, when the first and second threaded members 1782, 1784 are threadably engaged. As FIG. 18 illustrates, the inner wall or surface 1790 of the outer housing 1780 and the first threaded member 1782 generally define an annular cavity 1791 about the first threaded member 1782, in which the second threaded member 1784 is generally received when the first and second threaded members 1782, 1784 are threadably engaged. The distance between the inner wall or surface 1790 of the outer housing 1780 and the first threaded member 1782 in the annular cavity 1791 is preferably sufficient to receive at least the overall wall thickness of the second threaded member 1784, including the raised structures 1788 on the outer surface 1789 of the second threaded member 1784 as generally depicted in FIG. 17.

In the connected arrangement of the first and second connector members 1774, 1776, the annular cavity 1791 is substantially enclosed by the second threaded member 1784 to form a substantially enclosed chamber 1792. The chamber 1792 is generally bounded by the body of the first threaded member 1782, the inner wall or surface 1790 of the outer housing 1780, and the end or tip of the second threaded member 1784. The chamber 1792 is generally adapted to trap liquids, such as blood or contrast media, therein that may spill or leak from the first and second threaded members 1774, 1776, when they are connected or disconnected to connect or disconnect the first and second sections 1710, 1720 of the fluid path set 1700, for example during or after an angiography procedure.

The first connector member 1774 and second connector member 1776 define respective conduit-receiving cavities 1794, 1793 at the ends of the first and second connector members 1774, 1776 opposite from the first threaded member 1782 and the second threaded member 1784, respectively. The conduit-receiving cavities 1794, 1793 are generally adapted to receive medical tubing to be associated with the first and second connector members 1774, 1776. The medical tubing may be secured in the conduit-receiving cavities 1793, 1794 through the use of an appropriate medical-grade adhesive. The primary and secondary lumens 1754, 1758 may be formed with similar conduit-receiving cavities for receiving medical tubing used to connect the pressure isolation mechanism 1722 to other components in the fluid path set 1700. A suitable medical-grade adhesive may be used in such cavities to secure the medical tubing. Similar structures and connections may also be provided in the inlet and outlet ports of the drip chambers 1716.

As indicated previously, in the connected arrangement of the first and second connector members 1774, 1776, the liquid-trapping chamber 1792 is formed, and is generally used to trap liquids that may spill or leak from the first and second connector members 1774, 1776, when they are connected or disconnected during or after an injection procedure involving the fluid path set 1700. The raised structures 1788 on the outer surface 1789 of the second connector member 1784 are adapted to form a tortuous path 1795 for inhibiting liquid flow out of or into the liquid-trapping chamber 1792. Thus, liquid-trapping generally means inhibiting liquid flow rather than fully containing liquid. The tortuous path 1795 will generally cause liquids present or leaking into the chamber 1792 to remain in the chamber 1792, and will further inhibit outside liquid from migrating into the sterile connection between the first threaded member 1782 and the second threaded member 1784. By maintaining contaminated liquids in the chamber 1792 or generally between the inner surface 1790 of the outer housing 1780 and the outer surface of 1780 of the second threaded member 1784, the sterility of the connection between the luer fitting 1786 and the first threaded member 1782 is generally maintained. Additionally, even when the first connector member 1774 is disconnected from the second connector member 1776, the annular cavity 1791 about the first threaded member 1782 will act to maintain any contaminated liquids generally within the outer housing 1780, and maintain the sterility of the luer fitting 1786 within the second threaded member 1784. Thus, the second connector member 1776 may be re-used in a connection arrangement involving a different first connector member 1774.

Referring to FIGS. 18 and 19, the first and second connector members 1774, 1776 may be formed with circumferentially-extending raised ribs 1796 adapted to secure removable protector caps 1798 on the first and second connector members 1774, 1776 prior to connecting the first and second connector members 1774, 1776. FIGS. 18 and 19 show the protector caps 1798 engaged with the first and second connector members 1774, 1776. The protector caps 1798 define circumferentially-extending internal grooves or recesses 1799 for receiving the raised ribs 1796 on the first and second connector members 1774, 1776. The raised rib 1796 on the first and second connector members 1774, 1776 are preferably adapted to frictionally engage the grooves or recesses 1799 formed in the protector caps 1798 to maintain the protector caps 1798 on the first and second connector members 1774, 1776. The protector caps 1798 generally maintain the sterility of the first and second threaded members 1782, 1784 prior to connecting the first and second connector members 1774, 1776 together.

Referring further to FIG. 10, the protector caps 1798 may be used to cover the first and second connector members 1774, 1776 of the connectors 1708 in the fluid path set 1700 before and after injection procedures involving the fluid path set 1700. Thus, the first and second sections 1710, 1720 of the fluid path set 1700 may be kept disconnected prior to an injection procedure when the fluid delivery system 1200 is being readied to carry out an injection procedure. Moreover, when an injection procedure is complete, additional, sterile protector caps 1798 may be used to cover the first or second connector members 1774, 1776 in the connectors 1708 associated with the first section 1710 of the fluid path set 1700, so that this portion of the fluid path set 1700 may be reused.

As the connector 1708 of the present invention generally includes a male-threaded first connector member 1774 and a female-threaded second connector member 1776, the male-threaded/female-threaded orientation of the first and second connector members 1774, 1776 may be used as a tactile, physical indicator to prevent the high pressure primary input line 1726 to the pressure isolation mechanism 1722 from being incorrectly connected to the output line 1718 associated with the secondary fluid container 1706. Similarly, and more importantly, this feature may be used to prevent the low pressure, second input line 1724 to the pressure isolation mechanism 1722 from being incorrectly connected to the high pressure output line 1719 associated with multi-position valve 1712 controlling flow rate from the syringe 1702. As FIG. 10 illustrates, the locations of the first and second connector members 1774, 1776 are reversed in the connectors 1708 used in the fluid path set 1700, which will prevent inadvertent, incorrect cross-connections between the first and second sections 1710, 1720 in the fluid path set 1700.

Referring to FIGS. 9-10 and 20-21 the fluid control module 1400 is shown in greater detail. The fluid control module or device 1400, as indicated previously, generally includes a housing 1402, a valve actuator 1404, a fluid level sensing mechanism 1406, a peristaltic pump 1408, an automatic shut-off or pinch valve 1410, and an air detector assembly 1412. The various components comprising the fluid control module or device 1400 will be discussed in detail herein.

The housing 1402 generally defines a port 1420 for associating the injector 1300 with the fluid control module 1400. In particular, the injector 1300 is generally mounted to the fluid control module 1400 to be pivotal relative to the fluid control module 1400. The port 1420 includes a mating structure 1422 for connecting the injector 1300 to the fluid control module 1400 and providing for the pivotal connection between the injector 1300 and the fluid control module 1400. The port 1420 defines an opening 1424 for passing electrical conduits (not shown) therethrough to operatively connect computer hardware provided in the injector 1300 with computer hardware in the fluid control module 1400, so that the injector 1300 and fluid control module 1400 are electrically connected. While the port 1420 is shown on the side of the fluid control module 1400, this configuration is just an exemplary arrangement for the pivotal connection between the injector 1300 and fluid control module 1400 and other configurations are possible in accordance with the present invention such as mounting the injector at the top of the fluid control module 1400.

The housing 1402 may be a multi-piece structure comprised of opposing sides or portions 1426, 1428 that are secured together by conventional mechanical fasteners or similar fastening methods. The fluid control module 1400 is generally adapted to support an IV pole 1430 used to support containers of fluids, for example the primary fluid container 1704 (i.e., contrast media) and the secondary fluid container 1706 (i.e., saline), the contents of which are supplied to a patient via the fluid delivery system 1200. In particular, the rear side or portion 1428 of the housing 1402 is adapted to support the IV pole 1430. A hand controller support 1432 may be connected to the front side or portion of the housing 1402 for supporting a hand controller used to operate the fluid delivery system 1200, as discussed further herein. Additionally, the fluid control module 1400 preferably includes a connector 1433 adapted to operatively associate a hand controller with the fluid control module 1400.

Figure 22:
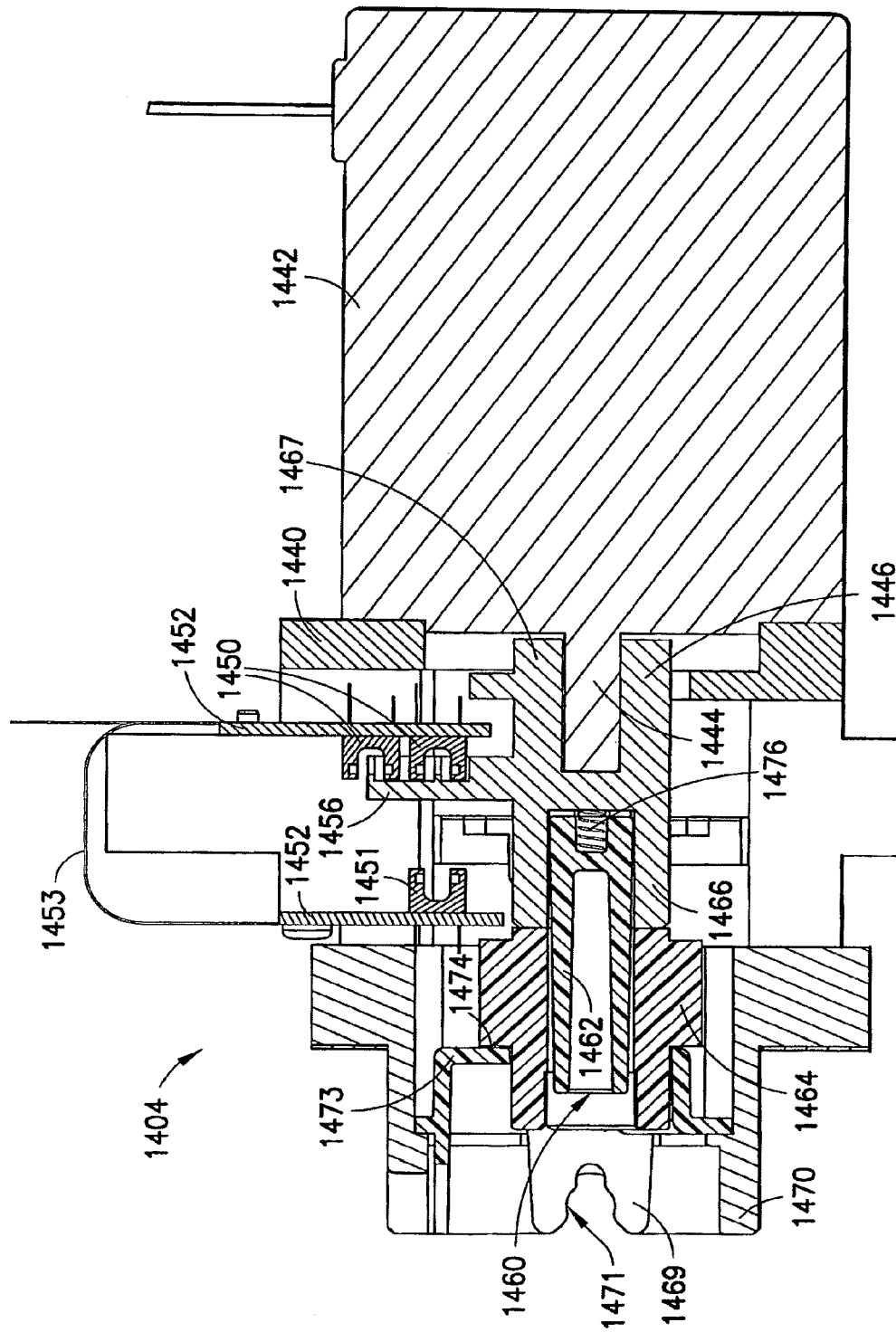
FIG. 22 is a longitudinal cross sectional view of a valve actuator of the fluid control module or device shown in FIGS. 20 and 21.
Figure 23:
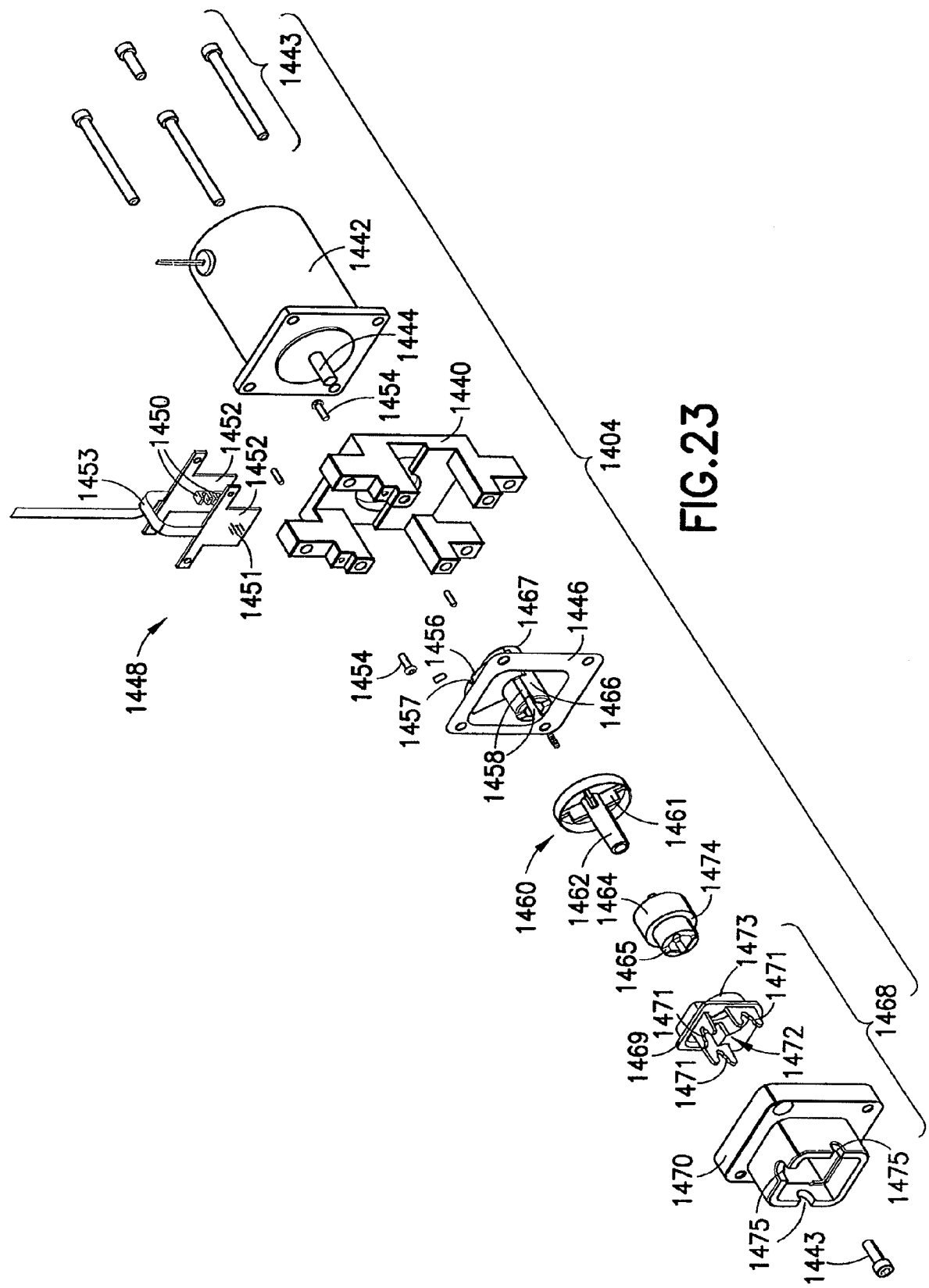
FIG. 23 is an exploded perspective view of the valve actuator of FIG. 22.

Referring further to FIGS. 22 and 23, the valve actuator 1404 is shown in greater detail. Generally, the valve actuator 1404 is adapted to support and actuate the multi-position valve 1712 associated with the primary section 1710 of the fluid path set 1700. The multi-position valve 1712, as indicated previously, may be a three-position stopcock valve. The valve actuator 1404 is generally adapted to selectively move or actuate the multi-position valve 1712 between three set positions of the multi-position valve 1712, as will be discussed further herein. Generally, the valve actuator 1404 is adapted to place the multi-position valve 1712 in one of three distinct positions, including (1) an inject or open position, (2) a fill position, and (3) a closed or isolation position. In the inject position, the syringe 1702 of the fluid path set 1700 is in fluid communication with the secondary section 1720 of the fluid path set 1700. In the fill position, the syringe 1702 is in fluid communication with the primary fluid container 1704 via the drip chamber 1716 associated with the primary fluid container 1704. Finally, in the closed position, the syringe 1702 is isolated from the primary fluid container 1704 and the second section 1720 of the fluid path set 1700. The specific components of the valve actuator 1404 adapted to place the multi-position valve 1712 in the foregoing positions or states will be discussed further herein.

As FIGS. 22 and 23 generally illustrate, the valve actuator 1404 is a multi-piece apparatus adapted to accept, support, and actuate the multi-position valve 1712. The valve actuator 1404 includes a base support member 1440 which is generally used to support the various components of the valve actuator 1404. The base support member 1440 may be a machined part, for example, a machined aluminum part. A stepper motor 1442 is secured by mechanical fasteners 1443 to one side of the base support member 1440. The stepper motor 1442 includes an output shaft 1444 that provides the motive forces for operating the valve actuator 1404. A shaft interface 1446 is disposed on the other side of base support member 1440 from the stepper motor 1442, and is in operative engagement with the output shaft 1444. The shaft interface 1446 is associated with the output shaft 1444 to transfer the motor torque provided by the stepper motor 1442 to other components of the valve actuator 1404, as discussed herein. The shaft interface 1446 may be secured to the base support member 1440 using the same mechanical fasteners 1443 used to secure the stepper motor 1442 to the base support member 1440.

The valve actuator 1404 further includes a photosensor assembly or array 1448 that includes, preferably, two photosensor position sensors 1450 for indicating the position of the handle of the multi-position valve 1712 when associated with the valve actuator 1404, and a third photosensor 1451 for indicating the presence of the multi-position valve 1712 in the valve actuator 1404. The various photosensors 1450, 1451 are carried or supported on two plates 1452 joined by a connecting member 1453. The plates 1452 are secured to the base support member 1440 by mechanical fasteners 1454, such that the photosensor assembly 1448 is associated with the shaft interface 1446. In particular, the shaft interface 1446 includes two semi-circular structures or rings 1456, only one of which is shown in FIGS. 22 and 23, that interface with the position sensors 1450 to indicate the position of the stepper motor 1442. The position of the stepper motor 1442 may be correlated to the position of the handle of the multi-position valve 1712 and, thus, reflect the operational position of the multi-position valve 1712 (i.e., inject, fill, isolate). In particular, the semi-circular structures 1456 may define windows 1457 that correlate to the three possible operational positions of the handle of the multi-position valve 1712. The shaft interface 1446 further provides a hard stop that interfaces with the base support member 1440 to prevent over-rotation of the handle of the multi-position valve 1712 during operation of the valve actuator 1404.

The shaft interface 1446 defines one or more slots 1458 for guiding an actuating member or pin 1460 into operational association with the valve present sensor 1451. Thus, the actuating member or pin 1460 is generally used to indicate the presence of the multi-position valve 1712 in the valve actuator 1404. The actuating member 1460 includes a plurality of spokes 1461 that cooperate with the slots 1458 in the shaft interface 1446. The actuating member 1460 further includes a distal structure 1462 adapted to coact with the body of the multi-position valve 1712. The engagement of the body of the multi-position valve 1712 with the distal structure 1462 of the actuating member 1460 generally causes the actuating member 1460 to move proximally toward the base support member 1440 and shaft interface 1442 and into operational engagement with the valve present sensor 1451, which preferably initiates a signal to the computer hardware/software associated with the fluid control module 1400 and/or in the injector 1300 indicating the presence of the multi-position valve 1712 in the valve actuator 1404. The proximal movement of the actuating member 1460 causes the spokes 1461 to move into further engagement with the slots 1458 defined in the shaft interface 1446, which allows for the general proximal movement of the actuating member 1460 into the shaft interface 1446.

The distal structure 1462 of the actuating member 1460 cooperates with an adaptor 1464 that is formed to interface with the handle of the multi-position valve 1712. The adaptor 1464 is generally formed to mate with the handle of multi-position valve 1712 and transfer the motor torque from the stepper motor 1442 to the handle to move the handle between the inject, fill, and isolate positions indicated previously. The second multi-position valve 1730 depicted in FIG. 10, discussed previously, shows a conventional stopcock valve with a handle, and is the general type of valve that the valve actuator 1404 is intended to operate in accordance with the present invention. The adaptor 1464 defines a side opening 1465 for receiving the handle of the multi-position valve 1712.

The adaptor 1464 coaxially associates with the distal structure 1462 of the actuating member 1460. Additionally, the adaptor 1464 is adapted to coact with a distal portion 1466 of the shaft interface 1446. The distal portion 1466 of the shaft interface 1446 defines the slots 1458 for receiving the spokes 1461 of the actuating member 1460. The shaft interface 1446 is generally used to transfer the motor torque from the output shaft 1444 to the adaptor 1464 to cause the rotation of the handle of the multi-position valve 1712 to place the multi-position valve 1712 in the respective inject, fill, and isolate positions discussed previously. As shown in FIG. 22, the output shaft 1444 cooperates with a proximal portion 1467 of the shaft interface 1446, and the adaptor 1464 is operationally associated with the output shaft 1444 via the distal portion 1466 of the shaft interface 1446. The shaft interface 1446 is generally adapted to transmit the rotary movement of the output shaft 1444 to the adaptor 1464 via the operational engagement between the distal portion 1466 of the shaft interface 1446 and the adaptor 1464. Thus, the rotary motion of the output shaft 1444 is used to rotate the adaptor 1464 to one of the three operational positions of the multi-position valve 1712 when the stepper motor 1442 is activated. The position signals from the position sensors 1450 may be used to control the operation of the stepper motor 1442 to selectively place the multi-position valve 1712 in one of the three operational positions. In particular, the computer hardware/software associated with the fluid control module 1400 and/or injector 1300 may use the position signals from the position sensors 1450 as input signals and control operation of the stepper motor 1442 based on the information contained in the position signals (i.e., select a desired operational state for the multi-position valve 1412).

The valve actuator 1404 further includes a support assembly 1468 for supporting the multi-position valve 1712 in the valve actuator 1404. The support assembly includes a valve retainer 1469 and a housing 1470 for enclosing and supporting the valve retainer 1469. The valve retainer 1469 includes three snap positions or mounts 1471 adapted to engage the body of the multi-position valve 1712 to secure the multi-position valve 1712 in the valve actuator 1404. The valve retainer 1469 may be formed of a plastic material and the housing 1470 may be formed of a more robust material for protecting the multi-position valve 1712 and may be provided, for example, as a machined aluminum part.

The adaptor 1464 generally extends through a central opening 1472 in the valve retainer 1469 to engage the body of the multi-position valve 1712 and, in particular, receive the handle of the multi-position valve 1712 in the side opening 1465, to operatively associate the multi-position valve 1712 with the actuating components of the valve actuator 1404. The valve retainer 1469 has a proximal engagement structure 1473 that defines the central opening 1472. The engagement structure 1473 coacts with a mating circumferentially-extending edge 1474 on the actuator 1464 so that the axial force associated with inserting the body of the multi-position valve 1712 into the snap positions 1471 is transmitted via the actuator 1464 to the body of the shaft interface 1446 and the base support member 1440. The axial movement associated with inserting the multi-position valve 1712 into the valve retainer 1469 causes the body of the multi-position valve 1712 to contact and engage the distal structure 1462 of the actuating member 1460, thereby causing the actuating member 1460 to move proximally and operatively associate with the valve present sensor 1451. The valve present sensor 1451, once activated, initiates the valve present signal to the fluid control module 1400 and/or injector 1300.

The housing 1470 of the support assembly 1468 may be secured to the shaft interface 1446 and the base support member 1440 using the same mechanical fasteners 1443 used to secure the stepper motor 1442 to the base support member

1440. The housing 1470 preferably defines multiple semicircular cut-outs or recesses 1475 for accommodating the body of the multi-position valve 1712, and generally corresponding to the snap positions or mounts 1471 formed in the valve retainer 1469. The cut-outs or recesses 1475 provide hard stops for the body of the multi-position valve 1712, which are provided to prevent the snap positions or mounts 1471 from becoming over-stressed due to repeated insertions and removals of multi-position valves 1712 into and out of the valve actuator 1404. The valve actuator 1404, after being assembled to include all of the various components discussed hereinabove, may be installed as a unit in the fluid control module 1400.

Generally, when the body of the multi-position valve 1712 is inserted into the valve retainer 1469 and engaged with the snap mounts 1471, the handle of the multi-position valve 1712 is received in the adaptor 1464. The axial force associated with placing the multi-position valve 1712 in the valve retainer 1469 is transmitted via the mating engagement between the engagement structure 1472 on the valve retainer 1469 and the circumferential edge 1474 on the adaptor 1464 to the shaft interface 1446 and the base support member 1440. As the body of the multi-position valve is inserted into the valve retainer 1469, the body engages the distal structure 1462 of the actuating member 1460, causing the actuating member 1460 to move proximally into the shaft interface 1446, with the spokes 1461 of the actuating member 1460 depressing or moving into further engagement with the slots 1458 in the distal portion 1466 of the shaft interface 1446. The axial proximal movement imparted to the actuating member 1460 causes the actuating member 1460 to operatively associate with the valve present sensor 1451, which initiates a valve present signal to the fluid control module and or injector 1300. As shown in FIG. 22, the actuating member 1460 is preferably biased to a non-operative position relative to the valve present sensor 1451 by a biasing member or device such as a spring 1476, so that upon removal of the multi-position valve 1712 from the valve retainer 1469, the actuating member 1460 is moved automatically out of operative association with the valve present sensor 1451.

Figure 24:
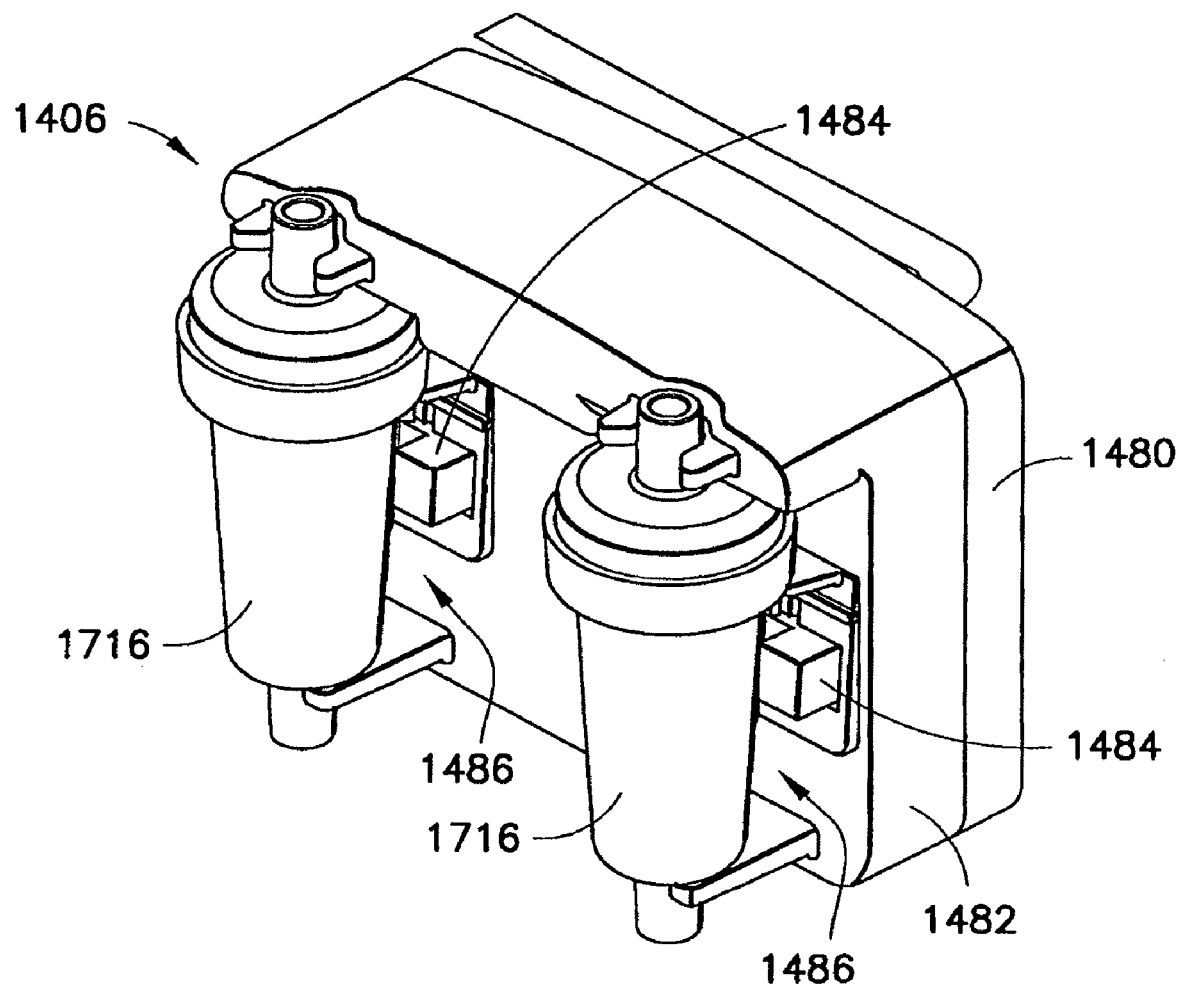
FIG. 24 is a perspective view of a fluid level sensing mechanism of the fluid control module or device shown in FIGS. 20 and 21.
Figure 25:
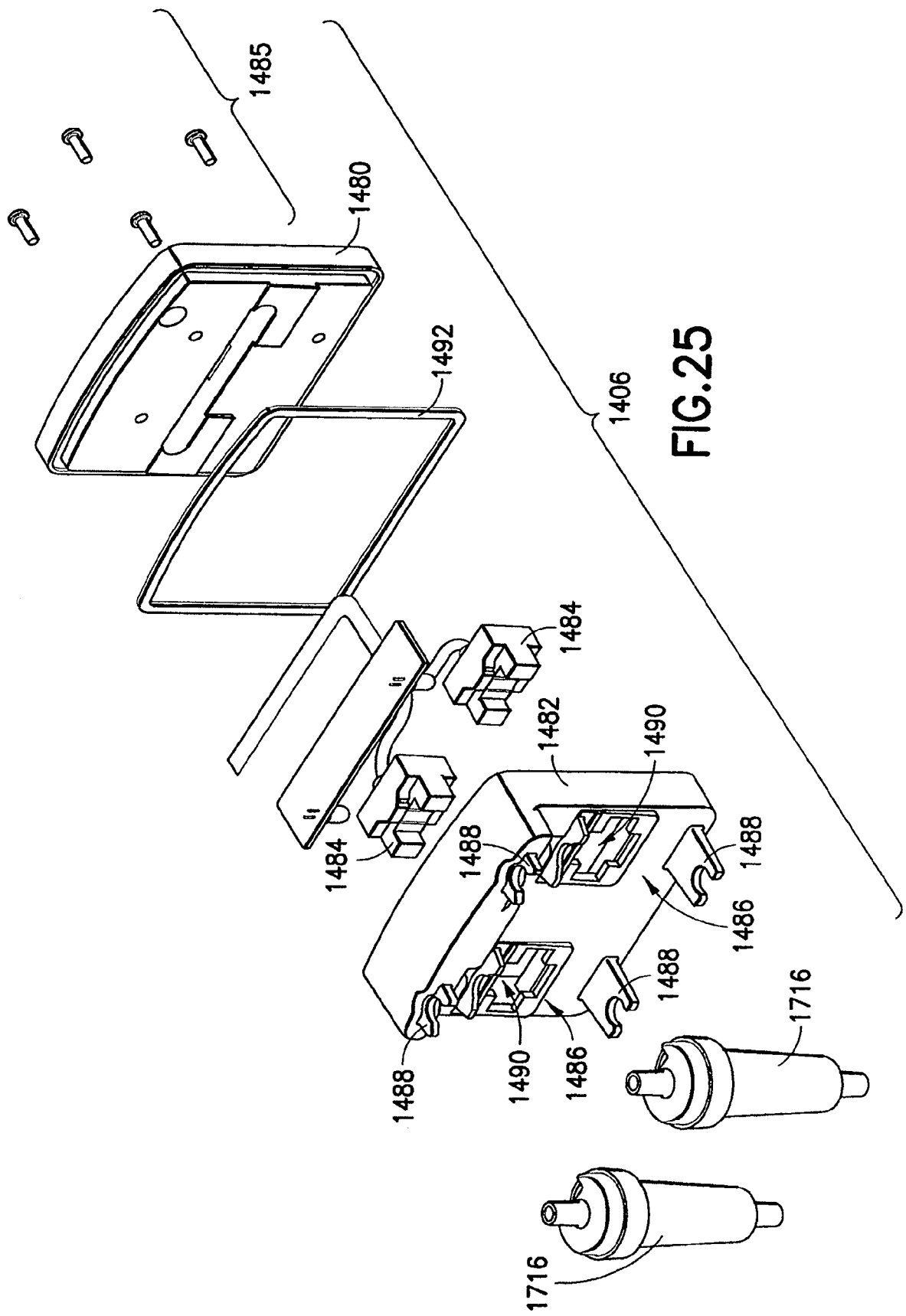
FIG. 25 is an exploded perspective view of the fluid level sensing mechanism of FIG. 24.
Figure 26:
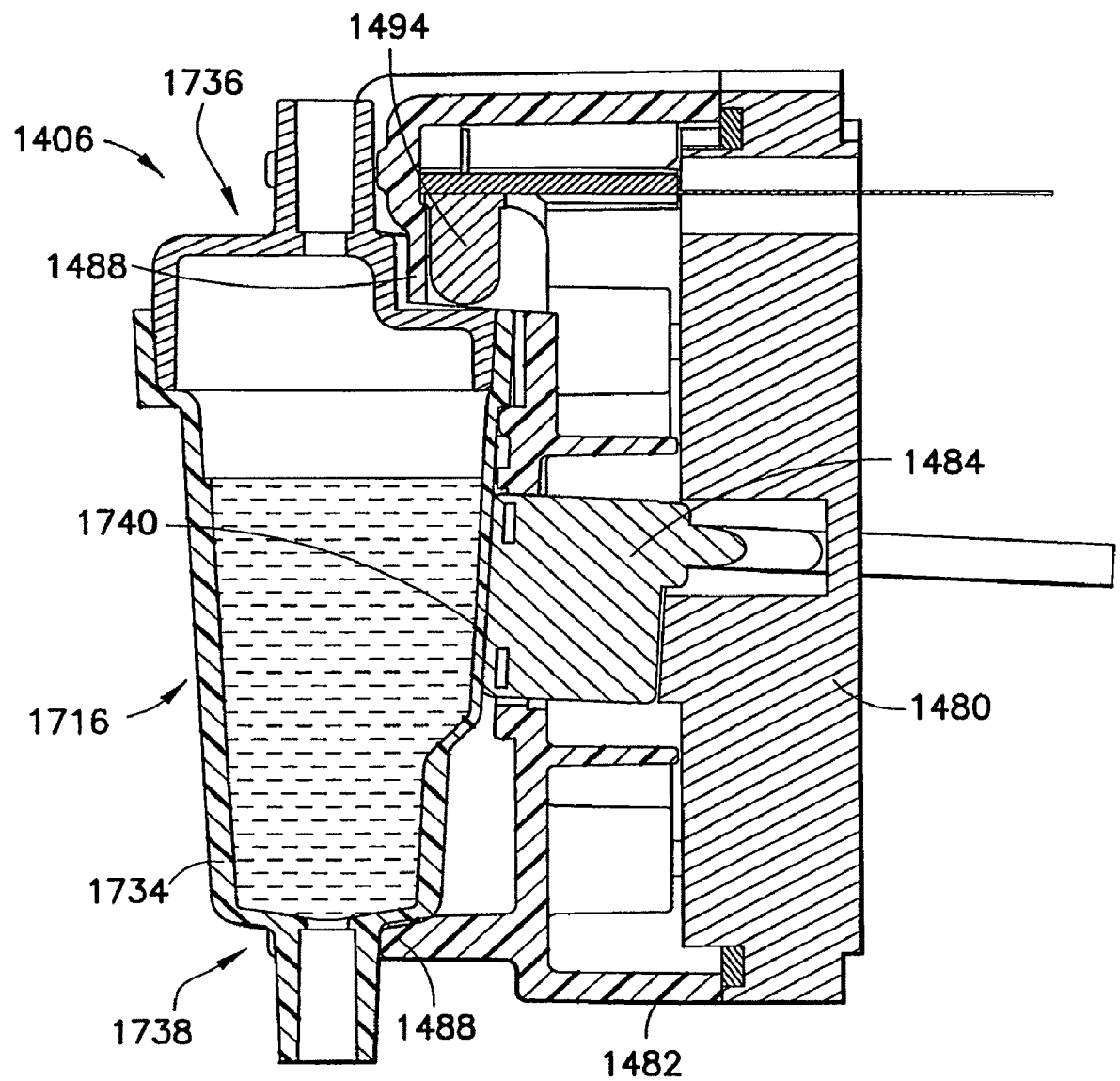
FIG. 26 is a transverse cross sectional view of the fluid level sensing mechanism of FIG. 24.

Referring further to FIGS. 24-26, the fluid level sensing mechanism 1406 (hereinafter "fluid level sensor 1406") provided on the fluid control module 1400 is shown in greater detail. The fluid level sensor 1406 generally interfaces with the drip chambers 1716 associated with the primary and secondary fluid containers 1704, 1706. The fluid level sensor 1406 is provided to indicate to the operator of the fluid delivery system 1200 that sufficient injection fluid, either primary contrast media or secondary saline, is available for an injection or flushing procedure. The fluid level sensor 1406 is generally adapted to indicate to warn the operator when the fluid level in the drip chambers 1716 is below a level sufficient to conduct an injection procedure. The fluid level sensor 1406 is provided as a safety feature to ensure that air in to the fluid path set 1700 during an injection procedure or flushing procedure involving the fluid delivery system 1200.

The fluid level sensor 1406 generally includes a support plate 1480, a drip chamber support 1482, and one or more fluid level sensors 1484 ("hereinafter fluid sensors 1484") which are adapted for association with the drip chambers 1716 connected to the primary and secondary fluid containers 1704, 1706. The support plate 1480 generally supports the various components of the fluid level sensor 1406. The drip chamber support 1482 is generally secured to the support plate 1480 by suitable mechanical fasteners 1485 or another suitable attachment or mounting scheme. The drip chamber support 1482 is preferably a unitary structure that is integrally molded of plastic material, and includes a plurality of attachment or support locations 1486 adapted to support the drip chambers 1716. In particular, the drip chamber support 1482 includes snap mounts or positions 1488 for securing the bodies 1734 of the drip chambers 1716 in the fluid level sensor 1406, and operatively associated with the fluid sensors 1484. The snap mounts 1488 may be adapted to engage inlet and outlet ports of the drip chambers 1716, as shown in FIG. 26.

The drip chamber support 1482 defines respective openings 1490 for receiving the fluid sensors 1484, and associating the fluid sensors 1484 with the drip chambers 1716. The openings 1490 are positioned to allow the fluid sensors 1484 to be operatively associated with the projection 1740 formed on the bodies 1734 of the respective drip chambers 1716. As shown in FIG. 26, the fluid sensors 1484 may physically contact the projections 1740 on the drip chambers 1716, when the drip chambers 1716 are secured in the support locations 1486 on the drip chamber support 1482. The fluid sensors 1484 may be optical or ultrasonic sensors. A suitable ultrasonic sensor for the fluid sensors 1484 is manufactured by Omron. A gasket 1492 may be provided between the drip chamber support 1482 and the support plate 1480 to prevent fluid intrusion between the drip chamber support 1482 and the support plate 1480, which could damage the fluid sensors 1484. Indicator lights 1494 may be associated with the support locations 1486 to illuminate the drip chambers 1716. The indicator lights 1494 are further adapted to visually indicate when the fluid level in the drip chambers 1716 drops to an unsafe level during operation of the fluid delivery system 1200, for example by changing modes to an intermittent mode and blinking to indicate to the operator that insufficient fluid is available for an injection procedure. The indicator lights 1494 provide "back-lighting" for not only the drip chambers 1716 but also the medical tubing associated with the drip chambers 1716, and light the medical tubing and drip chambers 1716 in such a manner that the medical tubing and the drip chambers 1716 form a "light pipe" that illuminates at least part if not all of the first section 1710 of the fluid path set 1700. The back lighting allows the operator of the fluid delivery system 1200 to easily visually inspect the drip chambers 1716 to check the fluid level present in the drip chambers 1716.

The fluid sensors 1484 are generally adapted to provide fluid level signals to the computer hardware/software associated with the fluid control module 1400 and/or injector 1300 to indicate the fluid levels in the drip chambers 1716. The fluid sensors 1484 may be further adapted to initiate an alarm signal to the computer hardware/software associated with the fluid control module 1400 and/or the injector 1300 when the fluid level in the drip chambers 1716 falls to an unsafe level. The computer hardware/software associated with the fluid control module 1400 and/or the injector 1300 may be adapted to respond to the alarm signal by halting the on-going injection procedure.

As FIG. 26 illustrates, the fluid sensors 1484 are tilted or angled at a slight or small angle relative to a vertical axis generally parallel to the face of the support plate 1480. The slight angle, for example 3°, is selected to complement the projection 1740 on the bodies 1734 of the drip chambers 1716. The projection 1740 on the bodies of the drip chambers 1716 is preferably tapered at a small angle, such as 3°. The projection 1740 on the bodies 1734 of the drip chambers 1716 is preferably tapered inward at a small angle from the top end 1736 to the bottom end 1738 on the drip chambers 1716, as illustrated in FIG. 26. The fluid sensors 1784 are positioned in the openings 1490 to compliment the tapered projections 1740 on the respective drip chambers 1716, and preferably physically contact the projections 1740 as indicated previously.

As shown in FIG. 9, the fluid control module 1400 includes a peristaltic pump 1408 that is associated with the secondary fluid container 1706. The peristaltic pump 1408, or an equivalent device, is used to deliver fluid from the secondary fluid container 1706 to a patient typically between fluid injections from the primary fluid container 1704, which are delivered via the syringe 1702 and the injector 1300. The peristaltic pump 1408 is generally adapted to deliver a set flow rate of the secondary fluid, for example saline, to the patient via the second section 1720 of the fluid path set 1700. The peristaltic pump 1408 may be a conventional pump known in the art.

Figure 27:
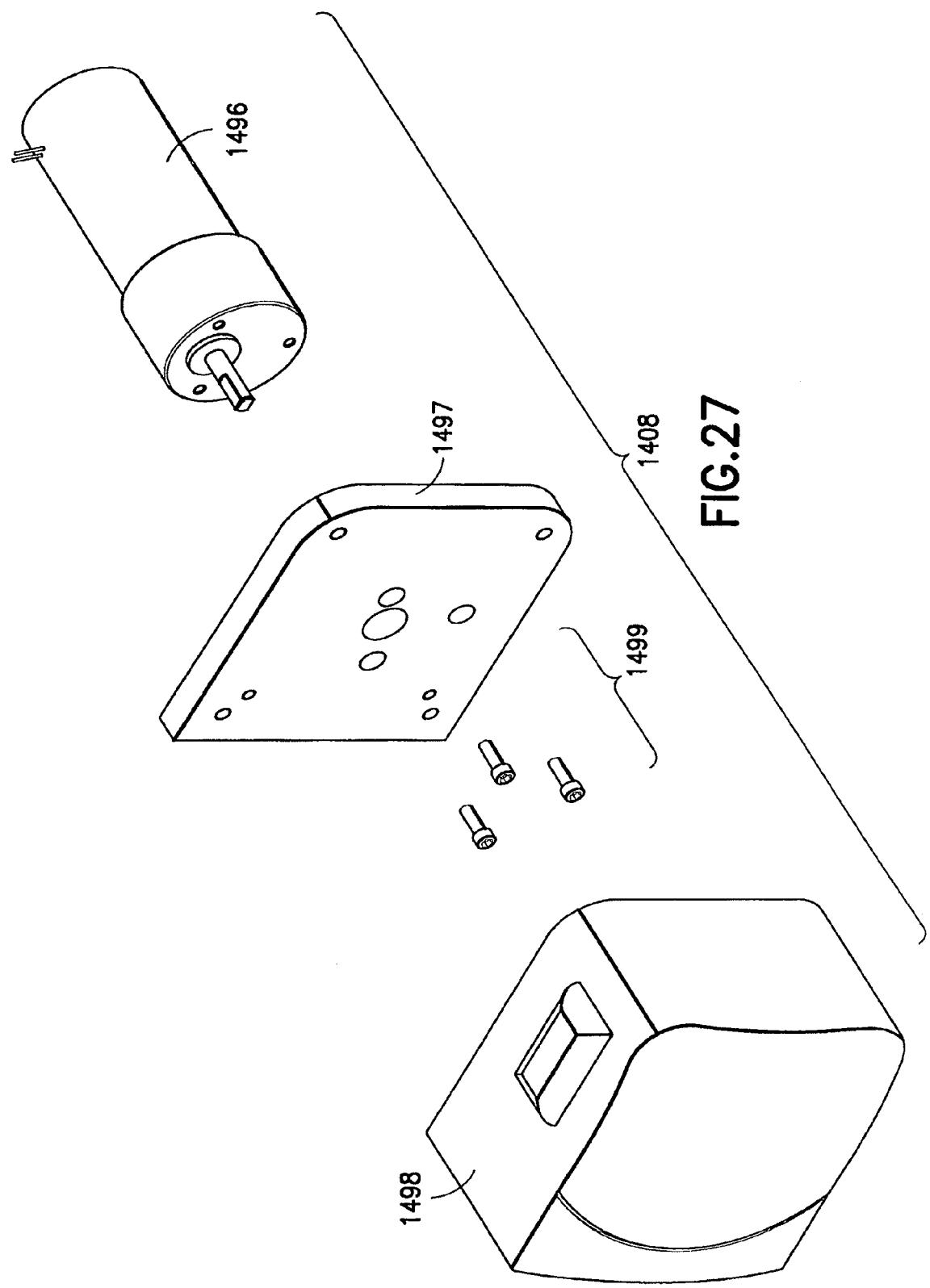
FIG. 27 is an exploded perspective view of a peristaltic pump of the fluid control module or device shown in FIGS. 20 and 21.
Figure 28:
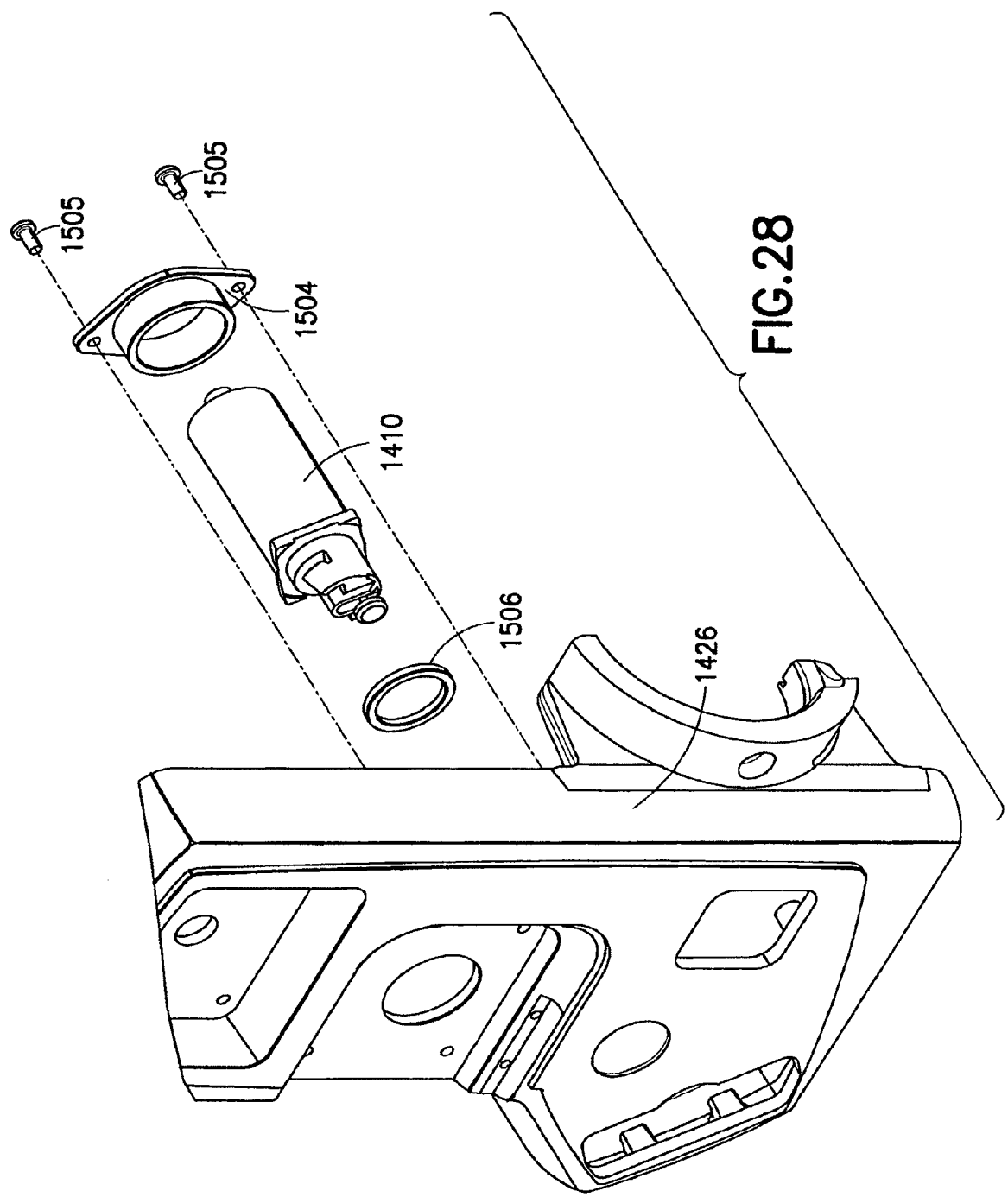
FIG. 28 is an exploded perspective view of a pinch valve assembly of the fluid control module or device shown in FIGS. 20 and 21.

The details of the peristaltic pump 1408 are shown in FIGS. 9, 27, and 28. Generally, the peristaltic pump 1408 includes a pump head 1496, a base plate 1497 for mounting the pump head 1496 to the front portion or side 1426 of the housing 1402, and an enclosure or door structure 1498 for enclosing the pump head 1496. Mechanical fasteners 1499 may be used to secure the pump head 1496 to the base plate 1497, and may further be used to secure the base plate 1497 to the front side 1426 of the housing 1402.

Figure 20:
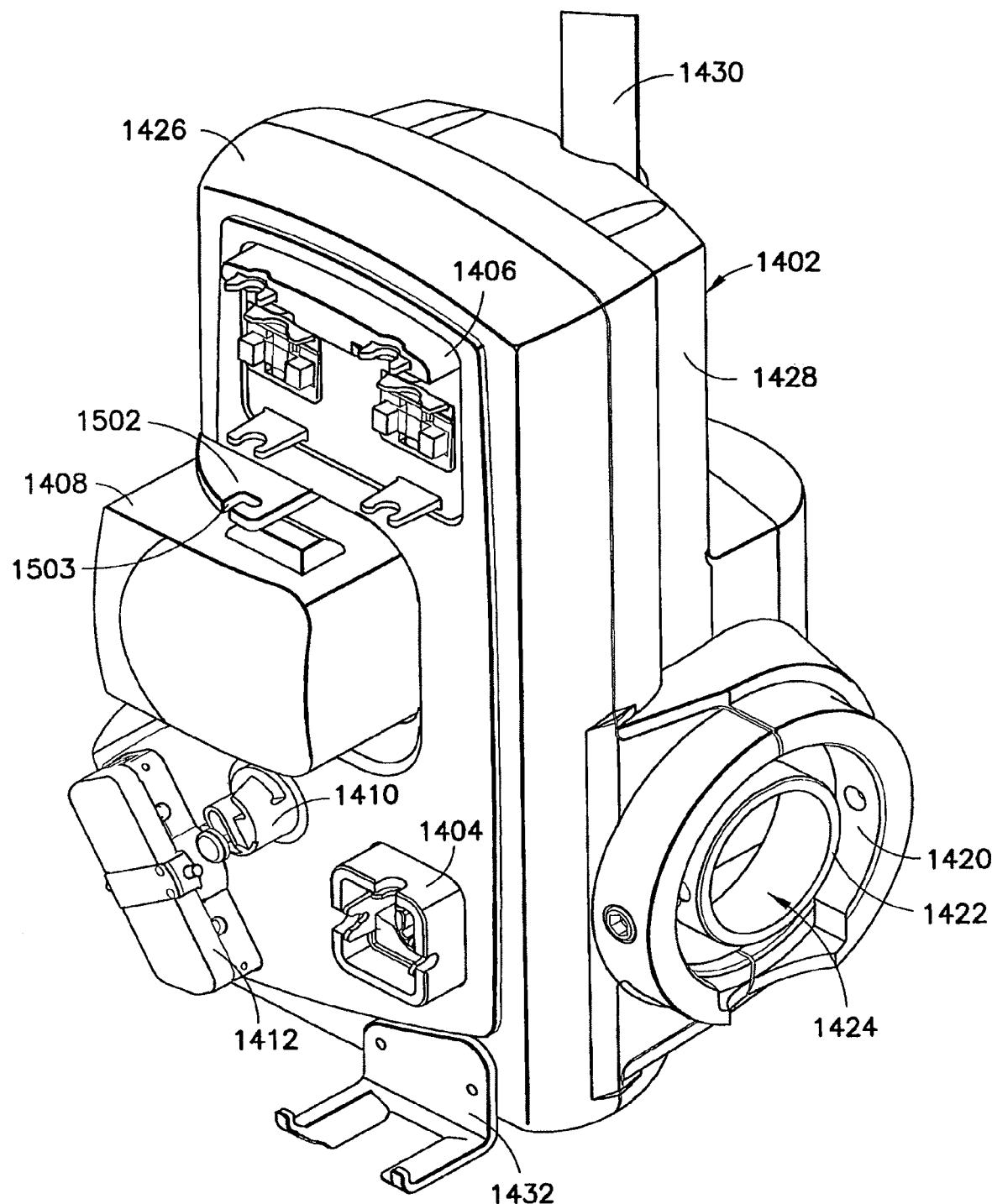
FIG. 20 is a perspective view of a fluid control module or device in accordance with the present invention.
Figure 21:
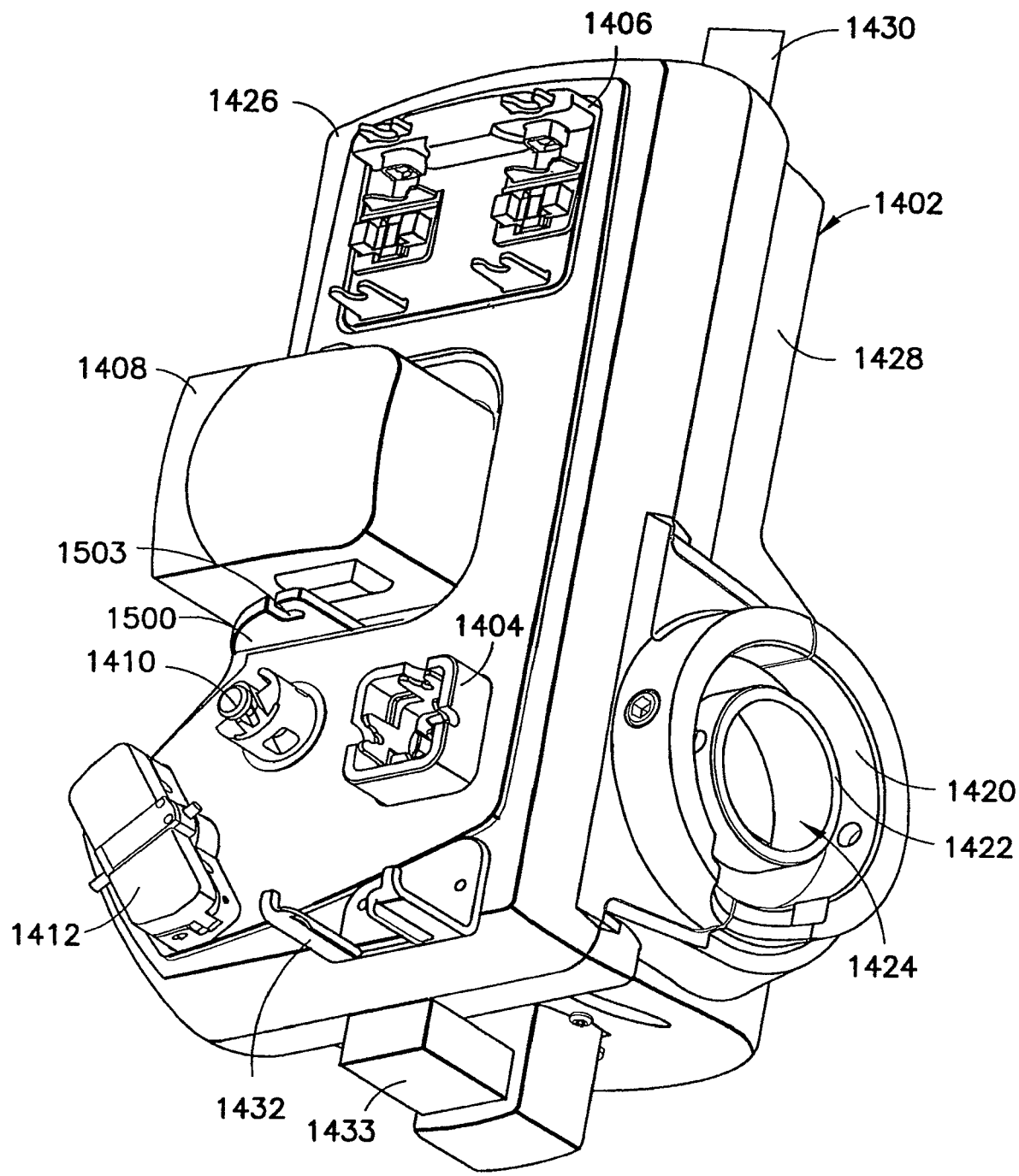
FIG. 21 is a second perspective view of the fluid control module or device shown in FIG. 20.

As shown in FIGS. 20 and 21, the front side 1426 of the housing 1402 preferably includes opposing guides 1500, 1502 located above and below the peristaltic pump 1408 for securing medical tubing generally used to connect the secondary fluid container 1706 to the second section 1720 of the fluid path set 1700 via the peristaltic pump 1408. In particular, with particular reference to FIG. 10, the output line 1718 from the drip chamber 1716 associated with the secondary fluid container 1706 is associated with the peristaltic pump 1408, and may be secured in operative engagement with the peristaltic pump 1408 using the opposing guides 1500, 1502. The guides 1500, 1502 may be integrally formed with the front side or portion 1426 of the housing 1402 and generally define L-shaped slots 1503, which are generally adapted to receive the medical tubing forming the output line 1718. FIG. 9 illustrates the use of the guides 1500, 1502, with the medical tubing extending from the secondary fluid container 1706 and associated with peristaltic pump 1408 received in the guides 1500, 1502 in accordance with the present invention. The door structure 1498 of the peristaltic pump 1408 may be adapted to prevent gravity flow from the secondary fluid container 1706 when the peristaltic pump 1408 is not in operation, and further secures the output line 1718 in operative association with the pump head 1496, as is conventional in the art.

Referring further to FIG. 28, the shut-off or pinch valve 1410 of the fluid control module 1400 is shown. The pinch valve 1410 is provided downstream of the peristaltic pump 1408 and is used as back-up fluid shut-off mechanism to discontinue fluid flow to the second section 1720 of the fluid path set 1700 when the peristaltic pump 1408 ceases operation. The pinch valve 1410 is adapted to open for fluid flow during operation of the peristaltic pump 1408, and is further adapted to automatically close when the peristaltic pump 1408 ceases operation to prevent air from being introduced into the second section 1720 of the fluid path set 1700. The pinch valve 1410 generally prevents gravity flow to the second section 1720 of the fluid path set 1700 when the peristaltic pump 1408 is not in operation, and is generally provided as a back-up shut-off mechanism to the peristaltic pump 1408. The pinch valve 1410 may be a conventional pinch valve, such as that manufactured by Acro Associates. The pinch valve 1410 is mounted to the front side or portion 1426 of the housing 1402 by a bracket 1504 and mechanical fasteners 1505. A gasket 1506 may be used to seal the connection between the pinch valve 1410 and the front side or portion 1426 of the housing 1402.

Figure 29:
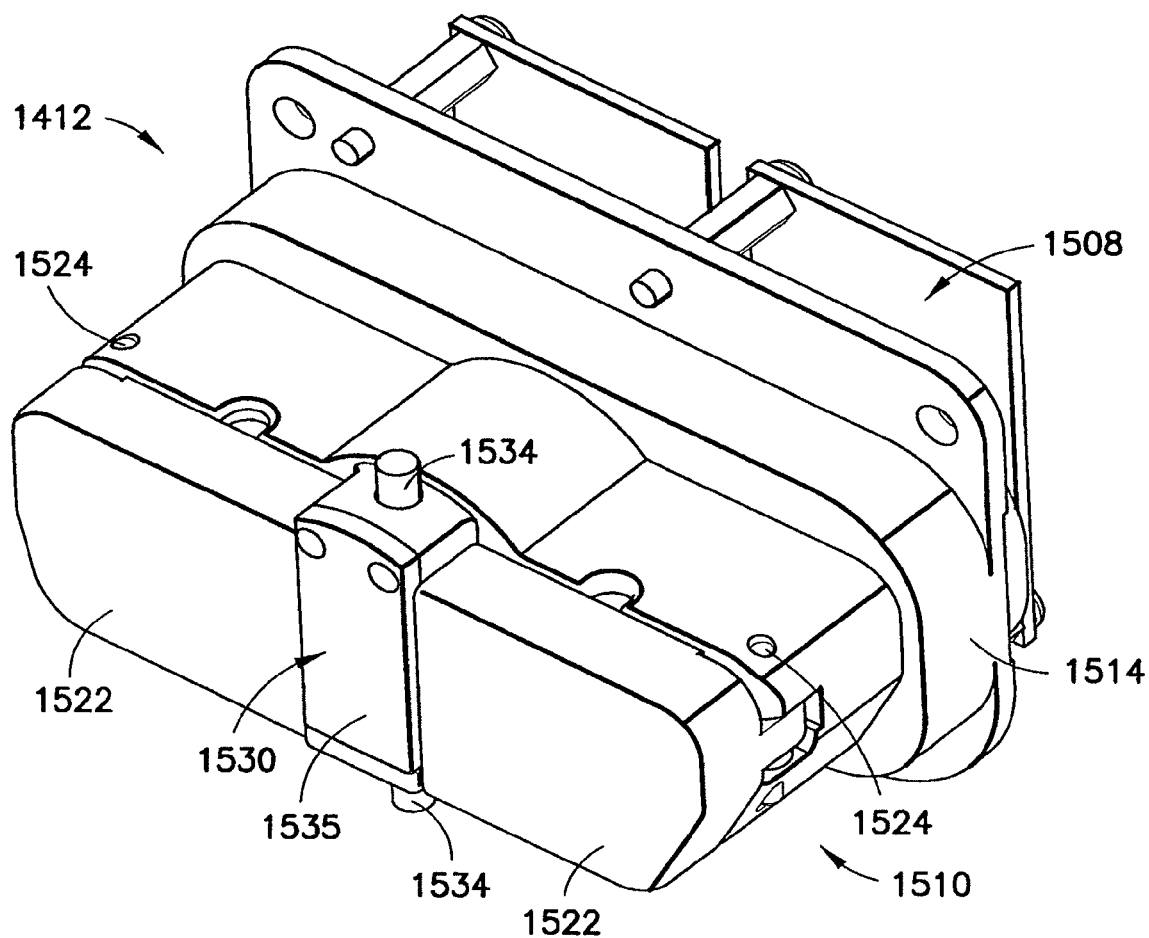
FIG. 29 is a perspective view of an air detector assembly of the fluid control module or device shown in FIGS. 20 and 21.
Figure 30:
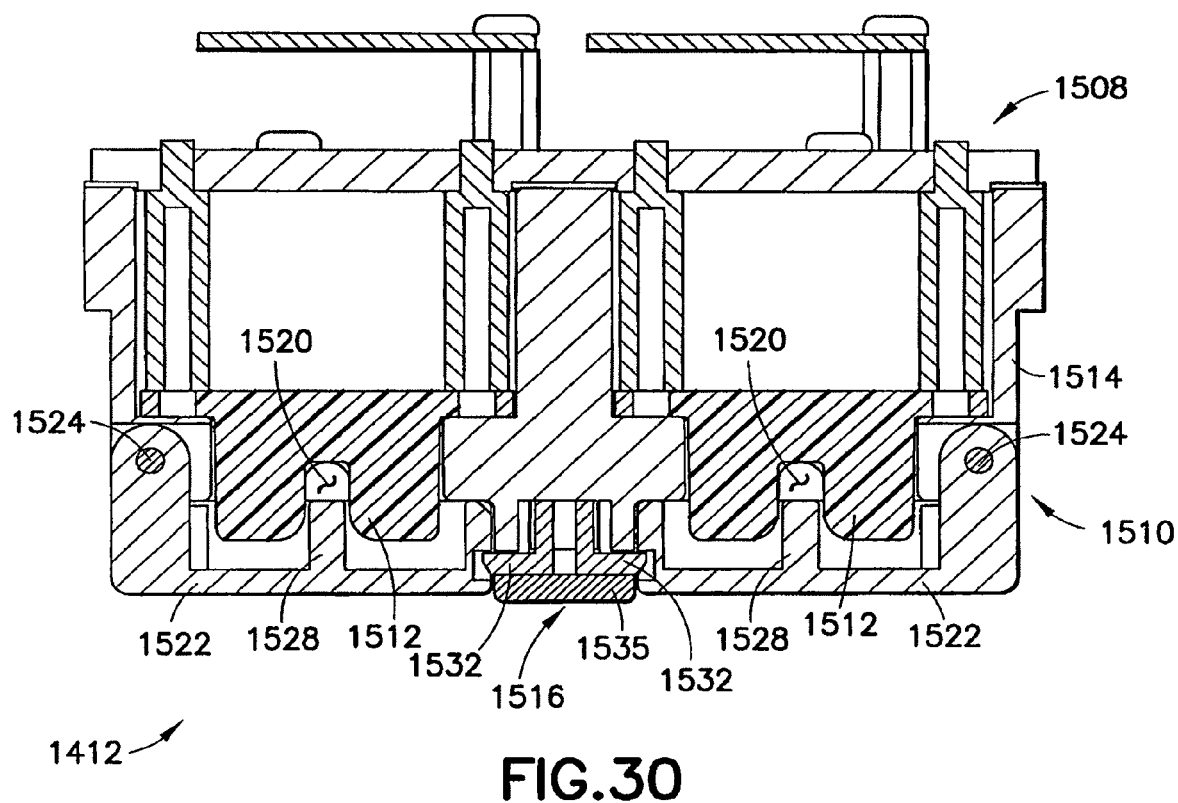
FIG. 30 is a longitudinal cross sectional view of the air detector assembly of FIG. 29.
Figure 31:
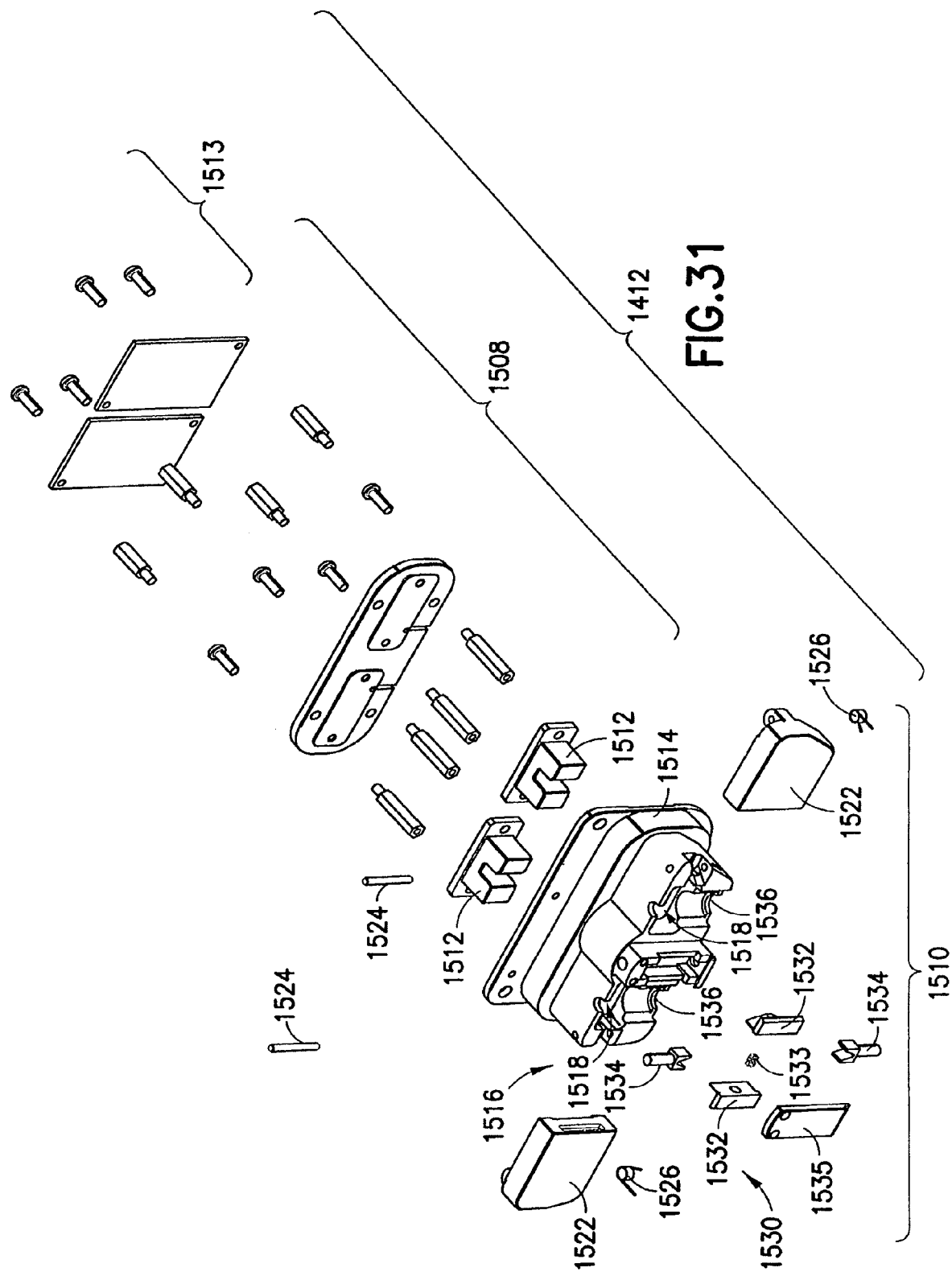
FIG. 31 is an exploded perspective view of the air detector assembly of FIGS. 29 and 30.

Referring further to FIGS. 29-31, the air detector assembly 1412 of the fluid control module 1400 is shown in greater detail. The air detector assembly 1412 is adapted to detect gross air columns that may be present in the output line 1718 connected to the drip chamber 1716 associated with the secondary fluid container 1706, and the output line 1719 associated with the multi-position valve 1712. The air detector assembly 1412 is generally adapted to initiate a signal to the computer hardware/software associated with the fluid control module 1400 and/or injector 1300, if gross air is detected in the medical tubing forming the output line 1719 associated with the multi-position valve 1712 or in the medical tubing forming the output line 1718 and further associated with the peristaltic pump 1408. The fluid control module 1400 and injector 1300 are preferably adapted to discontinue any ongoing fluid injection procedures if the air detector assembly 1412 detects gross air in the output line 1718 or the output line 1719.

The air detector assembly 1412 generally includes a sensor section 1508 and a retaining device 1510 for securing the medical tubing forming the output line 1718 and output line 1719. The sensor section 1508 generally includes two air column detectors 1512 adapted to detect the presence of gross air in the medical tubing secured by the retaining device 1510. The air column detectors 1512 may be conventional air detectors such as those manufactured by Zevex. The sensor section 1508 may be secured to the retaining device 1510 with mechanical fasteners 1513.

The retaining device 1510 is generally adapted to secure the medical tubing forming the output line 1718 and output line 1719 in operative association with the air column detectors 1512. The retaining device 1510 generally includes a base 1514 and a closure assembly 1516 associated with the base 1514. The sensor section 1508 is secured to the base 1514 with the mechanical fasteners 1513. The base 1514 defines two front openings 1518 for receiving the air column detectors 1512 and associating the air column detectors 1512 with the medical tubing. The air column detectors 1512 each define a recess 1520 for receiving the medical tubing, as shown in FIG. 30.

The closure assembly 1516 is generally adapted to secure the engagement of the medical tubing in the recesses 1520 in the air column detectors 1512. The closure assembly 1516 is formed by two closure members or doors 1522, which are generally adapted to move from a closed position securing the medical tubing in the recesses 1520, to an open position permitting removal or disengagement of the medical tubing from the recesses 1520. The closure members 1522 are pivotally connected to the base 1514 by pins 1524, and are preferably biased to the open position by respective torsion springs 1526 associated with the pins 1524. The closure members 1522 may include projections 1528 that cooperate at least partially with the recesses 1520 in the air column detectors 1512 to secure the medical tubing in the recesses 1520 when the closure members 1522 are in the closed position. The closure members 1522 are preferably formed of a substantially clear plastic material to permit viewing of the medical tubing in the recesses 1520 when the closure members 1522 are in the closed position.

A releasable locking mechanism or device 1530 may be associated with the retaining device 1510 for securing the closure members 1522 in the closed position. The locking mechanism 1530 is provided to counteract the biasing force of the torsion springs 1526. The locking mechanism 1530 includes two sliders 1532 that are spring-loaded by a spring 1533. The closure members 1522 generally engage the sliders 1532, as shown in FIG. 30, and push against the spring-force to allow the closure members 1522 to move past the sliders 1532, and then allow the sliders 1532 to engage the closure members 1522 to hold the closure members 1522 in the closed position. The sliders 1532 may be retracted against the spring-force by two buttons 1534 located on opposing sides of the base 1514. By depressing the buttons 1534, the sliders 1532 are retracted, which allows the closure members 1522 to spring open under the biasing force of the torsion springs 1526. A cover plate 1535 may enclose the sliders 1532 of the locking mechanism 1530.

The base 1514 may include recessed structures 1536 located below the front openings 1518 that are adapted to engage the first and second connector members 1774, 1776 of the connectors 1708 in the fluid path set 1700 when the closure members 1522 are in the closed position. In particular, the closure members 1522 generally secure the first and second connector members 1774, 1776 to the recessed structures 1536 when the closure members 1522 are in the closed position, thereby preventing their movement when the first and second connector members 1774, 1776 being joined and allowing one-handed connection of these parts. The recessed structures 1536 are adapted to engage the bodies of the first and second connector members 1774, 1776, so that first and second connector members 1774, 1776 in the connectors 1708 of the fluid path set 1700 may be joined or connected with a one-handed operation. Thus, the recessed structures 1536 are generally adapted to prevent rotation of the first and second connector members 1774, 1776 when engaged with the recessed structures 1536, so that the corresponding mating components to be connected to the "engaged" first or second connector member 1774, 1776 may be joined to the engaged first or second connector member 1774, 1776 without having to use two hands to manipulate the opposing connecting members.

The installation and operation of the fluid delivery system 1200 will now be discussed. Prior to turning on the fluid delivery system 1200, a source of power, such as 110 or 220 volts of electricity sent through a line cord from a wall socket (not shown) is provided to the fluid delivery system 1200. Thereafter, the operator turns on a master power switch (not shown), preferably situated on either the fluid control module 1400 or the injector 1300 of the fluid delivery system 1200. The fluid delivery system 1200 responds through visual indicia, such as the illumination of a green light (not shown) on the fluid control module 1400 or the injector 1300, to indicate that the fluid delivery system 1200 is in a powered-up state. The operator then turns on the user display 210 (See FIG. 2) via a user display switch (not shown). It is to be understood that the user display 210 may be turned on prior to the fluid delivery system 1200. After power has been supplied to the user display 210, the fluid delivery system 1200 responds by undergoing various self-diagnostic checks to determine if the fluid delivery system 1200 exhibits any faults or conditions that would prevent proper operation of the fluid delivery system 1200. If any of the self-diagnostic checks fail and/or a fault is detected in the fluid delivery system 1200, a critical error window or screen is displayed on the user display 210, which may instruct the operator to contact service personnel to remedy the fault or instruct the operator on how to remedy the fault himself or herself. Additionally, the fluid delivery system 1200 will not allow an operator to proceed with an injection if any of the self-diagnostic checks have failed. However, if all self-diagnostic checks are passed, the fluid delivery system 1200 proceeds to display a main control screen on the user display 210.

The main control screen includes various on-screen controls, such as buttons, that may be accessed by the operator via the touch-screen of the user display 210. The on-screen controls may include, but are not limited to, selectable options, menus, sub-menus, input fields, virtual keyboards, etc. The operator may therefore utilize the touch-screen of the user display 210 to program one or more injection cycles of the fluid delivery system 1200, and to display performance parameters. It is to be understood that input to the user display 210 may also be accomplished by providing an on-screen cursor and external pointing device, such as a trackball or mouse, that is operatively associated with the on-screen cursor. It is to be understood that the operator may stop any automatic functions of the fluid delivery system 1200 by touching an "Abort" button or anywhere on the user display 210.

Desirably, the main control screen includes a "New Case Setup" button, that when touched, initiates a "New Case Setup" screen to be displayed on the user display 210. In a practical sense, a "new case" is representative of one or more injections for a specific patient and, therefore, having specific parameters inputted and associated therewith. The operator touches the "New Case Setup" button and, subsequently, the resultant "New Case Setup" screen displays a "Multi-Patient Syringe" button. After touching the "Multi-Patient Syringe" button, the operator is presented with a screen displaying a "Retract" button and an "Engage Plunger" button displayed thereon. The operator touches the "Retract" button and the fluid delivery system 1200 retracts the piston associated with the injector 1300. The operator may then remove the syringe 1702 from its package, orient the syringe 1702 to fit the pressure jacket assembly of the injector 1300, and place the syringe 1702 into the pressure jacket of the pressure jacket assembly. During the course of the syringe installation, the "Multi-Patient Syringe" screen remains on the user display 210. Thus, after loading the syringe 1702 properly in the pressure jacket assembly, the operator touches the "Engage Plunger" button, which causes the injector piston to move forward. The fluid delivery system 1200 continues to move the injector piston forward until the injector piston engages the syringe plunger in the syringe 1702, and mechanically locks thereto. An audible clicking noise is produced to indicate a secure coupling between the injector piston and the syringe plunger. Thereafter, the syringe plunger travels the length of the syringe 1702 to the distal end of the syringe 1702. The fluid delivery system 1200 may provide visual feedback of this action to the operator via the user display 210. Thereafter, the operator rotates the injector head of the injector 1300 into an upright position to allow any air to collect at the distal end of the syringe 1702 when the syringe 1702 is subsequently filled. The user display 210 then reverts to the "New Case Setup" screen.

The fluid delivery system 1200 is now ready to accept the installation of the first section 1710 of the fluid path set 1700. Specifically, the operator removes the first section 1710 from its package. The first section 1710 is preferably provided in a sterile condition in the package. The operator then touches a "Multi-Patient Section" button, which causes the user display 210 to show an image of the fluid control module 1400, bottle holders (i.e., primary and secondary fluid containers 1704, 1706), and injector 1300, with an overview of the first section 1710 highlighted in relation to these components. Additionally, the user display 210 also displays an "Install Saline" and an "Install Contrast" button. The operator touches the "Install Saline" button, which causes an enumerated list of actions corresponding to enumerated sections of the image relating to the first section 1710 of the fluid path set 1700, and connecting the first section 1710 to the secondary fluid container 1706, which typically contains saline. This enumerated list may include, but is not limited, to actions such as (1) Install saline tubing (which is depicted as a button); (2) Spike saline; (3) Fill drip chamber; and (4) Finish with saline. Thereafter, the fluid control module 1400 opens the pinch valve 1410. Next, the operator installs the saline container (i.e., secondary fluid container 1706). The operator now installs the drip chamber 1716 associated with the secondary fluid container 1706 into place, and then opens the peristaltic pump 1408. The operator then routes the medical tubing forming the output line 1718 from the drip chamber 1716 through the peristaltic pump 1408 into the pinch valve 1410 and into the air detector assembly 1412. Then, the operator closes the peristaltic pump 1408. The text on the "Close Saline Tubing" button changes to read "Install Saline Tubing." Then, the operator spikes the secondary fluid container 1706 with spike 1717, fills the drip chamber 1716 by squeezing or "priming" it, and touches a "Complete" button. The fluid control module 1400 now closes the pinch valve 1410. The user display 210 may provide visual indicia, such as a darkening of the saline portion, to indicate that the saline installation is completed successfully. Then, the operator touches the "Install Contrast" button, which causes an enumerated list of actions corresponding to enumerated sections of the image relating to the contrast to be displayed. This enumerated list may include, but is not limited to actions such as: (1) Install contrast (which is depicted as a button); (2) Attach high pressure line (i.e., input line 1721) to syringe; (3) Spike contrast; (4) Fill drip chamber; and (5) Finish with contrast. Accordingly, the operator hangs the contrast bottle (i.e., primary fluid container 1704) and touches the "Install Contrast" button. Thereafter, the fluid control module 1400 turns the valve actuator 1404 to the inject position. The operator now installs the drip chamber 1716 associated with the primary fluid container 1706 in place in the fluid level sensing mechanism 1406, the multi-position valve 1712 in the valve retainer 1469 in the housing 1470, and the output line 1718 in the air detector assembly 1412. Then, the operator closes the air detector assembly 1412. Thereafter, the operator attaches the high pressure input line 1721 to the multi-position valve to the syringe 1702. Next, the operator spikes the primary fluid container 1704, fills the drip chamber 1716 by squeezing or "priming" it, and touches a "Complete" button. The user display 210 may provide visual indicia, such as a darkening of the contrast portion, to indicate that the contrast installation is completed. It is to be understood that the installation of the "contrast portion" and "saline portion" of the first section 1710 may be performed in parallel instead of serially. Furthermore, the order of installation between the contrast portion and the saline portion of the first section 1710 may be reversed. Moreover, the internal sequence for installing the contrast portion and the saline portion may vary in numerous ways in accordance with the present invention.

The syringe 1702 may now be initially filled with contrast media from the primary fluid container 1706. Specifically, the operator touches a "Fill Contrast" button on the user display 210, which causes the fluid delivery system 1200 to enter an auto-fill mode, and to place the multi-position valve 1712 in the fill position. After verifying that there is sufficient contrast media in the contrast drip chamber 1716 to initiate the fill process, the fluid delivery system 1200 moves the injector piston proximally at a controlled rate, such as 3 mL/s, which causes contrast media to be drawn from the primary fluid container 1704. The fluid delivery system 1200 may provide visual feedback of this action to the operator via the user display 210. Thus, the fluid delivery system 1200 may display on the user display 210 the current volume in the syringe 1702 based upon the position of the injector piston. The fluid delivery system 1200 proceeds to draw contrast until a predetermined event occurs, such as the total remaining volume in the syringe 1702 reaches a preset or pre-chosen amount or the contrast media volume in the primary fluid container 1706 is depleted completely. The multi-position valve 1712 is then turned to the closed or isolate position by the fluid delivery system 1200.

The fluid delivery system 1200 is now configured to undergo a purge of any air in the tubing of the first section 1710 of the fluid path set 1700. Specifically, the operator removes the protective caps 1798 from the first section 1710. Thereafter, the operator touches a "Purge Contrast" button on the "New Case Setup" screen, which causes the fluid delivery system 1200 to move the multi-position valve 1712 to the inject position. Then, the fluid delivery system 1200 moves the injector piston forward at a predetermined rate, such as 1.0 to 1.5 mL/s, which causes any gas or liquid to be discharged from the syringe 1702, and the first section 1710. The operator ensures that the discharged fluid is caught manually in a suitable container. After the operator is satisfied that all or most of the visible air is discharged, the operator touches the "Purge Contrast" button again to stop the purge. However, if the operator does not manually stop the purge, the fluid delivery system 1200 may stop the purge automatically, for example, once 5 mL of liquid or air is purged, based upon the relative injector piston movement. The operator may facilitate the removal of any remaining trapped air by tapping the body of the pressure jacket, joints, valves, and medical tubing in the first section 1710. It is to be understood that the purging operation may be repeated as necessary to ensure that all air is expelled from the syringe 1702 and the first section 1710. Thereafter, the operator touches a "Complete" button, which causes the multi-position valve 1712 to move to the closed or isolate position, thereby stopping the flow of contrast media. The fluid delivery system 1200 then causes the user display 210 to return to the "New Case Setup" screen. The operator may now install a new set of protector caps 1798 to the exposed ends of the first section 1710.

The fluid delivery system 1200 now may undergo a purge of any air in the saline portion of the first section 1710. Specifically, the operator touches a "Purge Saline" button on the "New Case Setup" screen, which causes the fluid delivery system 1200 to open the pinch valve 1410, and turn on the peristaltic pump 1408. Saline from the secondary fluid container 1706 begins to drip at a predetermined flow rate, such as 1.25 mL/s, which causes any gas or liquid to be discharged from the first section 1710. The operator ensures that the discharged fluid is caught manually in a suitable container. After the operator is satisfied that all or most of the visible air is discharged, the operator touches the "Purge Saline" button again to stop the purge. However, if the operator does not manually stop the purge, the fluid delivery system 1200 may stop the purge automatically after, for example, 5 seconds have passed since the initiation of the purge. The operator may facilitate the removal of any remaining trapped air by manually tapping the joints, valves, and tubing in the first section 1710. It is to be understood that the purging operation may be repeated as necessary to ensure that substantially all air, particularly gross air, is expelled from the first section 1710. Thereafter, the operator touches a "Complete" button, which causes the user display 210 to return to the "New Case Setup" screen. It is to be understood that the order of purging the contrast and saline portions of the first section 1710 may be reversed.

At this point, the fluid delivery system 1200 is ready to accept the installation of the second section 1720 of the fluid path set 1700. Specifically, the operator removes the protector caps 1798 from the first section 1710 and removes the second section 1720 from its package. Then, the operator may secure the patient end of the second section 1720 to an imaging table or other securing point. The operator then removes the protector caps 1798 from the second section 1720. Thereafter, the operator connects the connectors 1708 associated with the first and second sections 1710, 1720 to fluidly connect these sets or sections. In particular, the operator attaches the male connector of the low-pressure saline tubing to the female connector of the first section 1710 and attaches the female contrast connector of the high-pressure contrast tubing to the male connector of the first section 1710. It is to be understood that the order of connecting the low pressure saline tubing and the high pressure contrast tubing to their respective connectors 1708 may be reversed. The operator may now optionally place a sterile cover (not shown) on the user display 210 to maintain a sterile environment.

The fluid delivery system 1200 is now configured to undergo a purge of any air in both the contrast portion (i.e., contrast lines), and saline portion, (i.e., saline lines), of the first section 1710 and the second section 1720. To purge the air in the contrast portion, the operator removes a cap (not shown) on the pressure isolation port 1761. The operator then touches the "Purge Contrast" button on the user display 210, which causes the fluid delivery system 1200 to move the multi-position valve 1712 to the inject position. The contrast begins to flow through the contrast tubing, to fill the pressure isolation mechanism 1722, and then to flow out of the pressure isolation port 1761. The operator then touches the "Purge Contrast" button again to stop the purge. However, if the operator does not manually stop the purge, the fluid delivery system 1200 may stop the purge automatically, once a predetermined amount, for example 5 mL, of fluid or air is purged, based upon the relative piston movement. When the purge is complete, the fluid delivery system 1200 moves the multi-position valve 1712 to the closed position. The operator then attaches a pressure transducer (See FIGS. 7B-7F) or line to the pressure isolation port 1761. The operator initiates a contrast purging by touching the "Purge Contrast" button on the user display 210, which causes the fluid delivery system 1200 to move the multi-position valve 1712 to the inject position. The contrast begins to flow through the pressure isolation port 1761 and pressure transducer. Subsequently, the operator turns the transducer multi-position valve 1712 to the inject position. The fluid delivery system 1200 then moves the injector piston forward at a predetermined rate, such as 1.0 to 1.5 mL/s, which causes any gas or liquid to be discharged from the syringe 1702, first section 1710, and the second section 1720. The operator ensures that the discharged fluid is caught manually in a suitable container. After the operator is satisfied that all or most of the visible gross air is discharged, the operator touches the "Purge Contrast" button again to stop the purge. However, if the operator does not manually stop the purge, the fluid delivery system 1200 may stop the purge automatically, once a predetermined amount, for example 5 mL, of fluid or air is purged, based upon the relative piston movement. When the purge is complete, the fluid delivery system 1200 moves the multi-position valve 1712 to the closed position. The operator may facilitate the removal of any remaining trapped air by manually tapping the pressure isolation mechanism 1722, connectors, valves, and tubing in both the first section 1710 and the second section 1720, and adjusting the second multi-position valve 1730 as necessary. It is to be understood that the purging operation may be repeated as necessary to ensure that all gross air has been expelled from the fluid path set 1700.

To purge the air in the saline portion, the operator touches the "Purge Saline" button, which causes the fluid delivery system 1200 to open the pinch valve 1410 and turn on the peristaltic pump 1408. Saline from the secondary fluid container 1706 begins to drip at a predetermined flow rate, such as 1.25 mL/s, which causes any air in the saline portion of the fluid path set 1700 to be expelled. The operator ensures that the discharged saline is manually caught in a suitable container. After the operator is satisfied that all or most of the visible air is discharged, the operator touches the "Purge Saline" button again to stop the purge. However, if the operator does not manually stop the purge, the fluid delivery system 1200 may stop the purge automatically after, for example, 5 seconds have passed since the initiation of the purge. The operator may facilitate the removal of any remaining trapped air by manually tapping the various components of the fluid path set 1700 in the manner discussed previously. It is to be understood that the purging operation may be repeated as necessary to ensure that all air is expelled from the fluid path set 1700. Thereafter, the operator touches the "Complete" button, which causes the display to return to the "New Case Setup" screen. It is to be understood that the order of purging the contrast portion and then the saline portion of the fluid path set 1700, may be reversed.

The fluid delivery system 1200 may be configured to allow an operator to purge the contrast and saline portions of the fluid path set 1700 line by utilizing the hand controller 400 as opposed to solely utilizing the on-screen controls. Furthermore, it is to be understood that the hand controller 400 may be connected to the fluid control module 1400 at any time during the installation of the fluid delivery system 1200. Specifically, the connector end of the hand controller connector secures to the hand controller plug of the fluid control module 1400. Connection of the hand controller 400 may cause an icon representing the connected hand controller 400 to be displayed on the user display 210. A preferred embodiment of the hand controller 400 is disclosed in U.S. Patent Application Ser. No. 60/560,496, filed Apr. 8, 2004, and entitled HAND HELD CONTROL DEVICE FOR A FLUID DELIVERY SYSTEM, the contents of which are incorporated herein by reference in its entirety.

Figure 34:
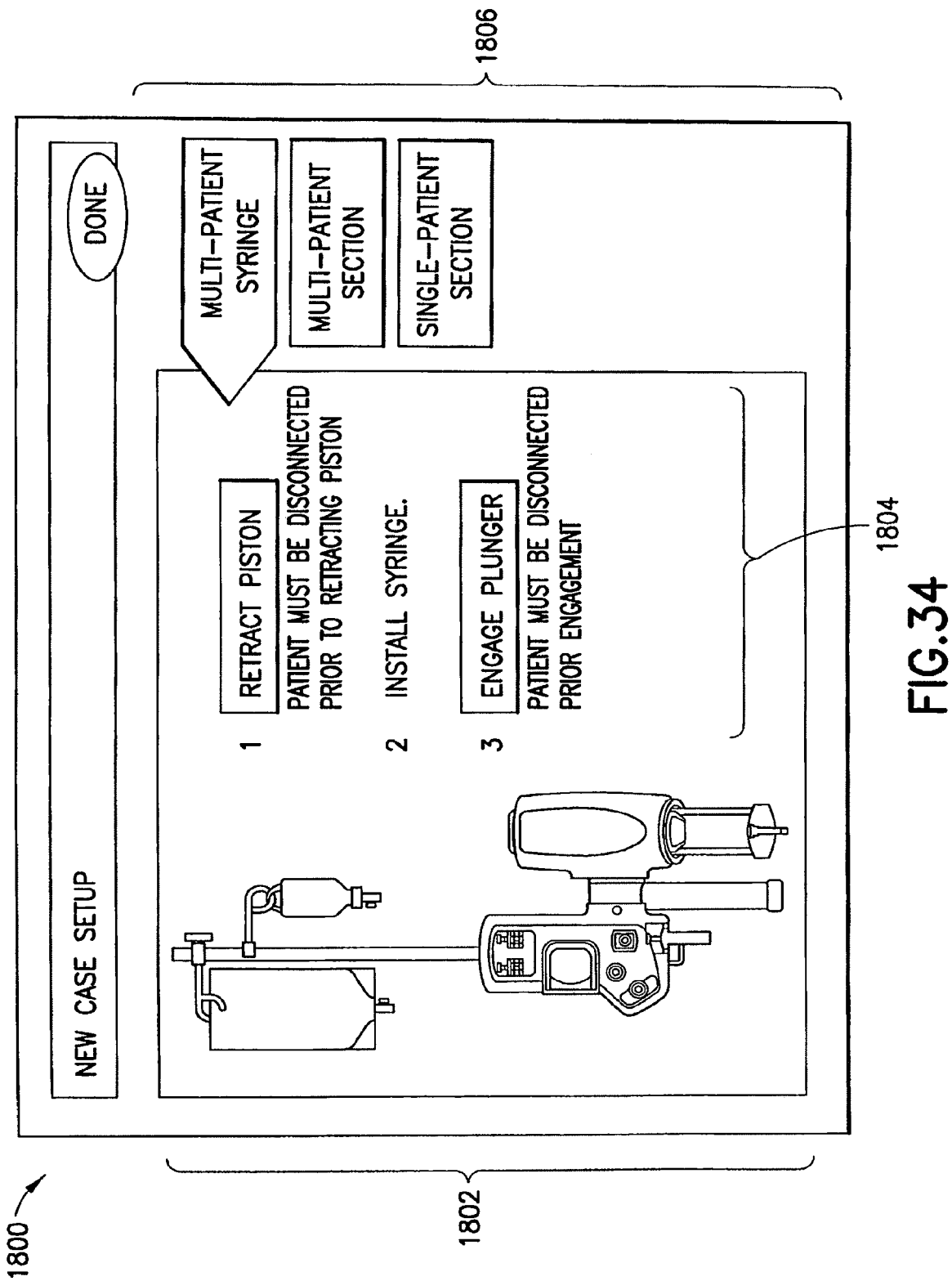
FIGS. 34-36 are respective graphical user interface displays of a setup wizard control system used to control the fluid delivery or injection system of the present invention.
Figure 35:
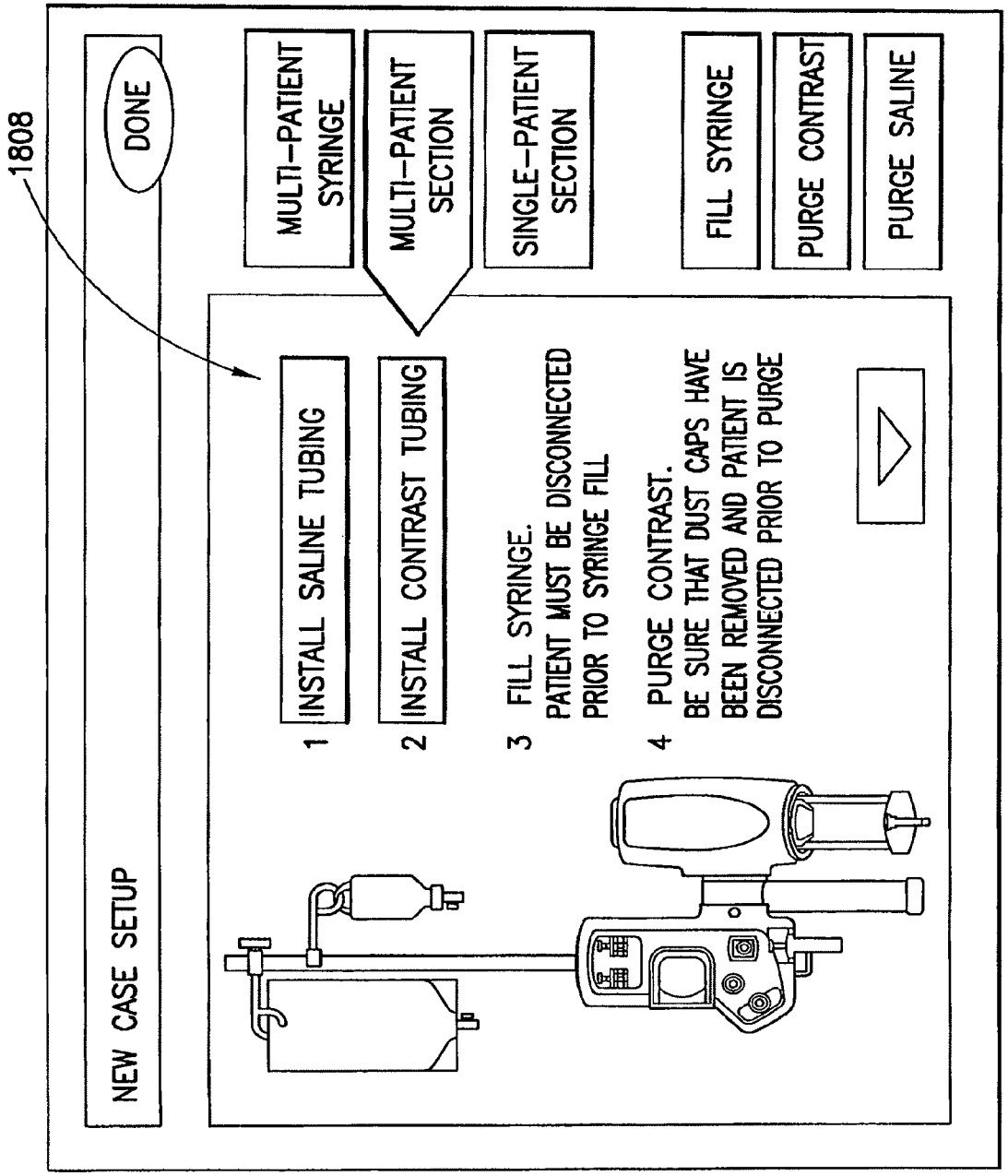
Figure 36:
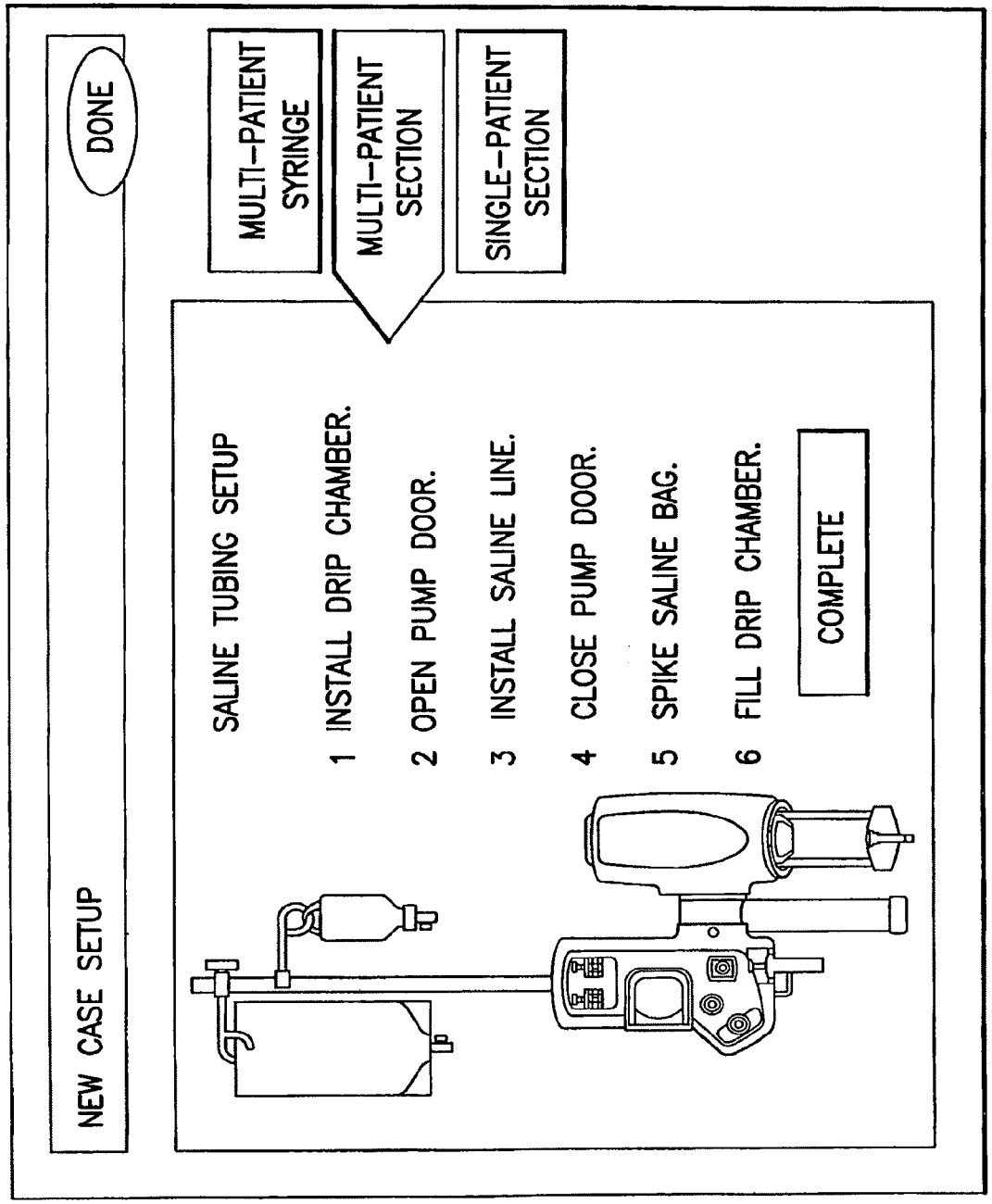

With reference to FIG. 34-36, the operator may utilize a setup wizard interface 1801 to aid in the installation and operation of the fluid delivery system 1200. Specifically, the setup wizard interface 1801 allows the operator of the fluid delivery system 1200 to follow graphical representations and textual instructions concerning the installation of various components and steps to be followed in ensuring proper operation of the fluid delivery system 1200. The exemplary setup wizard interface 1801 is accessed from the main control screen and is displayed on the user display 210. The setup wizard interface 1801 may be divided into distinct portions, such as a graphical portion 1802, an instructional portion 1804, and an individual component and process setup portion 1806. The individual component and process setup portion 1806 may include a series of on-screen buttons such as a "Multi-Patient Syringe" button, a "Multi-Patient Section" button, and a "Single Patient Section" button, relating to respective components of the fluid delivery system. Additionally, the individual component setup and process setup portion 1806 may include another series of buttons such as a "Fill Syringe" button, a "Purge Contrast" button, and a "Purge Saline" button, relating to respective processes of the fluid delivery system 1200. Desirably, each of these buttons maintains a series of corresponding instructions associated therewith, that display within the instructional portion 1804 of the setup wizard when the respective button is selected. The instructions displayed within the instructional portion 1804 may also reference related portions of the fluid delivery system 1200, or parts thereof that are graphically depicted within the graphical portion 1802. Furthermore, the instructions of the instructional portion 1804 may also contain embedded buttons associated with other instructions for components or installation procedures related thereto. When these additional buttons are selected, the instructions associated therewith are then displayed in the same instructional portion 1804. For example, if the operator selects an "Install Saline Tubing" 1808 button, as shown in FIG. 35, the instructions associated therewith, namely: (1) Install drip chamber; (2) Open pump door; (3) Install saline line; (4) Close pump door; (5) Spike saline bag; and, (6) Fill drip chamber, appear within the instructional portion 1804, as shown in FIG. 36. The instructional portion 1804 may also display related tips, warnings, or advisements. For example, a message informing the operator that the patient must be disconnected prior to engagement of the plunger, displays beneath the "Engage plunger" instruction, as shown in FIG. 34.

As shown in FIGS. 34-36, the setup wizard interface 1801 is laid out such that certain instructional portions 1804 of the pre-injection setup sequence may be bypassed depending upon the operator's familiarity with the setup of the fluid delivery system 1200. Thus, the operator need not follow the instructions provided by the setup wizard interface 1801 in a linear fashion. For example, a novice operator may want to proceed linearly with the instructions for setup, whereas a more skilled operator may want to view only instructions regarding setup of specific components and installation steps of the fluid delivery system 1200. The setup wizard interface 1801, therefore, efficiently conveys the requisite information for proper setup of the fluid delivery system 1200 to operators of various degrees of familiarity and knowledge of the fluid delivery system 1200.

Once the necessary components of the fluid delivery system are properly installed, the operator of the fluid delivery system 1200 may administer either a fixed rate injection or a variable rate injection in conjunction with a saline flush delivery. The user display allows the operator to input various data relating to each type of injection to be administered. Additionally, the user display 210 preferably provides visual and/or audio feedback during the delivery of the contrast in the injection cycle including, but not limited to, values corresponding to the flow rate, volume, and pressure limit relating to that particular injection cycle. It is to be understood that values displayed on the display 210 unit may be dynamic, such that with each varying plunger depression of the hand controller 400, new values for the flow rate, volume, and pressure limit may be displayed on the user display.

The fluid delivery system 1200 provides for various modes of refilling the syringe once the fluid delivery system 1200 determines that there is insufficient contrast media to perform an injection. A full automatic type refill is defined as a refill that occurs after the initial filling of the syringe 1702. The full automatic type of refill automatically fills the syringe 1702 with a maximum volume of contrast media that the syringe 1702 may hold, for example, 150 mL. Thus, in a full automatic type refill, refill commands are automatically given from the user display 210 without any operator intervention. A predetermined automatic type of refill fills the syringe 1702 with a predetermined operator specified volume, for example 25, 50, 75, or 100 mL. Thus, if there is insufficient contrast in the syringe 1702 to complete the next injection, the operator is prompted for permission by the user display as to whether or not the fluid delivery system should be allowed to initiate a refill to the predetermined volume. A manual type of fill allows the operator to fill the syringe 1702 by utilizing the on-screen controls, whenever the operator deems a refill to be necessary. Thus, a manual type fill includes a start and stop refill function associated therewith. However, the manual fill is still subject to programming of the fluid delivery system 1200 and the operator, in the manual fill mode, will be selecting from a menu of fill levels rather than an independently chosen level. Prior to each injection, the operator may indicate to the fluid delivery system 1200 which refill type is to be used when additional contrast is required to finish an injection. Once a refill type is selected, the refill type remains in place until changed by the operator. In an exemplary embodiment, the operator may touch a "Protocol" button on the main control screen to display a protocol screen with an "Options" button displayed thereon. The operator touches the "Options" button, which causes a list of options to appear, such as a "Refill Type" button. After touching the "Refill Type" button, the operator is typically presented with three refill types, namely (1) Full Automatic, for example to 150 mL; (2) Predetermined, for example 25, 50, 75, or 100 mL; and, (3) Manual. If the operator selects the full automatic refill, then a pop-up window confirming the automatic refill request may appear. If the operator selects the predetermined refill, a list of fill volumes appears, which requires the operator to choose from one of the fill volumes. Desirably, the fill volumes are listed in manageable 25 mL increments, as an example. If the operator selects the manual refill, then a pop-up window confirming the manual refill request may appear. Once the operator is satisfied with using a particular refill type for the instant injection cycle, the operator may then confirm the use of this refill type by touching another confirmation button, such as an "OK" button.

The fluid delivery system 1200 may maintain pre-programmed fluid delivery programs, (i.e., protocols), stored therein. Thus, instead of manually entering the desired flow rate, volume, pressure limit, rise time, and optionally delay for each injection cycle, the operator may program and store protocols, and recall previously stored protocols corresponding to injection elements, such as the desired flow rate, volume, pressure limit, rise time, and optionally delay. In an exemplary embodiment, a protocol is programmed and recalled via the on-screen controls of the user display 210. Specifically, the operator navigates to the protocol screen by touching, for example, the "Protocol" button, if not there already. Thereafter, the operator touches a "Fixed Flow" or "Variable Flow" mode button, which indicates whether a protocol relating to a fixed or variable flow injection, respectively, will be programmed. It is to be understood that not all injection elements may be changed by the operator when entering values relating to the variable flow injection.

A pop-up window confirming the request to enter into programming mode may appear, which requires the operator to confirm the request. The operator then touches a flow rate button. Visual indicia, such as inversing the color of the button, may indicate that indeed this or any button was touched by the operator. A parameter range for the allowable flow rate is displayed, along with the virtual numeric keyboard for entering the flow rate. The operator enters the desired flow rate and may touch a confirmation button, such as "Enter" to confirm the entered flow rate. Next, the operator touches a volume button. A parameter range for the allowable volume is displayed, along with the virtual numeric keyboard for entering the volume. The operator enters the desired volume and may confirm the volume by touching the "Enter" button. Then, the operator touches a pressure limit button. A parameter range for the allowable pressure range is displayed, along with the virtual numeric keyboard for entering the pressure. The operator enters the desired pressure and may confirm the pressure by touching the "Enter" button. Then, the operator touches a "Rise" button. A parameter range for the allowable rise time is then displayed, along with the virtual numeric keyboard for entering the rise time. The operator enters the rise time and may confirm the rise time by touching the "Enter" button. It is to be understood that any of the above values be entered in varying orders. The fluid delivery system 1200 is programmed to alert the operator if a requested command or entered value is outside the predefined parameters. This alert may be accomplished through either audio or visual indicia, such as a beep or an on-screen alert message, respectively.

After entering the appropriate values for a protocol, the operator may store the protocol into any available memory position of the fluid delivery system 1200 for future use of the protocol in other injection cycles with other patients. Specifically, the operator touches a "Store" button. The virtual alphanumeric keyboard for entering a name for the corresponding protocol is displayed. The operator may enter an appropriate name and confirm the name by touching the "Enter" button.

The operator may recall any previously stored protocol from the memory of the fluid delivery system 1200. For example, the operator may navigate to the protocol screen by touching a "Protocol" button, if not already there. Thereafter, the operator touches a "Recall" button. The fluid delivery system displays a screen showing all available, saved, pre-programmed protocols. The operator may recall, or select any of the protocols by touching the corresponding button of the protocol. Accordingly, the fluid delivery system displays the values associated with that particular protocol, as previously stored in memory. If the operator is satisfied with using this protocol for the instant injection cycle, the operator may confirm the use of this protocol by touching another confirmation button, such as an "OK" button.

Once the appropriate protocol is selected and is initiated with the fluid delivery system 1200, the corresponding fixed rate injection or a variable rate injection may be performed. It is to be understood that either the fixed rate or the variable rate injections may be performed by the hand controller 400. Alternatively, injections may be performed directly through the on-screen controls of the user display 210, bypassing the need for the hand controller 400 or the foot pedal.

In an exemplary embodiment, the fixed rate injection is initiated by the operator by depressing the plunger on the hand controller 400. Subsequently, the air detector assembly 1412 turns on and begins to monitor for any air within the lines. The multi-position valve 1712 rotates to the inject position. The injector piston accelerates to a programmed rate in the rise time allotted. The contrast media flows until either the operator releases the plunger or the programmed volume, as specified by the protocol, is delivered. After any of these conditions has been met, the injector piston ceases forward movement. Then the multi-position valve 1712 rotates to a closed or isolate position preferably after a set period of time to allow residual contrast media to exit the syringe 1702, and the air detector assembly 1412 enters into a sleep-mode.

In an exemplary embodiment, the variable rate injection is initiated by the operator by depressing the plunger on the hand controller 400. Subsequently, the air detector mechanism 1412 turns on to monitor for any air within the lines. The multi-position valve 1712 rotates to the inject position. The injector piston moves forward corresponding to a percentage of an acceleration rate as determined by the position of the plunger of the hand controller 400. The contrast flows until either the operator releases the plunger or the programmed volume, as specified by the protocol, is delivered. After any of these conditions is met, the injector piston ceases forward movement. Thereafter, the multi-position valve 1712 preferably remains open for a preset or predetermined amount of time, to allow residual contrast media to exit the syringe 1702. Then, the multi-position valve 1712 rotates to a closed position. If the entire programmed volume is delivered in a variable flow rate mode, then the injector 1300 rearms. If the operator releases the hand controller actuating member or assembly before the entire programmed volume is delivered, the multi-position valve 1712 remains open for the predetermined amount of time and then closes. It is to be understood that at the end of each variable rate injection, the fluid delivery system 1200 creates a sharp bolus within the contrast tubing downstream of the multi-position valve 1712, by suppressing the delivery of contrast media that is not delivered at the programmed flow rate. A sharp bolus of contrast media may be defined as a distinct or defined column of liquid having well-defined opposing ends or boundaries. However, the creation of the sharp bolus results in pressure buildup upstream of the multi-position valve 1712. To remove the excess pressure, the multi-position valve 1712 may have a simple vent for expelling liquid and relieving the excess pressure. Alternatively, the injector piston may be moved slowly backward or proximally in a controlled manner, so that no vacuum is created in the contrast tubing, and so that no audible sound, such as a whizzing sound, is produced. Desirably, this result is accomplished by having the fluid delivery system 1200 turning the voltage applied to the injector head motor on and off in short increments, thereby creating a controlled sequence of release/stop movements of the injector piston until the pressure in the syringe 1702 is equalized. After the pressure drops to the system friction of the fluid delivery system 1200, which is mostly comprised of the static friction between the syringe plunger and the syringe 1702 and the internal mechanical components of the injector head of the injector 1300, the fluid delivery system 1200 is ready for another injection. This process is repeated until the programmed volume has been delivered. Thereafter, the air detector assembly 1412 enters into a sleep-mode.

The saline flush delivery or injection may be performed at any time during the injection cycle, except when contrast is flowing. In an exemplary embodiment, initiating the saline injection requires the operator to depress the saline actuator or saline button of the hand controller 400. Subsequently, the air detector assembly 1412 of the fluid control module 1400 turns on to monitor for any air in the medical tubing associated with the saline portion of the fluid path set 1700. The pinch valve 1410 retracts to allow for the flow of saline from the secondary fluid container 1706. The fluid delivery system 1200 may be configured to permit the flow of saline until the operator releases the saline button on the hand controller 400, presses the saline button again, or until a predetermined amount of time lapses from the initiation of the flow of saline. The saline flow stops once movement in the peristaltic pump 1408 ceases. Thereafter, the pinch valve 1410 moves to a closed position and the air detector assembly 1412 enters into a sleep-mode.

During either the fixed rate injection cycle or the variable rate injection cycle, the fluid delivery system 1200 may display an instantaneous average value for a corresponding flow rate, fluid pressure, volume delivered for the most recent individual injection within the injection cycle, and a cumulative volume delivered to the patient, up to and including, the most recent injection. At the conclusion of the delivery, the fluid delivery system 1200 may display a peak flow rate, a peak fluid pressure, a volume delivered for the most recent individual injection within the injection cycle, and a cumulative volume delivered to the patient during the entire delivery.

It is to be understood that the fluid delivery system may exist in either an armed or unarmed state, which corresponds respectively to whether or not the operator is allowed to perform an injection. The fluid delivery system 1200 may enter a disarmed or safe state when certain conditions are met including, but not limited to, failure of a self-diagnostic check, detection of air in either the contrast or saline portions of the fluid path set 1700, absence of some of the requisite components, and the reaching of a pressure limit that is deemed to be unsafe for the patient. The converse of these conditions and/or other factors must be present for the fluid delivery system 1200 to enter the armed state. The fluid delivery system 1200 may provide various visual and/or audible alarms to the operator to identify specific conditions that arise during the functioning of the fluid delivery system 1200. Such conditions may include, but are not limited to the arming/disarming of the fluid delivery system 1200 and the state thereof, the detection of air in the fluid path, the insufficiency or unavailability of fluid in the fluid delivery path or fluid supply to perform an injection, and the reaching of a pressure disarm limit.

Figure 32:
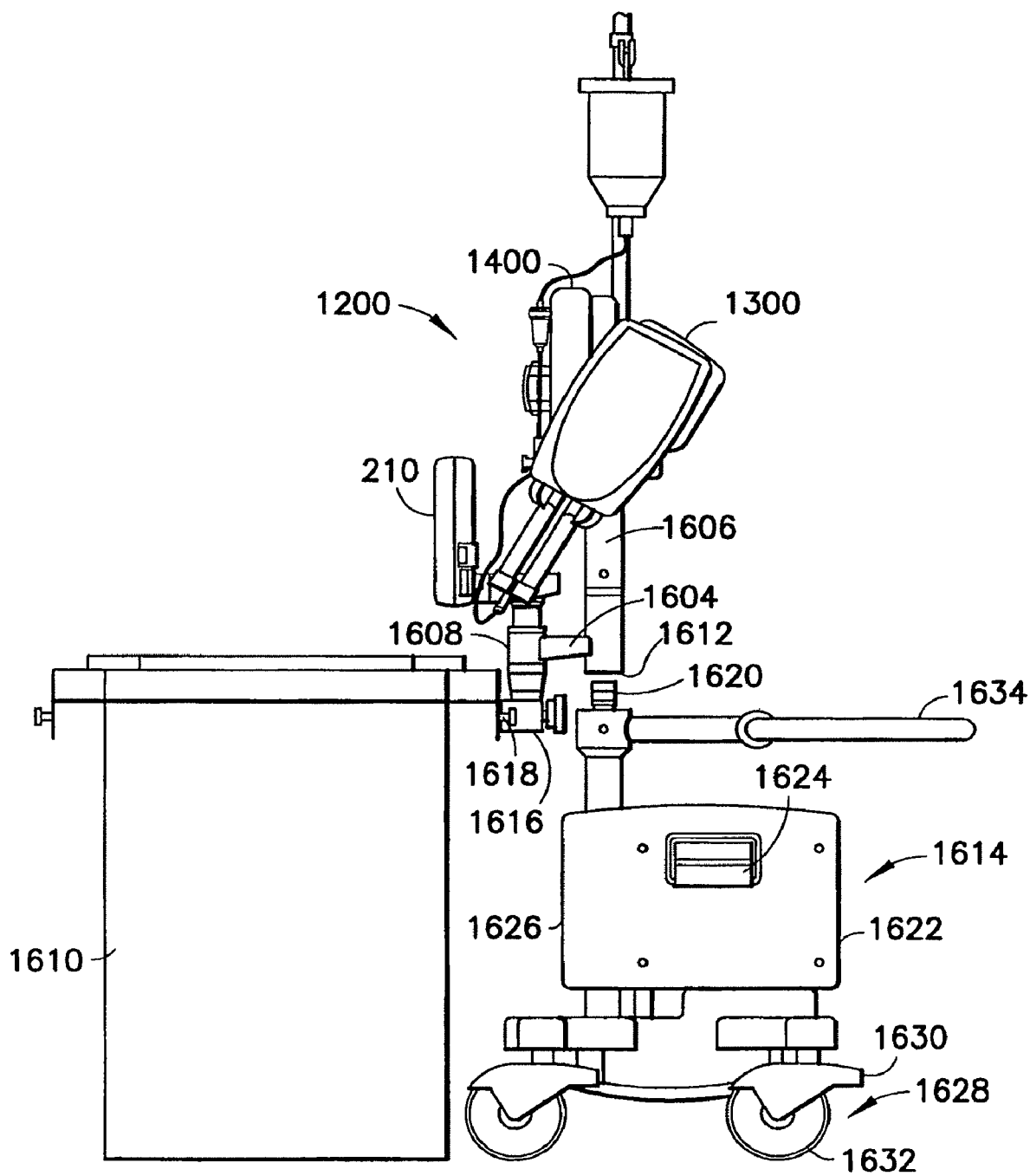
FIG. 32 is an elevational view of the fluid delivery or injection system of FIG. 9 associated with a hospital examination table.
Figure 33:
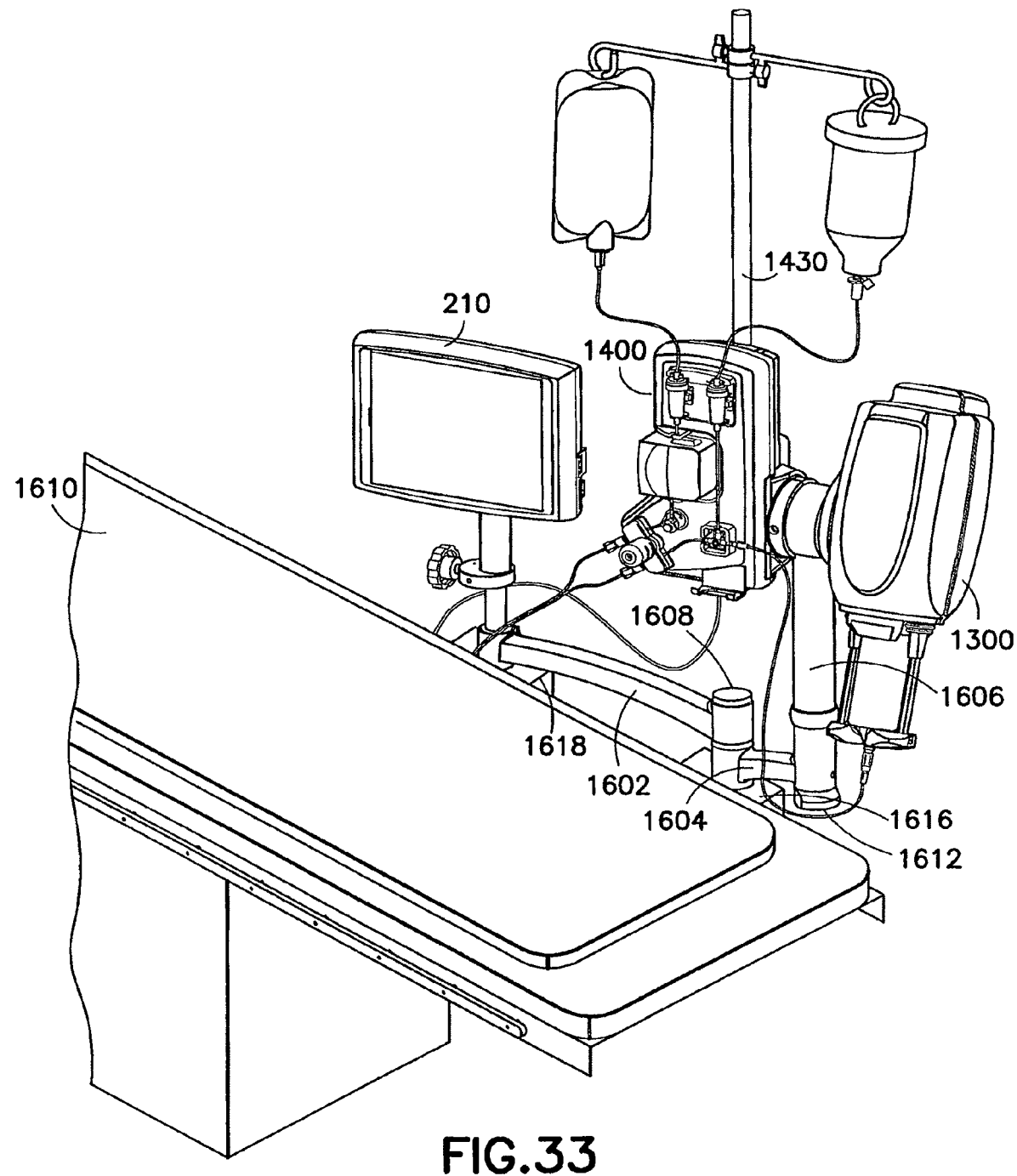
FIG. 33 is a top perspective view of the fluid delivery or injection system of FIG. 32.

With reference to FIGS. 32 and 33 and with continuing reference to FIG. 9, the support assembly 1600 of the fluid delivery system 1200 includes a support arm 1602 for supporting the control section 1800 and the user display 210 in particular. A second support arm 1604 extends from a support column 1606 that generally supports the injector and fluid control module 1400. The support arms 1602, 1604 are associated with a rail interface 1608 which is generally adapted to attach the fluid delivery system 1200 to a hospital be or examination table 1610. The support column 1606 may include a pedestal interface 1612 for attaching the fluid delivery system 1200 to a movable pedestal 1614. As shown in FIG. 32, the fluid delivery system may either be attached to the examination table 1610 or the movable pedestal 1614 to provide the maximum amount of flexibility and ease in utilizing the fluid delivery system 1200. Thus, when the fluid delivery system 1200 is mounted to the examination table 1610, a rail mount 1616 is attached to a rail 1618 of the examination table 1610. This allows the rail interface 1608 to be removably attached to the rail mount 1616. Thus, the rail mount 1616 indirectly supports the user display 210, the injector 1300, and the fluid control module 1400. In an alternative embodiment, as shown in FIG. 33, only the injector 1300 and the fluid control module 1400 are indirectly supported by the rail mount 1616, and an additional rail mount 1616 may be utilized to independently support the user display 210 at a different location on the rail 1618 of the examination table 1610. Returning to FIG. 32, the movable pedestal 1614 provides mobility to the fluid delivery system 1200 and height adjustability features. The movable pedestal 1614 includes a pedestal interface mount 1620 extending therefrom, for attaching the pedestal interface 1612 to the movable pedestal 1614. The pedestal interface mount 1620 may be configured to interface with electrical connections from the pedestal interface 1612. The movable pedestal 1614 further includes a base 1622 for holding loose components related to the fluid delivery system 1200 and the power cables associated therewith. A handle 1624 provides access to the interior of the base 1622. The base 1622 may also include a power socket 1626 that interfaces with the power cables (not shown) within the base 1622. Thus, a single external power cable (not shown) may be plugged directly into the power socket 1626 to provide sufficient power for operation of the entire fluid delivery system 1200. The movable pedestal 1614 may also include a plurality of casters 1628 having lockable brakes 1630 and wheels 1632. A handle 1634 may be attached to the movable pedestal 1614 to facilitate movement of the fluid delivery system 1200. By aligning the rail interface 1608 over the rail mount 1616 and then lowering the height of the movable pedestal 1614, the fluid delivery system 1200, may easily be transferred from the pedestal 1614 and to the bed 1610. It is to be understood that the aforementioned configurations are not to be considered as limiting the placement and positioning of the fluid delivery system 1200.

Although the present invention has been described in detail in connection with the above embodiments and/or examples, it is to be understood that such detail is solely for that purpose and that variations can be made by those skilled in the art without departing from the invention. The scope of the invention is indicated by the following claims rather than by the foregoing description. All changes and variations that come within the meaning and range of equivalency of the claims are to be embraced within their scope.

The invention claimed is:

1. An injector system comprising:
 a source of injection fluid;
 a pump device;
 a fluid control device operably associated with the pump device;
 a fluid path set in fluid connection with the source of injection fluid and the pump device, the fluid path set comprising a drip chamber comprising an elongated body having a top end, a bottom end and a raised projection, the raised projection being substantially rectangular in shape and extending longitudinally from the top end along the drip chamber body and terminating adjacent to the bottom end; and
 a fluid level sensing mechanism operably associated with the fluid control device, the fluid level sensing mechanism comprising:
  a drip chamber support for supporting the drip chamber body; and
  a fluid level sensor comprising an ultrasonic or an optical sensor associated with the drip chamber support, the drip chamber support adapted to support the drip chamber body such that the raised projection is in operational contact with the fluid level sensor and the fluid level sensing mechanism is operable to transmit ultrasonic or light energy through the raised projection to be sensed by the fluid level sensor for sensing the injection fluid level in the drip chamber.

2. The injector system of claim 1 wherein the pump device comprises a powered injector.

3. The injector system of claim 1 wherein the fluid control device comprises a valve actuator and the fluid path set further comprises a multi-position valve adapted to be placed in operative engagement with and actuated by the valve actuator.

4. The injector system of claim 3 wherein the valve actuator comprises a position indicator indicating a position of the multi-position valve.

5. The injector system of claim 3 wherein the valve actuator further comprises a retainer for removably supporting the multi-position valve.

6. The injector system of claim 3 wherein the valve actuator comprises a sensor indicating the presence of the multi-position valve in the valve actuator and adapted to close the multi-position valve to stop flow of the injection fluid to the patient at substantially any pressure or flow rate generated by the pump device for delivering a sharp bolus of the injection fluid to the patient.

7. The injector system of 1, further comprising a hand held control device in operative association with the fluid control device for controlling the flow rate of the injection fluid delivered by the pump device.

8. The injector system of claim 1, further comprising an air detector assembly operatively engaged with a portion of the fluid path set and adapted to detect the presence of air in the fluid path set.

9. The injector system of claim 8 wherein the air detector assembly comprises:
 an air column detector adapted to detect the presence of air in the portion of the fluid path set; and
 a retaining device for securing the portion of the fluid path set in operative engagement with the air column detector, the retaining device comprising:
  a base adapted for association with the air column detector; and
  a closure member connected to the base and adapted to secure the portion of the fluid path set in operative engagement with the air column detector, wherein the closure member is movable from a closed position wherein the closure member secures the portion of the fluid path set in operative engagement with the air column detector, and an open position allowing the portion of the fluid path set to be disassociated from the air column detector, the closure member biased to the open position.

10. The injector system of claim 9 wherein the closure member is secured in the closed position by a releasable locking mechanism.

11. The injector system of claim 9 wherein the closure member is formed of substantially clear plastic material to permit viewing of the portion of the fluid path set.

12. The injector system of claim 10 wherein the locking mechanism is adapted to maintain the closure member in the closed position against the biased closure member and is automatically releasable to allow the biased closure member to move to the open position.

13. The injector system of claim 12 wherein the locking mechanism is adapted to be automatically released by actuating a button associated with the locking mechanism.

14. The injector system of claim 1, further comprising: a source of medical fluid associated with the fluid path set; and a pump operatively associated with the fluid path set for supplying the medical fluid to the patient.

15. The injector system of claim 14, further comprising a second air detector assembly operatively associated with the fluid path set.

16. The injector system of claim 14 wherein the fluid control device further comprises a shut-off valve associated with the fluid path set for stopping flow of the medical fluid from the pump to the patient.

17. The injector system of claim 16 wherein the shut-off comprises an automated pinch valve.

18. The injector system of claim 14 wherein the pump comprises a peristaltic pump.

19. The injector system of claim 14 wherein the fluid control device further comprises guides for securing the fluid path set in association with the pump.

20. The injector system of claim 1 wherein the fluid control device is disposed downstream of the pump device.

* * * * *

UNITED STATES PATENT AND TRADEMARK OFFICE
CERTIFICATE OF CORRECTION

| | |
|---|---|
| PATENT NO. | : 8,147,464 B2 |
| APPLICATION NO. | : 12/476513 |
| DATED | : April 3, 2012 |
| INVENTOR(S) | : Spohn et al. |

It is certified that error appears in the above-identified patent and that said Letters Patent is hereby corrected as shown below:

ON THE TITLE PAGE:
Item (75), under "Inventors", in Column 1, Line 3, delete "Ehrenberg" and insert -- Ehrenberger -- therefor.

Item (75), under "Inventors", in Column 1, Line 9, delete "Herbert" and insert -- Herb -- therefor.

IN THE DRAWINGS:
In Fig. 3, Sheet 3 of 37, delete "PESSURE" and insert -- PRESSURE -- therefor.

IN THE SPECIFICATION:
In Column 37, Line 54, delete "air in to" and insert -- air is not introduced into -- therefor.
In Column 51, Line 36, delete "hospital be" and insert -- hospital bed -- therefor.

IN THE CLAIMS:
In Column 53, Lines 1-2, in Claim 6, delete "to stop the flow of the injection fluid to the patient." and insert -- to stop flow of the injection fluid to a patient. -- therefor.

In Column 53, Line 5, in Claim 7, delete "of 1," and insert -- of claim 1, -- therefor.

In Column 53, Line 7, in Claim 7, delete "for controlling the flow rate" and insert -- for controlling a flow rate -- therefor.

In Column 53, Line 11, in Claim 8, delete "to detect the presence of air" and insert -- to detect a presence of air -- therefor.

In Column 53, Lines 25-28, in Claim 9, delete "fluid path set in operative engagement with the air column detector, and an open position" and insert -- fluid path set in operative engagement with the air column detector, to an open position -- therefor.
IN THE CLAIMS:

Signed and Sealed this
First Day of July, 2014

Michelle K. Lee
*Deputy Director of the United States Patent and Trademark Office*

CERTIFICATE OF CORRECTION (continued)
U.S. Pat. No. 8,147,464 B2

In Column 54, Lines 5-7, in Claim 12, delete "maintain the closure member in the closed position against the biased closure member and is automatically releasable" and insert -- maintain the closure member in the closed position and is automatically releasable -- therefor.

In Column 54, Line 15, in Claim 14, delete "supplying the medical fluid to the patient." and insert -- supplying the medical fluid to a patient. -- therefor.

In Column 54, Lines 23-24, in Claim 17, delete "wherein the shut-off comprises" and insert -- wherein the shut-off valve comprises -- therefor.